(12) United States Patent
Olek et al.

(10) Patent No.: US 12,286,675 B2
(45) Date of Patent: Apr. 29, 2025

(54) EPIGENETIC MARKERS FOR THE IDENTIFICATION OF BLOOD SUB-CELLS OF TYPE 1

(71) Applicant: Precision for Medicine GmbH, Berlin (DE)

(72) Inventors: Sven Olek, Berlin (DE); Ivana Turbachova, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 307 days.

(21) Appl. No.: 16/379,260

(22) Filed: Apr. 9, 2019

(65) Prior Publication Data

US 2019/0241957 A1 Aug. 8, 2019

Related U.S. Application Data

(63) Continuation of application No. 15/477,768, filed on Apr. 3, 2017, now abandoned, which is a continuation-in-part of application No. 13/139,808, filed as application No. PCT/EP2009/008764 on Dec. 8, 2009, now abandoned.

(30) Foreign Application Priority Data

Dec. 16, 2008 (EP) ..................... 08021838

(51) Int. Cl.
C12Q 1/6881 (2018.01)

(52) U.S. Cl.
CPC ..... *C12Q 1/6881* (2013.01); *C12Q 2600/154* (2013.01); *C12Q 2600/158* (2013.01)

(58) Field of Classification Search
CPC ............ C12Q 1/6881; C12Q 2600/154; C12Q 2600/158
See application file for complete search history.

(56) References Cited

U.S. PATENT DOCUMENTS

| | | | |
|---|---|---|---|
| 9,783,846 B2 | 10/2017 | Olek | |
| 9,840,736 B2 | 12/2017 | Olek | |
| 9,926,599 B2 | 3/2018 | Olek | |
| 2002/0072059 A1* | 6/2002 | Shiota | C12Q 1/6881 435/6.14 |
| 2007/0269823 A1* | 11/2007 | Huehn | C12Q 1/6886 435/6.16 |
| 2012/0107810 A1 | 5/2012 | Olek | |
| 2013/0005600 A1 | 1/2013 | Olek | |

OTHER PUBLICATIONS

Ehrlich et al. (2002 Oncogene vol. 21 p. 5400).*
Walsh et al teaches (Genes & Development (1999) vol. 13, pp. 26-36).*
Brooks et al (Cancers Causes control (2009) vol. 20, pp. 1539-1550).*
Ushijima (Nature Reviews. 2005. 5: 223-231).*
Sabbioni et al (Mol Diagn 7(3):201-207 [2003]).*
Zhang (PLOS Genetics (2009) vol. 5, e1000438).*
Mackall et al. (1994) Blood, 84(7):2221-2228).*
Wilson (Wilson et al. (2005) Seminars in Immunology, 17:105-119).*
Flanagan et al. (1990) Immunogenetics, 31:13-20).*
Cruse et al. "Atlas of Immunology, Second Edition". Boca Raton:CRC Press, 2004, chapter 9, 33 pages.*
Hajkova et al. "DNA-Methylation Analysis by the Bisulfite-Assisted Genomic Sequencing Method", in Mills et al., Methods in Molecular Biology, vol. 200: DNA Methylation Protocols, (Humana Press, Totowa, 2002), pp. 143-154.*
Clevers (The EMBO Journal (1989) vol. 8, pp. 2527-2535).*
Evans (Immunogentics (1988 volume 28, pp. 365-373).*
*Homo sapiens* genomic DNA, chromosome 11q, clone:RP11-215H18, complete sequence GenBank: AP001582.4 (https://www.ncbi.nlm.nih.gov/nucleotide/AP001582.4?report=genbank&log$=nucltop&blast_rank=1&RID=HCU61WTP016, Mar. 15, 2003).*
Multiple sequence alignment by MAFFT ver.7 (cbrc.jp), Sep. 27, 2022).*
Results for job clustalo-I20230118-135801-0984-62721960-p1m (Results < Clustal Omega < Multiple Sequence Alignment < EMBL-EBI, downloaded Jan. 18, 2022).*
Results for job Results for job clustalo-I20230118-134612-0826-61618636-p1m (Results < Clustal Omega < Multiple Sequence Alignment < EMBL-EBI, downloaded Jan. 18, 2022).*
AquinodeMuro et al., "Probe Design, Production, and Applications.", Medical Biomethods Handbook, 2005, pp. 13-23, vol. 656.
Clevers et al., "An Enhancer Located in a CpG-island 3' to the TCR/CD3-E Gene Confers T Lymphocyte-Specificity to its Promoter.", The EMBO Journal, Sep. 1989, pp. 2527-2535, vol. 8, No. 9.
Comans-Bitter et al., "Immunophenotyping of blood lymphocytes in childhood.", The Journal of Pediatrics, 1997, pp. 388-393, vol. 130, No. 3.
Cruse et al., "Atlas of Immunology, Second Edition.", Boca Raton: CRC Press, 2004, vol. 9, 13 pages.

(Continued)

*Primary Examiner* — Steven Pohnert
(74) *Attorney, Agent, or Firm* — BakerHostetler

(57) ABSTRACT

The present invention relates to a method, in particular an in vitro method, for identifying CD3CD4 positive T lymphocytes of a mammal, wherein said method comprises analysing the methylation status of at least one CpG position in the CD3a/b/c/d/g genes, in particular their "upstream" regulatory regions, and in particular the promoter and other conserved regions of the gene cd3, wherein a demethylation of at least one CpG in the analyzed sample to at least 90% is indicative for memory and naive CD4 or/and memory and/or naive T lymphocytes. Furthermore, the present invention is directed at the use of DNA-methylation analysis of the genes CD3a/b/c/d for the detection and quality assurance and control of T lymphocytes. Furthermore, the present invention relates to a kit for performing the above methods as well as respective uses thereof. In a preferred embodiment, the present invention furthermore provides an improved method for analysing the methylation status of at least one CpG position in the gene CD3, allowing for a precise analysis even from sub-optimal quality samples, such as non-freshly obtained blood or serum samples.

6 Claims, 16 Drawing Sheets

Specification includes a Sequence Listing.

(56) References Cited

OTHER PUBLICATIONS

Cruse et al., "Atlas of Immunology, Third Edition.", Boca Raton: CRC Press, 2010, pp. 316-318.
De Vaan et al., "T-Cell Qualities of Lymphocytes and/or Leukemic Cells from Peripheral Blood in Acute Myeloid and Lymphatic Leukemia Before Treatment and at Relapse.", Biomedicine, Nov. 1975, pp. 524-531, vol. 22.
Douer et al., "Thymic Humeral Factor in the Assessment of T Lymphocytes in a Patient with T Cell Chronic Lymphocytic Leukemia.", Israel Journal of Medical Science, Aug. 1978, pp. 870-875, vol. 14, No. 8.
Flanagan et al., "DNase Hypersensitivity and Methylation of the Human CD3G and D Genes During T-cell Development." Immunogenetics, 1990, pp. 13-20, vol. 31, No. 1.
Georgopoulos et al., "A T Cell-Specific Enhancer is Located in a DNase Ihypersensitive Area at the 3' End of the CD3-6 Gene.", The EMBO Journal, 1988, pp. 2401-2407, vol. 7, No. 8.
Golbus et al., "Quantitative changes in T cell DNA methylation occur during differentiation and ageing.", European Journal of Immunology, 1990, pp. 1869-1872, vol. 20.
Hajkova et al., "DNA-Methylation Analysis by the Bisulfite-Assisted Genomic Sequencing Method.", in Mills et al., Methods in Molecular Biology, {Humana Press), 2002, pp. 143-154, vol. 200.
Hennessey et al., "Promoter Methylation in Head and Neck Squamous Cell Carcinoma Cell Lines is Significantly Difference than Methylation in Primary Tumors and Xenografls.", PLoS ONE, May 2011, pp. 1-7, vol. 6, No. 5.
Lusso et al., "Induction of CD4 and Susceptibility to HIV-1 Infection in Human COB+ T Lymphocytes by Human Herpesvirus 6.", Letters to Nature, Feb. 1991, pp. 533-535, vol. 349, No. 6309.
Mackall et al., "Lymphocyte Depletion During Treatment with Intensive Chemotherapy for Cancer.", Blood, 1994, pp. 2221-2228, vol. 84, No. 7.
Sabin, A., "Viral Etiology of AIDS and the Gallo Probe.", Science, Aug. 1990, pp. 465-466, vol. 249, No. 4968.
Sambrook et al., "Identification of the ancestral killer immunoglobulin-like receptor gene in primates.", BMC 3eomics, 2006, pp. 1-8, vol. 7, No. 209.
Santourliidis et al., "Crucial Role of DNA Methylation in Determination of clonally Distributed Killer Cell Ig-like Receptor Expression Patterns in NK Cells.", The Journal of Immunology, 2002, pp. 4253-4261, vol. 169.
Smiraglia, et al., "Excessive CpG Island Hypermethylation in Cancer Cell Lines Versus Primary Human Malignancies.", Human Molecular Genetics, May 2001, 1413-1419, vol. 10, No. 13.
Sequence Analysis for SQ ID No. 1, "Alignment produced" Aug. 23, 2013, pp. 1.
Tan, A.G. et al., "Characterizing DNA Methylation Patterns in Pancreatic Cancer Genome.", Molecular Oncology, Apr. 2009, pp. 425-438, vol. 3.
Tarazona et al., "Increased expression of NK cell markers on T lymphocytes in aging and chronic activation of the Immune system reflects the accumulation of effector: senescent T cells.", Mechanisms of Ageing and Development, 2000, 121, pp. 77-88.
UCSC Genome Browser start site sequences for CD3 delta and CD3 gamma, screenshots accessed from <http:// Jenome.ucsc.edu>, Aug. 23, 2013, pp. 2.
Wilson et al., "DNA methylation and the expanding epigenetics of T cell lineage commitment", Seminars in Immunology, 2005, pp. 105-119, vol. 17.
Li et al., "MethPrimer: designing primers for methylation PCRs", Bioinformatics, 2002, 18(11), 1427-1431.
UCSC Genome Browser, "GRCh37/hg19 chr11:118,213,632-118,213,653, chr11:118,213,686-118, 213,709, and chr11:118,213,664-118,213,690", http://genome.ucsc.edu, May 29, 2018, 6 pages.

\* cited by examiner (Ref-Seq is SEQ ID No. 6)

```
Monocytes         -------------------------AGCCTCTTT-ATAA-TCTCAAAAAAA  24
NK-Cells          -------------------------AGCCTCTTT-ATAA-TCTCAAAAAAA  24
AMP1405 Ref-Seq   TTATTCCACCTATTACCTTCCAAACGCCTCTTT-ATAA-TCTCAAAAAAA  49
Granulocytes      -------------------------CGCCTCTTT-ATAA-TCTCAAAAAAA  24
mem. T-cells      -------------------------TACCTCTTT-ATAAATCTCAAAAAAA  25
mem. CTL          -------------------------GACCTCTTT-ATAA-TCTCAAAAAAA  24
naive CTL         -------------------------CGCCTCTTT-ATA--TCTAAAAAAA-  22
                                           ******  ***   ***  ******

Monocytes         TAATAAAACCAAATACCGTATCTCACGCCTATAATCCCAACACTTTAAAA  74
NK-Cells          TAATAAAACCAAATACCGTATCTCACGCCTATAATCCCAACACTTTAAAA  74
AMP1405 Ref-Seq   TAATAAAACCAAATACCGTATCTCACGCCTATAATCCCAACACTTTAAAA  99
Granulocytes      TAATAAAACCAAATACCGTATCTCACGCCTATAATCCCAACACTTTAAAA  74
mem. T-cells      TAATAAAACCAAATACCATATCTCACACCTATAATCCCAACACTTTAAAA  75
mem. CTL          TAATAAAACCAAATACCATATCTCACACCTATAATCCCAACACTTTAAAA  74
naive CTL         ---TATAAACCAATACCGTATCTCACACCTATAATCCCAACACTT-AAAA  68
                     **  ** * ****** ********* ******************  ****

Monocytes         AACTAAAACAAATAAATCACAAAATCAAAAATTCG-AAACCAACCTAACC 123
NK-Cells          AACTAAAACAAATAAATCACAAAATCAAAAATTCG-AAACCAACCTAACC 123
AMP1405 Ref-Seq   AACTAAAACAAATAAATCACAAAATCAAAAATTCG-AAACCAACCTAACC 148
Granulocytes      AACTAAAACAAATAAATCACAAAATCAAAAATTCG-AAACCAACCTAACC 123
mem. T-cells      AACTAAAACAAATAAATCACAAAATCAAAAATTCA-AAACCAACCTAACC 124
mem. CTL          AACTAAAACAAATAAATCACAAAATCAAAAATTCA-AAACCAACCTAACC 123
naive CTL         AACTAAAACAAATAAATCACAAAATCAAAAATTCAGAAACCAACCTAACC 118
                  **********************************  **************

Monocytes         AACAAAATAAAACCCCGTCTCTACTAAAAATACAAAAATTAACCGAACTT 173
NK-Cells          AACAAAATAAAACCCCGTCTCTACTAAAAATACAAAAATTAACCGAACTT 173
AMP1405 Ref-Seq   AACAAAATAAAACCCCGTCTCTACTAAAAATACAAAAATTAACCGAACTT 198
Granulocytes      AACAAAATAAAACCCCGTCTCTACTAAAAATACAAAAATTAACCGAACTT 173
mem. T-cells      AACAAAATAAAACCCCATCTCTACTAAAAATACAAAAATTAACCAAACTT 174
mem. CTL          AACAAAATAAAACCCCATCTCTACTAAAAATACAAAAATTAACCAAACTT 173
naive CTL         AACAAAATAAAACCCCGTCTCTACTAAAAATACAAAAATTAACCAAACTT 168
                  **************** ************************** *****

Monocytes         ACTAACACGCACCTATAATCTCAACTACTCAAAAAACTAAAACAAAAAAA 223
NK-Cells          ACTAACACGCACCTATAATCTCAACTACTCAAAAAACTAAAACAAAAAAA 223
AMP1405 Ref-Seq   ACTAACACGCACCTATAATCTCAACTACTCAAAAAACTAAAACAAAAAAA 248
Granulocytes      ACTAACACGCACCTATAATCTCAACTACTCAAAAAACTAAAACAAAAAAA 223
mem. T-cells      ACTAACACACACCTATAATCTCAACTACTCAAAAAACTAAAACAAAAAAA 224
mem. CTL          ACTAACACACACCTATAATCTCAACTACTCAAAAAACTAAAACAAAAAAA 223
naive CTL         ACTAACACACACCTATAATCTCAACTACTCAAAAAACTAAAACAAAAAAA 218
                  ******** *****************************************

Monocytes         TCGCTTAAACCCCGAAAATAAAAATTACAATAAACTAAAATAACGCCACT 273
NK-Cells          TCGCTTAAACCCCGAAAATAAAAATTACAATAAACTAAAATAACGCCACT 273
AMP1405 Ref-Seq   TCGCTTAAACCCCGAAAATAAAAATTACAATAAACTAAAATAACGCCACT 298
Granulocytes      TCGCTTAAACCCCGAAAATAAAAATTACAATAAACTAAAATAACGCCACT 273
mem. T-cells      TCACTTAAACCCCAAAAATAAAAATTACAATAAACTAAAATAACACCACT 274
mem. CTL          TCACTTAAACCCCAAAAATAAAAATTACAATAAACTAAAATAACACCACT 273
naive CTL         TCACTTAAACCCCAAAAATAAAAATTACAATAAACTAAAATAACACCACT 268
                  ** ********** ****************************** *****
```

FIG. 2A

```
Monocytes        ACACTCCAACCTAAACAACAAAATAAAACTCTATCTCAAAAAAAAAAAAA 323
NK-Cells         ACACTCCAACCTAAACAACAAAATAAAACTCTATCTCAAAAAAAAAAAAA 323
AMP1405 Ref-Seq  ACACTCCAACCTAAACAACAAAATAAAACTCTATCTCAAAAAAAAAAAAA 348
Granulocytes     ACACTCCAACCTAAACAACAAAATAAAACTCTATCTCAAAAAAAAAAAAA 323
mem. T-cells     ACACTCCAACCTAAACAACAAAATAAAACTCTATCTCAAAAAAAAAAAAA 324
mem. CTL         ACACTCCAACCTAAACAACAAAATAAAACTCTATCTCAAAAAAAAAAAAA 323
naive CTL        ACACTCCAACCTAAACAACAAAATAAAACTCTATCTCAAAAAAAAAAAAA 318
                 **************************************************

Monocytes        AAAAAAAAAA-AAAAAAAATTTCTAAAAAAAAACCCAAAAAAAAAAAACT 372
NK-Cells         AAAAAAAAAA-AAAAAAAATTTCCAAAAAAAAAACCCAAAAAAAAAAACT 372
AMP1405 Ref-Seq  AAAAAAAAAATAAAAAAAAATTCCTAAATAAAAACCTAAACTAAAATAACT 398
Granulocytes     AAAAAAAAAA-AAAAAAAATTTCCAAAAAAAAAACCCAAAAAAAAAAACT 372
mem. T-cells     AAAAAAAAAA-AAAAAAAATTTCCAAAAAAAAAACCCAAAAAAAAAAACT 373
mem. CTL         AAAAAAAAAA-AAAAAAAATTCCCAAAAAAAAAACCCAAAAAAAAAAACT 372
naive CTL        AAAAAAAAAA-AAAAAAAATTTCCAAAAAAAAAACCCAAAAAAAAAAACT 367
                 ********** ********  *  *******  ***    ****  ****

Monocytes        TTTCCTTTAAAAAACCCCCCCCAAAAATTT------- 402  (SEQ ID NO:39)
NK-Cells         TTCCCTTTAAAAAACCCCCCCC--------------- 394  (SEQ ID NO:40)
AMP1405 Ref-Seq  TTCCATTTAAAAATCCAACCCCAAACATCTAAAAATC 435   SEQ ID NO:6)
Granulocytes     TTCCCTTTAAAAAACCCCCCCAAAAA----------- 399  (SEQ ID NO:42)
mem. T-cells     TTCCCTTTAAAAACCCCCCCC---------------- 394   (SEQ ID NO:43)
mem. CTL         TTCCCTTTAAAAACCCCCCCCAA-------------- 396   (SEQ ID NO:44)
naive CTL        TTCCCTTTAAAAAACCCCCC----------------- 387  (SEQ ID NO:45)
                 ** * ******** **  **
```

FIG. 2B (Ref-Seq is SEQ ID No. 7, reverse)

```
Granulocytes     ----------------------CTGATTGTTA---TAGGGACGTTA--A  22
NK-Cells         ----------------------ATGATTGTTAA--TAGGGACGTTA--A  23
mem. T-cells     ------------------CTATTTGATGGGAGAAGTGAGGT-GTTAATA  30
naive CTL        ------------------CTATTTGATGGGAGAAGTGAGGTTGTTAATA  31
mem. CTL         ---------------------CATTGATGGGAAGTAGAGGATTGATA--A  27
naive T-cells    ------------------ATTGGTATGTGTTAAGTATGGGATGTGTA--A  30
Monocytes        --------------------CTG-ATTGTTAA--TAGGGACGTTA--A  23
AMP1406 Ref-Seq  TTTAGGTTGTGTGTAAATGTGGTTGTATTGTTAA--TAGGGACGTTA--A  46
                                              *         *    **   *

Granulocytes     AGTTTAGGTTATTTTTTTTATATTTTTGTTAGTTTTTTGTTTAGAGATA  72
NK-Cells         AGTTTAGGTTATTTTTTTTATATTTTTGTTAGTTTTTTGTTTAGAGATA  73
mem. T-cells     AGTTTAGGTTATTTTTTTTATATTTTTGTTAGTTTTTTGTTTAGAGATA  80
naive CTL        AGTTTAGGTTATTTTTTTTATATTTTTGTTAGTTTTTTGTTTAGAGATA  81
mem. CTL         AGTTTAGGTTATTTTTTTTATATTTTTGTTAGTTTTTTGTTTAGAGATA  77
naive T-cells    AGTTTAGGTTATTTTTTTTATATTTTTGTTAGTTTTTTGTTTAGAGATA  80
Monocytes        AGTTTAGGTTATTTTTTTTATATTTTTGTTAGTTTTTTGTTTAGAGATA  73
AMP1406 Ref-Seq  AGTTTAGGTTATTTTTTTTATATTTTTGTTAGTTTTTTGTTTAGAGATA  96
                 *************************************************

Granulocytes     GAGTAATTTATATCGTTTTTTTTTATTTTATTTTTAGTTTATTTTTATT  122
NK-Cells         GAGTAATTTATATCGTTTTTTTTTATTTTATTTTTAGTTTATTTTTATT  123
mem. T-cells     GAGTAATTTATATTGTTTTTTTTTATTTTATTTTTAGTTTATTTTTATT  130
naive CTL        GAGTAATTTATATTGTTTTTTTTTATTTTATTTTTAGTTTATTTTTATT  131
mem. CTL         GAGTAATTTATATTGTTTTTTTTTATTTTATTTTTAGTTTATTTTTATT  127
naive T-cells    GAGTAATTTATATTGTTTTTTTTTATTTTATTTTTAGTTTATTTTTATT  130
Monocytes        GAGTAATTTATATCGTTTTTTTTTATTTTATTTTTAGTTTATTTTTATT  123
AMP1406 Ref-Seq  GAGTAATTTATATCGTTTTTTTTTATTTTATTTTTAGTTTATTTTTATT  146
                 ************ ************************************

Granulocytes     TTGAAAATTTTTTATTATTAACGGTAGAAAGTAGAGAAGTAGATATTTTT  172
NK-Cells         TTGAAAATTTTTTATTATTAACGGTAGAAAGTAGAGAAGTAGATATTTTT  173
mem. T-cells     TTGAAAATTTTTTATTATTAATGGTAGAAAGTAGAGAAGTAGATATTTTT  180
naive CTL        TTGAAAATTTTTTATTATTAATGGTAGAAAGTAGAGAAGTAGATATTTTT  181
mem. CTL         TTGAAAATTTTTTATTATTAATGGTAGAAAGTAGAGAAGTAGATATTTTT  177
naive T-cells    TTGAAAATTTTTTATTATTAATGGTAGAAAGTAGAGAAGTAGATATTTTT  180
Monocytes        TTGAAAATTTTTTATTATTAACGGTAGAAAGTAGAGAAGTAGATATTTTT  173
AMP1406 Ref-Seq  TTGAAAATTTTTTATTATTAACGGTAGAAAGTAGAGAAGTAGATATTTTT  196
                 ********************* ****************************

Granulocytes     TAGTTTTTTTTTATTTTTTTTTTCCGGTTTTTGGATTAATTAAGGGG  222
NK-Cells         TAGTTTTTTTTTATTTTTTTTTTCGGTTTTTGGATTTATTTAGGGG  223
mem. T-cells     TAGTTTTTTTTTATTTTTTTTTTTGGGTTTTTGGAATTTATTTGGGGG  230
naive CTL        TAGTTTTTTTTTATTTTTTTTTTTGGGTTTTTGGAATTAATTAAGGGG  231
mem. CTL         TAGTTTTTTTTTATTTTTTTTTTGGGTTTTTGGAATTAATTGGGGGG  227
naive T-cells    TAGTTTTTTTTTATTTTTTTTTTTGGGTTTTTGGAATTAATTAAGGGG  230
Monocytes        TAGTTTTTTTTTATTTTTTTTTTCCGGAATTTGTGAGTTAGTAGGGGG  223
AMP1406 Ref-Seq  TAGTTTTTTTTTATTTTTTTTTTCGGTATTTGTGAGTTAGTTAGGGG  246
                 *********************   **   ****  *   *  * ****

Granulocytes     GGGGTATTTTTTTTTAGGTTGAAATTCCGGGGATTGGGTTTTATTTATG  272
NK-Cells         GGGGTGTTTTTTTTTGGGTTGATAGTTCGGGGATTTGGTTTTATTTATG  273
mem. T-cells     GGGGTGTTTTTTTTTGGGTTGATATTTGGGGGATTGGGTTTTTTAATG  280
naive CTL        GGGGAATTTTTTTTTAGGTTGAAATTTGGGGGATTGGGTTTTATTTTTG  281
```

FIG. 3A

```
mem. CTL          GGGGAATTTTTTTTTAGGTGGAAATTTGGGGGATTGGGTTTTATTTATG 277
naive T-cells     GGGGAATTTTTTTTAAGGTGGAAAGTTGGGGGATTGGGTTTTATTTATG 280
Monocytes         AGGGTAGTTTTTATTTAGGTTGATAGTTCGGTGATTTGGTTTAATTTATT 273
AMP1406 Ref-Seq   AGGGTAGTTTTTATTTAGGTTGATAGTTCGGTGATTTGGTTTTATTTATT 296
                  ***  ***** **  *** **  *   **  **** *****  **   *

Granulocytes      GGAGAATTTCCTTGGGG-AAAGGAAAAAAAAACC--TTTTTTTTTGGGTT 319
NK-Cells          GGAGGATTTCCGTGGGG-AAAGGAAAAAAAAACC--TTTTTTTTTGGGTT 320
mem. T-cells      GGAGGATTTTTGTGGGG-AAAGGAAATAAAATTT--TTTTTTTTTGGGTT 327
naive CTL         GGAGGATTTTTGTGGGG-AAAGGAAAAAAATTTT--TTTTTTTTTGGGTT 328
mem. CTL          GGAGAATTTTTGTGGGG-AAAGGAAATAAATTTT--TTTTTTTTTGGGTT 324
naive T-cells     GGAGGATTTTTGTGGGG-AAAGGAAAAAAATTTT--TTTTTTTTTGGGTT 327
Monocytes         GAATGAGTTTCGTTGGGGAGATGAAATATAGTACGGTTTTTTTTTGGTTT 323
AMP1406 Ref-Seq   GGATGAGTTTCGTTGGG-AGATGGAATATAGTACG-TTTTTTTTTGGTTT 344
                  *  *  *  **       *  ***  *  *   **    **********  **

Granulocytes      GGGTTTGGGTTATTTTTTTTCCGAAGGG---AAAGGTTTTTTAAGGGGGG 366
NK-Cells          GGGTTTGGGTTATTTTTTTTCCGAAGGG---AAAGGTTTTTTAAGGGGGG 367
mem. T-cells      G------------------------------------------------- 328
naive CTL         GGGTTTGGGTTATTTTTTTTTGGAAGGG---AAGGGTTTTTTTGGGGGGG 375
mem. CTL          GGGTTTGGGTTTTTTTTTTTTGGGAGGG---AAGGGTTTTTTTGGGGGGG 371
naive T-cells     GGGTTTGGGTTTTTTTTTTTTGGAAGGG---AAGGGTTTTTTTGGGGGGG 374
Monocytes         GGGTATGGGTATTTTTTTTTCGGAAAGGGTAAAGGGTATTTTAGGTGGGG 373
AMP1406 Ref-Seq   GGTATTGGTTATTTTTTTTTCGTAAGGT---AAGGTTATTTTAGGTGGGT 391
                  *

Granulocytes      --GGGGGAAAGGGTTTTG-------------------------------- 382
(SEQ ID NO:66)
NK-Cells          --GGGGGAAAGGGTTTTAAAAGGAAA------------------------ 391
(SEQ ID NO:46)
mem. T-cells      --------------------------------------------------
(SEQ ID NO:47)
naive CTL         ---GGGGGAAGGGGTT---------------------------------- 388
(SEQ ID NO:48)
mem. CTL          --GGGGGGAGGGGTTTAAAGGAATTTTTTGGG------------------ 401
(SEQ ID NO:49)
naive T-cells     --GGGGGAAGGGGTT----------------------------------- 387
(SEQ ID NO:50)
Monocytes         TGGGGGAAAGGGATTTTGGAGAGGGATTATATTGATGGGGAGTGAAGGTT 423
(SEQ ID NO:51)
AMP1406 Ref-Seq   --GGGGGAAGGGATTT--GAGAGGGATATTATTGATGGG-AGTGAGGTTT 436
(SEQ ID NO:67)
```

FIG. 3B (Ref-Seq is SEQ ID No. 7)
```
Monocytes       -----------------------TATCCCTCTCA--AATCCCTTCCCCCA 25
NK-Cells        -----------------------TATCCCTCTCA--AATCCCTTCCCCCA 25
AMP1406 Ref-Seq ATAAACCTCACTCCCATCAATAATATCCCTCTCA--AATCCCTTCCCCCA 48
Granulocytes    ----------------------GTATCCCTCTCA--AATCCCTTCCCCCA 26
mem. T-cells    ----------------------GCCATCTTACCCA-CAACCCTTAACCCCA 28
naive CTL       ----------------------GCCATCTTACCCA-CAACCCT-AACCCCA 27
mem. CTL        ---------------------TATATCCTACTCAACATCCCTATCCCCCA 29
naive T-cells   --------------------------CATCCCTCTCT--AATCCCTTCCCCCA 25
                                          ***   *  *   *  **    *****

Monocytes       CCCACCTAAAATAACCTTACCTTACGAAAAAAAAATAACCAATACCAAAC 75
NK-Cells        CCCACCTAAAATAACCTTACCTTACGAAAAAAAAATAACCAATACCAAAC 75
AMP1406 Ref-Seq CCCACCTAAAATAACCTTACCTTACGAAAAAAAAATAACCAATACCAAAC 98
Granulocytes    CCCACCTAAAATAACCTTACCTTACGAAAAAAAAATAACCAATACCAAAC 76
mem. T-cells    CCCACCTAAAATAACCTTACCTTACAAAAAAAAAATAACCAATACCAAAC 78
naive CTL       CCCACCTAAAATAACCTTACCTTACAAAAAAAAAATAACCAATACCAAAC 77
mem. CTL        CCCACCTAAAATAACCTTACCTTACAAAAAAAAAATAACCAATACCAAAC 79
naive T-cells   CCCACCTAAAATAACCTTACCTTACAAAAAAAAAATAACCAATACCAAAC 75
                ****************************  ********************

Monocytes       CAAAAAAAAACGTACTATATTCCATCTCCCAACGAAACTCATCCAATAAA 125
NK-Cells        CAAAAAAAAACGTACTATATTCCATCTCCCAACGAAACTCATCCAATAAA 125
AMP1406 Ref-Seq CAAAAAAAAACGTACTATATTCCATCTCCCAACGAAACTCATCCAATAAA 148
Granulocytes    CAAAAAAAAACGTACTATATTCCATCTCCCAACGAAACTCATCCAATAAA 126
mem. T-cells    CAAAAAAAAACATACTATATTCCATCTCCCAACAAAACTCATCCAATAAA 128
naive CTL       CAAAAAAAAACATACTATATTCCATCTCCCAACAAAACTCATCCAATAAA 127
mem. CTL        CAAAAAAAAACATACTATATTCCATCTCCCAACAAAACTCATCCAATAAA 129
naive T-cells   CAAAAAAAAACATACTATATTCCATCTCCCAACAAAACTCATCCAATAAA 125
                *********** ********************* ****************

Monocytes       TAAAACCAAATCACCGAACTATCAACCTAAATAAAAACTACCCTCCCCTA 175
NK-Cells        TAAAACCAAATCACCGAACTATCAACCTAAATAAAAACTACCCTCCCCTA 175
AMP1406 Ref-Seq TAAAACCAAATCACCGAACTATCAACCTAAATAAAAACTACCCTCCCCTA 198
Granulocytes    TAAAACCAAATCACCGAACTATCAACCTAAATAAAAACTACCCTCCCCTA 176
mem. T-cells    TAAAACCAAATCACCAAACTATCAACCTAAATAAAAACTACCCTCCCCTA 178
naive CTL       TAAAACCAAATCACCAAACTATCAACCTAAATAAAAACTACCCTCCCCTA 177
mem. CTL        TAAAACCAAATCACCAAACTATCAACCTAAATAAAAACTACCCTCCCCTA 179
naive T-cells   TAAAACCAAATCACCAAACTATCAACCTAAATAAAAACTACCCTCCCCTA 175
                *************** **********************************

Monocytes       ACTAACTCACAAATACCGAAAAAAAAAAAATAAAAAAAAACCTAAAAAAT 225
NK-Cells        ACTAACTCACAAATACCGAAAAAAAAAAAATAAAAAAAAACTAAAAAAT 225
AMP1406 Ref-Seq ACTAACTCACAAATACCGAAAAAAAAAAAATAAAAAAAAACTAAAAAAT 248
Granulocytes    ACTAACTCACAAATACCGAAAAAAAAAAAATAAAAAAAAACTAAAAAAT 226
mem. T-cells    ACTAACTCACAAATCCCAAAAAAAAAAAAATAAAAAAAAACCTAAAAATT 228
naive CTL       ACTAACTCACAAATCCCAAAAAAAAAAAAATAAAAAAAAACCTAAAAATT 227
mem. CTL        ACTAACTCACAAATCCCAAAAAAAAAAAAAAAAAAAAAAACCTAAAAATT 229
naive T-cells   ACTAACTCACAAATCCCAAAAAAAAAAAAATAAAAAAAAACCTAAAAAAT 225
                ************** **  **********  *********  *******  *

Monocytes       TTTTCCTTCTTTCCTTTCTCCCGTTAAAAAAAAAAAATTTTCAAAAAAAA 275
NK-Cells        TTTTCCTTCTTTCCTTTCTCCCGTTAAAAAAAAAAAATTTTCAAAAAAAA 275
AMP1406 Ref-Seq ATCTACTTCTCTACTTTCTACCGTTAATAATAAAAAATTTTCAAAATAAA 298
Granulocytes    TTTTTTTTTTTTTTTTTTCCCGTTAATAAAAAAAATTTTTAAAAATAAA 276
```

FIG. 4A

```
mem. T-cells      TTTTTTTTCTTTCTTTTCCCCCTTTAAAAAAAAAATTTTTAAAAAAAAA 278
naive CTL         TTCTCTTTCTCTCTTTTCCCCCTTAAAAAAAAAAATTTTTAAAAAAAAA 277
mem. CTL          TTTTCTTTTTTTCTTTTCCCCCTTAAAAAAAAAAAATTTTTAAAAAAAAA 279
naive T-cells     TTTTCTTTTTTTCTTTTCCCCCTTAAAAAAAAAAAATTTTTAAAAAAAAA 275
                   *  *   **  *  *  ***    **  ** ** ***** **** **** ***

Monocytes         AATAACCTAAAAAAAAAAAAAAAAAAAACCGTTTTAATTTCCTTTTTTTT 325
NK-Cells          AATAACCTAAAAATAAAAAAAAAAAAAACCGTTTTAATTTCCTTTTTTTT 325
AMP1406 Ref-Seq   AATAAACTAAAAATAAATAAAAAAAAAACGATATAAATTACTCTATCTC 348
Granulocytes      AATAACCTAAAAATAAATAAAAAAAAACCGTTTTAATTTCCTTTTTTTT 326
mem. T-cells      AAAAACCTAAAAAAAAAAAAAAAAAAAACCATTTTAATTTCTTTTTTTTT 328
naive CTL         AAAAACCTAAAAAAAAAAAAAAAAAAAACCATTTTAATTTCTTTTTTTTT 327
mem. CTL          AAAAACCTAAAAAAAAAAAAAAAAAAAACCTTTTTAATTTCTCCTTTCTT 329
naive T-cells     ATTAACTTAAAATAAAAAAAAAAAAAAACCATTTTAATTTTTTTTTTTTT 325
                   *  **  ***** ****  ********* *  * ***  **       * * *

Monocytes         TAACCAAAAAATTAACAAAAAATTTAAAAAAAATACCCAAAATTTTACCG 375
NK-Cells          TAACCAAAAACTTAACAAAAAATTTAAAAAAAAACCCTAACTTTTACCG 375
AMP1406 Ref-Seq   TAAACAAAAAACTAACAAAAAATATAAAAAAAAATAACCTAAACTTTAACG 398
Granulocytes      TAACCAAAAACTTACCAAAAAATTTAAAAAAAATACCCTAACTTTTACCG 376
mem. T-cells      TAACCAAAAACTTACAAAAAATTTTAAAAAAAA-ACCCCAAACTTTAACC 377
naive CTL         TAACAAAAAACTTACAAAAAATTTTAAAAAAAA-AACCCAAACTTTTACC 376
mem. CTL          TAACCAAAAACTTACCAAAAATTTTAAAAAAAA-TCCCCAAATTTTACC 378
naive T-cells     TAACAAAAAACTTACCAAAATTTTAAAAAAAA-ACCCCAAACTTTTACC 374
                   ***  ***** **  ***** * * ********   **  **   ***   *

Monocytes         CCCCTTTAAACAATCCACCCACTTTTCCCCACACCTAAAAA-  416 (SEQ ID
NO:52)
NK-Cells          CCCCTTTAAACAATCCACCCCCTTTTCCCCCCACCCTAAAA-  416 (SEQ ID
NO:53)
AMP1406 Ref-Seq   TCCCTATTAACAATACAACCACATTTACACACAACCTAAA--438 (SEQ ID
NO:7)
Granulocytes      CCCCTTTAAAAAAACCACCCCCTTTTCCCCCCACCCAAAAAA 418 (SEQ ID
NO:54)
mem. T-cells      CCCCTTTTAAAAAAACCCCCCCCTTTTCCCCCCCCCCAAAAA 419 (SEQ ID
NO:55)
naive CTL         CCCCTTTTAAAAAAACCCCCCCCTTTTCCCCCCCCCCAAAAA 418 (SEQ ID
NO:56)
mem. CTL          CCCCTTTTAAAAAAACCACCCCTTTTTCCCCCCCCCCAAAA-  419 (SEQ ID
NO:57)
naive T-cells     CCCCTTTTAAAAAAACCCCCCCCTTTTTCCCCCCCCCCAAAAA 416 (SEQ ID
NO:58)
                   ****  * **  **   * **   * *   *  *      ***
```

FIG. 4B (Ref-Seq is SEQ ID No. 8)

```
naive Th-cells      ------------------------CTATAACAACAACAACTAACAACAAATAA  29
mem. Th-cells       ------------------------CTATAACAACAACAACTAACAACAAATAA  29
mem. CTL            ------------------------CTATAACAACAACAACTAACAACAAATAA  29
naive CTL           ------------------------GTATAACAACAACAACTAACAACAAATAA  29
AMP1408 Ref-Seq     AATCCCTCCTAAATTCATTACCTACAACAACAACAACTAACAACAAATAA      50
Granulocytes        -----------------------TATAACAACAACAACTAACAACAAATAA     28
Monocytes           -----------------------TATAACAACAACAACTAACAACAAATAA     28
NK-Cells            -----------------------GATAACAACAACAACTAACAACAAATAA     28
                                           * ************************** naive Th-cells      CAACTAACTACAATCCTAACAACTAATAACAAAAACATTTATCTCCCTCA      79
mem. Th-cells       CAACTAACTACAATCCTAACAACTAATAACAAAAACATTTATCTCCCTCA      79
mem. CTL            CAACTAACTACAATCCTAACAACTAATAACAAAAACATTTATCTCCCTCA      79
naive CTL           CAACTAACTACAATCCTAACAACTAATAACAAAAACATTTATCTCCCTCA      79
AMP1408 Ref-Seq     CAACTAACTACGATCCTAACAACTAATAACAAAAACATTTATCTCCCTCA     100
Granulocytes        CAACTAACTACGATCCTAACAACTAATAACAAAAACATTTATCTCCCTCA      78
Monocytes           CAACTAACTACGATCCTAACAACTAATAACAAAAACATTTATCTCCCTCA      78
NK-Cells            CAACTAACTACGATCCTAACAACTAATAACAAAAACATTTATCTCCCTCA      78
                    ********* ************************************ naive Th-cells      TAAAAAAACAATCCCAAAACCATCTCCCACCCAACATCCATTACAATTCC     129
mem. Th-cells       TAAAAAAACAATCCCAAAACCATCTCCCACCCAACATCCATTACAATTCC     129
mem. CTL            TAAAAAAACAATCCCAAAACCATCTCCCACCCAACATCCATTACAATTCC     129
naive CTL           TAAAAAAACAATCCCAAAACCATCTCCCACCCAACATCCATTACAATTCC     129
AMP1408 Ref-Seq     TAAAAAAACGATCCCAAAACCATCTCCCACCCAACATCCATTACGATTCC     150
Granulocytes        TAAAAAAACGATCCCAAAACCATCTCCCACCCAACATCCATTACGATTCC     128
Monocytes           TAAAAAAACGATCCCAAAACCATCTCCCACCCAACATCCATTACGATTCC     128
NK-Cells            TAAAAAAACGATCCCAAAACCATCTCCCACCCAACATCCATTACGATTCC     128
                    ******* ****************************** *** naive Th-cells      CTATACAAAATAAATCTCTAAATAAAAATCCAACACTCTCTCCCTCTTCT     179
mem. Th-cells       CTATACAAAATAAATCTCTAAATAAAAATCCAACACTCTCTCCCTCTTCT     179
mem. CTL            CTATACAAAATAAATCTCTAAATAAAAATCCAACACTCTCTCCCTCTTCT     179
naive CTL           CTATACAAAATAAATCTCTAAATAAAAATCCAACACTCTCTCCCTCTTCT     179
AMP1408 Ref-Seq     CTATACAAAATAAATCTCTAAATAAAAATCCAACACTCTCTCCCTCTTCT     200
Granulocytes        CTATACAAAATAAATCTCTAAATAAAAATCCAACACTCTCTCCCTCTTCT     178
Monocytes           CTATACAAAATAAATCTCTAAATAAAAATCCAACACTCTCTCCCTCTTCT     178
NK-Cells            CTATACAAAATAAATCTCTAAATAAAAATCCAACACTCTCTCCCTCTTCT     178
                    ************************************************** naive Th- cells     TCCCCACCACCTTCACCCTCCTTAACAAAAAAACAAAAAACATCTACACC     229
mem. Th-cells       TCCCCACCACCTTCACCCTCCTTAACAAAAAAACAAAAAACATCTACACC     229
mem. CTL            TCCCCACCACCTTCACCCTCCTTAACAAAAAAACAAAAAACATCTACACC     229
naive CTL           TCCCCACCACCTTCACCCTCCTTAACAAAAAAACAAAAAACATCTACACC     229
AMP1408 Ref-Seq     TCCCCACCACCTTCACCCTCCTTAACGAAAAAACAAAAAACATCTACACC     250
Granulocytes        TCCCCACCACCTTCACCCTCCTTAACGAAAAAACAAAAAACATCTACACC     228
Monocytes           TCCCCACCACCTTCACCCTCCTTAACGAAAAAACAAAAAACATCTACACC     228
NK-Cells            TCCCCACCACCTTCACCCTCCTTAACGAAAAAACAAAAAACATCTACACC     228
                    ************************ ********************* naive Th-cells      TACAACCCTACTAAAACCCCTACTACTCACACTTACAACAAAAAATAAAA     279
mem. Th-cells       TACAACCCTACTAAAACCCCTACTACTCACACTTACAACAAAAAATAAAA     279
mem. CTL            TACAACCCTACTAAAACCCCTACTACTCACACTTACAACAAAAAATAAAA     279
naive CTL           TACAACCCTACTAAAACCCCTACTACTCACACTTACAACAAAAAATAAAA     279
```

FIG. 5A

```
AMP1408 Ref-Seq    TACAACCCTACTAAAACCCCTACTACTCACACTTACAACAAAAAATAAAA 300
Granulocytes       TACAACCCTACTAAAACCCCTACTACTCACACTTACAACAAAAAATAAAA 278
Monocytes          TACAACCCTACTAAAACCCCTACTACTCACACTTACAACAAAAAATAAAA 278
NK-Cells           TACAACCCTACTAAAACCCCTACTACTCACACTTACAACAAAAAATAAAA 278
                   ************************************************** naive Th-cells     ACTCTAAATTCTTACCTTCTCTCAAAAACCCCAACCCCAACAATAATAAA 329
mem. Th-cells      ACTCTAAATTCTTACCTTCTCTCAAAAACCCCAACCCCAACAATAATAAA 329
mem. CTL           ACTCTAAATTCTTACCTTCTCTCAAAAACCCCAACCCCAACAATAATAAA 329
naive CTL          ACTCTAAATTCTTACCTTCTCTCAAAAACCCCAACCCCAACAATAATAAA 329
AMP1408 Ref-Seq    ACTCTAAATTCTTACCTTCTCTCAAAAACCCCAACCCCAACAATAATAAA 350
Granulocytes       ACTCTAAATTCTTACCTTCTCTCAAAAACCCCAACCCCAACAATAATAAA 328
Monocytes          ACTCTAAATTCTTACCTTCTCTCAAAAACCCCAACCCCAACAATAATAAA 328
NK-Cells           ACTCTAAATTCTTACCTTCTCTCAAAAACCCCAACCCCAACAATAATAAA 328
                   ************************************************** naive Th-cells     TAAAACCAATCTAACTACTACACAAACTAACTAACTAACTAACTACAAAA 379
mem. Th-cells      TAAAACCAATCTAACTACTACACAAACTAACTAACTAACTAACTACAAAA 379
mem. CTL           TAAAACCAATCTAACTACTACACAAACTAACTAACTAACTAACTACTAAA 379
naive CTL          TAAAACCAATCTAACTACTACACAAACTAACTAACTAACTAACTACTAAA 379
AMP1408 Ref-Seq    TAAAACCAATCTAACTACTACACAAACTAACTAACTAACTAACTACTAAA 400
Granulocytes       TAAAACCAATCTAACTACTACACAAACTAACTAACTAACTAACTACTAAA 378
Monocytes          TAAAACCAATCTAACTACTACACAAACTAACTAACTAACTAACTACTAAA 378
NK-Cells           TAAAACCAATCTAACTACTACACAAACTAACTAACTAACTACTAACAACT 378
                   **************************************    * naive Th-cells     AACTACTCCTTACTTTTACCAAAAAACACAAACTAACATAAAACAAAAAA 429
mem. Th-cells      AACTACTCCTTACTTTTACCAAAAAACACAAACTAACATAAAACAAAAAA 429
mem. CTL           AACTACTCCTCACTTTTACCAAAAAACACAAACTAACATAAAACAAAAAA 429
naive CTL          AACTACTCCACACTTTTACCAAAAAACACAAACTAACATAAAACAAAAAA 429
AMP1408 Ref-Seq    AACTACTCCACGCTTTTACCGAAAAACAAAAACTAACATAAAACAAAAAA 450
Granulocytes       AACTACTGCACGCTTTTACCGAAAAACACAAACTAACATAAAACAAAAAA 428
Monocytes          AACTACTGCACGCTTTGACCGAAAAACAAAAACTAACATAAAACAAAAAA 428
NK-Cells           ACTTACTGCTTGCTCCGACCAACAAACACTAACTTAAAACAAAAAAAAAA 428
                   *  **** *       *   *  ***   ** *   * **** naive Th cells     AAAACCTAT------------- 438  (SEQ ID NO:59)
mem. Th-cells      AAAACCTATCTTT--------- 442  (SEQ ID NO:60)
mem. CTL           AAAACCTATCTTTCCT------ 445  (SEQ ID NO:61)
naive CTL          AAAACCTA-------------- 437  (SEQ ID NO:62)
AMP1408 Ref-Seq    AAAACCTAACTATCCTCATCCT 472  (SEQ ID NO:8)
Granulocytes       AAAACCTATCTTTCCCAACCT  450  (SEQ ID NO:63)
Monocytes          AAAACCTATCTTTCCCCT---- 446  (SEQ ID NO:64)
NK-Cells           CAAACCTATCTTTCTCCCAA-- 448  (SEQ ID NO:65)
                   *******
```

FIG. 5B (SEQ ID NO: 1)
AGATGACATCTATTGAAAATATCCCTGTCTCAGCCAGGTGCAGTGGCTCATGCCTCTAATCCCAGCACTTTTGGAGGC
TGAGTGAGTGGATCATTTGAGGTCAAGAGTTCGAGACCAGCCTGGCCAACATGATGAAACCCTGTCTCTACTAAAAAT
ACAAAAATTAGCTGAACTTGGTGACACATGCTTGCAATCCCAGCTACTCAGGAGGCTGAGGCAGGAGAATCACTTGAC
TCCAGGAGACAGAGGTTGCAGTAAGCCAAGATCATGCCACAGCACTCCAGCCTGAGCAACAGAGCAAGACTCCATCTC
AAAAAAAAAAAAAATCCCTGTCTCAAACTCCTGCTTTCCAGGTAGATGGAGCGGGATAATGTGCTTTAATTGGTGAAG
GGTTTCTGATCCCCATTTATCATGCAGAAGGCAGGAGCAAGCCAGAGACAGGTCCTGGCGAAAGGAAGCTAAAATGGT
GCCTTTGATACAGGGGAAAGGGATACGAAAGGGGCTTAGGTGAGACCTCCTTACAGCTAGTGGCACCTGGTCAGCAGG
GCCGTAGAGTTGAGGCCATCCCCTTAGCAGCAGTGGGACTTTGTTACACACACCCTCTGAGTCTTGGTGAGAAACTAG
TCCCAGGGCCCCTTGTTGTCTCTGCCACTCCCATTCATGACATCATGGAAACTTCTGTGCGGCTGGGCTCCTGAACAC
AGCAGCCTGCCCTCGGCTGGATGAGGCAGCCAAAACCCTAAAAGGGTTGTGATAGGGACTGGAGTCAACAAGTAGCTG
TGGGAACGTGGTGGCCGCAGACCCTTCACCCAGGGAGCCCTGTGGGCTAGAAACACCAGACAGCCAGGATGTGGCGAGA
GACTGCCCAACACACTGTCTGTGTGAGGCAGAGGAAGGAAGGAGATGAAGGAAGAAACAGGTAGGTAGGAGGGCGAGA
TCCCAAGCAAGTCAGGACAACTCCCACGCCTTGCCCAGGAGCCTTAAGAAGCCCAGGCACCTGCT<u>GAGTGAAAGAGGA
TATATTTATTGGCTGAGCAAGAAGGGAAGGTACAGTTGGTAATGGCTGCTTCTAGAAGCCACCAGTCTCAGGTTCACT
TGTTCCGAGCCCAGTTTCCTCCAAGGTGGCTGTACTGAGCATCATCTCGATCTCGGAGGGGCTAAGAGAGGAGAAGAG
AAAACGGTCAGGAGGCAGGGTTAGAACTCTTCAAGGAAGGGCCCCAGCAGGCCCTGACGATGAGAGCTCCTGCCTGAC
CTCTCCAGTCACACCCAGCAATGAACTCCCCAGTAGGACCCTTCCCACGTGCAAACAGCATTCAGTGTGAGCCTCTCT
ATCCCCACTTACCCTCCCTTCATTCCTGCCTCCTTCCCCTCAACGCTCACCTGATAGACCTGGTCATTCCTCAACAGA
GCTTGTGTGTCGGCAGCTAGAAGAACCAGAGAGAGACATCAATGGCCTAGCAGATGGGACTGTGAGATCCACCCTCCC</u>
ACACCCTCAGAAGTCTGCATGAGTGATATGAACACACAAGTTCTTTCAACAGTCAAAGTTCTAGGAGTCTTTAGGAGA
TTGCAAGAGTAACTCCCAGCTGAGACTAAACCTACCACCAGCCCCATTCCTTAGCTGGTGCATAAGCTCACTGGTACA
CACACACACACACACACACACACACACAAACACACTCTCATGCTCTGCTCTTCCACTAAC<u>CCCCAGACAGCCTTCC
AGTCTCATGTCCAGCAAAGCAGAAGACTCCCAAAGCAAGGAGCAGAGTGGCAATGACATCAGTGACAATGATGCCAGC
CACGGTGGCTGGATCCAGCTCCACACAGCTCTGGCACACTGTGGGGAAGGGAGGAGAGAGGAGAGGTTGAGAGCCTT</u>
TAAGATCAGGGAACCATCCTCTGCCTCCTAGGGCAACCCTTAGATCTCTTATGCCAAAACCCAAACTTCAATAAGACC
CTGGGAGAAAGGCCTGGTGATGGGCTTGCCACACCTTCCTCCACCCTGCATCCTAAGGAATCCCTGGGAAGAGCCAAG
AAGTAATCTCAGCTTTTGGGACCTTGAACAAGGTGGTGGGCCAAACCTCTCACCCAACCAAGGCTGCAGTAACATGAC
CCCTACTGCTCTGTCTTGCTGAGTTAAGCTCTCTCTTCCACTTTGAAGGTCCCCAAATCTGGCTTGTACCATTACAAT
AGTGACCTCACTTTGTTTAGAGAACAGATGGGTTCACCATATCCCTCTCTAGCCAGAAAGTTCTCACATCCAGAAGCC
CTATCCATTCCAACCCAAAGGGTTCAGGAAGCACGTACTTCGATAATGAACTTGCACGGTAGATTCTTTGTCCTTGTA
<u>TATATCTGTCCCATTACACCTATATATTCCTCGTGGGTCCAGGATGCGTTTTCCCAGGTCCAGTCTTGTAATGTCTGA
GAGCAGTGTTCCCACCGTTCCCTCTACCCATGTGATGCTGGTATTGCAATTCACAAACACTCTGTCCTCAAGTTCCTC
TATAGGTATCTTGAAGGGGCTCACTAAAGGGGAAAAAATATCACAGTTGGAGACAGCTCTTTGATCTGCACCAAGCCC
TTTGTTCTGCGGAAGCTCATACTTAACAGAGACCATTTTCCTGGTCCAGGACAGTTTATGGCTTCCATCAAGAGAGAC</u>
AGAAGTCACAAGAAAAAGCCTTCAGAAAGTTCCCCACCAACTGCAGGGGTCAAGGGGGACATGAGGATGCCATTCAAG
CAGAGGACAGGTCTTGGGGCCTTGGTGCAAAAGAGGACCCCTCAGAGCAGGATTGACCCAAGCACCTTCCTGGAAATG
AATCCAGACCACTGATGAGGAGTAGGGGGAGCACGGACCACTGAAGCACCTGGAAGATGTGGAAAGACAGAAGAACAT
TCCTCGATTGGAAATGTCTGCATTTTTCTTCAAGGAAACATCTAATTCCACTTCCCAGCCATCTACAACACTCCCAC
TTCAGCTTCTTATCCTCATCCTTCCTCATTGCCCCTGCTCCATTGACAACCAAGAAAGCGGGGCTCTCAACACTGAAG
CCTTTCCCAGGGCCAGGGATGGCTGTGGGTGGAGACCAGCTGGTTTACCAGCCCCTGAATTATCAGCCAAGTGGTCCA
GAACGGGACCAGGGCAAATCCCATGTACAGTTTTCCACCCTTGGTTAGAAGGAGGAGAACAGGAAAAAAATTTTATTG
AATCCATCCCTAGAGCTCCTCACAAGTCAAGTCTTGTGGGAGACTTTTAGGGCTGGAGGTGAGTGCAGCAACATTCCA
GATGCAGTGAGTTCCTCTGACAGCCTGAGCACATCTCCACAGGCCACAGAGGCACTACAGTCTATGCCTCAAACACA
GGGAAAAGTGGAGGCTACATTCATTCATCCTGGGCTTCACACTAAGTCCCAAATTTGGATACAAGAGCATCTTCTAGA
AAACCCTGAAACAGCTGTTGCTCACACTTCTGAAGCAGGTTGGAAGTATATGCATGTATCCTCAGGGAGACACATGCA
CATCAAATGCTTCACGTCCTACAGTCGCGTCCTCTTCAGGGATCTGTCTCCAGTGGAAATCCTGAGTGCCCTAGTGCA
GCCAACTATTAGGTGACCATTGGACCCAGTTTGCTTAGTGTTGAAGGGGTTCCTCGGACATGGGACTTTCCATTTTAA
AACTGAAATTGGCAAACTGAGATGAGTTAAAATCCTACCATGTAACAACCCCTCAAATCTTCCCTCCGTCCTGCTCAA
CCTAAAGTTAACTTCTCTTAAAGCATTCACATAAGTGCTAGGACATGCCTCCAGGGATGACATAATCATGGCCAAACA
AACAAGAGTCCTGATTCCAGAGGCCATCAGGCCTAAAAGGAGTAGTGCAGGAAGCTGTGCTCCCATGGCCAGTCCCAG
ATTCAGGTACATACGTACTGAGCTATTTTCTGCAGATCTCTGGCCTAAGGCCTTCTGAGAGACATTCTAGGCCCACAT

FIG. 6A

```
GCACCCATGGCTGGAGTCAGTCAAAGCCAAGAGCCTGTTTCCCAGACTCTATGCTACATCCTGCCCCTGCCCTCCTGA
CACCCCTGGGGTGCCTGGTGAACTGAAGCTAGCACCGAGAAGCACTTTTTTTTTTTTGAGATAAGGTCTCACAGGT
TGCCTAGGTTGGAGGGCAGTGGCATGATCACAGCTCACTGAAGCCTTGAAATCCCGGGCTCAAGTGACCCTCCTGCCT
CAGCCTCTCAAATAGCTGGGACTACAGTTGTGCACCACCATGCCTGGCTAATTCTTTTGTTTTTTGTAAAGATAGAGT
CTCATCATGTTGCTCAGACTGGTCTCAAACTCCTGGCCTCAAAGGATCCTCCCACTTCGGCCTCCCAAAGCTCTGGGA
TTACTGGTGTGAGCCACCGTGCCTGGCAAGAAACACTTTCAAGTGGGCCTCACTCCCATCAGTAATGTCCCTCTCAGG
TCCCTTCCCCCACCCACCTGGAGTAGCCTTACCTTGCGAGAGAAGGGTAGCCAGTACCAGGCCAGAGAGAAACGTGCT
ATGTTCCATCTCCCAGCGGAACTCATCCAGTAGATAAAGCCAGGTCACCGAACTATCAGCCTGGGTGAGAGCTGCCCT
CCCCTAGCTGACTCACAGGTACCGGAAAGAGGAGAGTGGGGGAGGAACTAGAAGATGTCTGCTTCTCTGCTTTCTGCC
GTTGATGGTGGGAAATTTTCAGAGTGGGGGTGGGCTAGGGGTAGGGTAGGAAGGAAGCGGTGTAAATTGCTCTATCTC
TGAGCAGGGAGCTGGCAGAGAATATGGAAAGGTGGCCTGAACTTTAGCGTCCCTATTGACAATGCAACCACATTTAC
ACACAACCTAAACACTGCCACATCTCGAAGCCCCTTGAGAGAAGCCGTCGGCCCCATAGCCGCAAGCCGTAGCAGCTAG
ATTTCTCATGGAGGCTGATCTTTCTCAGGACCCTTCACTAGGCAGCCAGGGACACCAGATCTAGCAGCTTCTTGTCAG
TGGGAGGTTGGGCTTTAGAGACCCCAGCCAGAGATTTGAATCCTGGGTCCAATACTGCCTACCTGTGGGGCCTGGGCC
AGCCATAAAATTTTTCAGAGTCTTATTCCATTAGTACCATTATTAGGATTCAAACAAGATATTTGCATGGTGCCTCAC
GCATCATATGTGCTCATTAAGGGGTAGTTATTAATAATAATATAATTGACTGACAGGCAATATTGAGCCTCCCGGTGA
GACAAATGGACCTTTTTCCCCTGTGGCCTACGAGGATCTGAAACTCTTCACGCTGCTGCAGTTAGACTGTCACTTACC
TGGGGACAGAGTCATGCCTGTCTTGCTCACTGCTGTATCTTGTGCCTGGCACATAACGGGAGCTCTGCACATTTTTGT
TGGCTCACTGACTGACTGGCTGAGGAGATAGGGGCCTGAGATCCTGGACATTCAGTCCGGGCTCTGGCCCCTGAAAA
TGTGCTGGCCTGTCCTCGGAATTGTTCCACCTATTGCCTTCCAGGCGCCTCTTTCATGATCTCAAAAGAATAGTGAAA
CCAGGTGCCGTGTCTCACGCCTGTAATCCCAACACTTTGGGAGGCTGAGGCAGGTGGATCACAAGGTCAGGAGTTCGA
GACCAGCCTGACCAACAAGGTGAAACCCCGTCTCTACTAAAAATACAAAAATTAGCCGGGCTTGCTGGCACGCACCTG
TAATCTCAGCTACTCAGGAGGCTGAGGCAGGAGAATCGCTTGAACCCCGGAGGTGGAGGTTGCAGTGAGCTGAGATAG
CGCCACTGCACTCCAGCCTGGGCAACAAAGTGAGACTCTGTCTCAAAAAAGAAAAAGAAAAAAAAGTGAAAAAAATT
CCTGAATGAAGGCCTGGACTGAGGTGGCTTTCCATTTGGAGGTCCAGCCCCAAGCATCTGAGAGTCCCTCCTAAATTC
ATTACCTACAGCAACAACAACTAGCAACAAGTAACAACTGGCTACGATCCTAACAACTAATGACAGGGACATTTATCT
CCCTCATGAAGAAACGGTCCCAGGACCATCTCCCACCCAGCATCCATTGCGGTTCCCTGTGCAAGATGAGTCTCTGAG
TGGGAATCCAGCACTCTCTCCCTCTTCTTCCCCACCACCTTCACCCTCCTTAACGGAAAAACAAAAGGCATCTGCACC
TGCAGCCCTGCTGAGGCCCCTGCTGCTCACACTTGCAGCAGAGGGTGGAGGCTCTGGGTTCTTGCCTTCTCTCAAAGG
CCCCAGCCCCAACAGTGATGGGTGGAGCCAGTCTAGCTGCTGCACAGGCTGGCTGGCTGGCTGGCTGCTAAGGGCTGC
TCCACGCTTTTGCCGGAGGACAGAGACTGACATGGAACAGGGGAAGGGCCTGGCTGTCCTCATCCTGGCTATCATTCT
TCTTCAAGGTAAGGGCCTACTAGGGGTCTGGAAGCCTGGGGAAGGGCTCAAGGGAAGAGCCCATCACTAGTGAGACAG
GAATATTGGTATCCCTAACCTTCAGCCTACCTCTGCTGTCACCTTAGAGTTCAAAGAAGGGCAAAATGGAGGCTCTTA
ACTGTTCTCTGCTAGAGAGAAACAGTGTCCCATGGAGGAGAAGGAATCCTTGTCTCTGAAAAATGCAAACAGAGTACT
TAAATGGCTGAAGAGAGGACCCTGTTACCGCCATCTTAGATTTGAATGCAGCCCAAAAGGGCATAGGCCAAGAAACTA
AAAGGAAAAGTATATGTTCCCTACTTCAGAGCTGGGGGCTAGCAGTCGACCTAGGAAATGTCCATTCACTCAGTTGG
GCAGTTGGCCAATTGGTCAACAAAGATGGGTGAGACCCTAATATGTGATATGCCATGAGGAAATAAAAATGAATAAAA
CACTTATGCTCTACAGAACTCATAGTCTCATTGGAGAGATTAGTTTTCATGGTGCCAGACTGAGTGTACAGTATAGTA
TGGGTGCCTGCATGAATACTCCATTGGACTATCCAATAGGAAGTGGATGAACTGGGTTGATGCCTGGAGTCTGGACAT
CCTGGGAAAGTTAAAACCATGGAATTTGCTGAAGTCACACAAGTACTATGTGAGGAAGAGGGAGCTGAAGATGGAACA
GTGAGGGCACCAATTTTAAGGGGCAGTTAGAGAAAAAAAACATTCCAGGAAAGAGATAAAAGGAGAATCAAAGAGCT
GAAATAATCAAATGTATGCACTACCTTGGAAACCAAGAGAGTAGAGAGCTTCTAGAAGAAGAGAATTACCAAGAGTAT
AAAATGTTAAAGAGAGCCCACTAATATAAGAATATATTTAAAAGTTTAAGTCTGCGGGATGTGGCAGAATATGCATCA
TGGGTGATTTAGCACAGTTTCAGCAGGGTATTGTGAGTGGAAGCCAAGTGAAAATTGGTAGAAGGTGAAGGTCAGGT
ATGAGGTCAGCAAGTGTAGACTATTCTTTAAAGACATTTGGATGAGGAGGGAGAAAAGACTGGGTGGTAGGTAGAGGA
GGAAGTAGAGTCTAAGAATAAATGTTTTTGAGGGTGAGAGAAACTTGAGCACATTTCTAGGCTAAAGGAGAAGATGAT
GAGTAGAGCAAGGTCCTGGAGTTGATGGTGGAAGGACAGAGTCAAGAGTGGGTCAAGAGCACAGAGAGGAAGGCAAC
GTTACCCTCTAAGACCAGGAGAAAGGAAGTGCAAACGGCACTGGCCACAAATAGGTTTATAAAGGGAAGGAAGCTAA
AGGAGAAAGGACAATAACAACTTCCGTGTTCTAAAAAATCCAGGTGGGAGGCAATGCCACCTGCTGAAACTGAGCTGG
GTGATGACCGGTTGGGAGACTTGAAGAGGACAGTGAGAGTTTAGAATAGAATTATTTCTGAGAGAAATGCAAGGAAAA
GTCAGGTAAAGACAACACAGGTTGAGGAGCAACTCTCAAGCCTGGGTGAGGTGGCTGCATATCATGGAAAGAGCATTT
GAGTTCAGCAGTAGAAAACCTGAGCTCTGGATCCAGCTTGGACACCAATGAGCTATGTGTACTTGAACAACTCCTCCA
```

FIG. 6B

```
CTGTCTGGGAGTTCTCATGCCAGCCAATCCAGAAATGTGGCAGGGACGGGCATGGTGGCTCATGCCTGTAATCCCAGC
ACTTTGGGAGGTCGAGGCAGGTGGATCACCTGAGGTCAGGAGTTCGAGACCATCCTGGTCAACATGGTGAAACTCTAT
CTCTACTAAAAATATTTTAAAAATTAGTGGGGTGTGGTGGTGGGTGCCTGTAATCCCAGCTACTCAGGAGGCTGAGGC
AGGAGAATTGCTTGAACCCAGGAGATGGAGGTTGCAGTGAGCCAACACGGTGCCACTGCACTCCAGCCTGGGCGACAG
AGTGAGACTCCGTCTCAAAAAACAAAACAAAAAAAAAGAAATGTGGCTATATGAACTCTTAAGTCCTAAAAGGAAAC
CTCACTCAGATATGCAACATTAAAGATGTCAATCAGCCAGGCACAGTGGCTCATGGCTATAATCCCAACACTTTGGG
AGGCTAGGGAGGGAGGATCATTTGAGCCCAGGAGTTCAAGACCAACCTGGGCAAAATAGGGATACCCTGTGTCTACAA
AAACTACGAAAATTAGCCAGGCATGTTGGCATGCACTTATGCCAGCTACTTGGGAGGCTGAAGTGGGAGGATTGCTTG
AGCCCAGGAGCTTGAGGCTGCAGTGAGCCATGATCACACCACTGCACTTCAGCCTGAGTGACAGAGCAAGAAAAAAAA
AAAAGATGTCTCAAAAAAAAAAAAAAAT CTATGTCAATGATCAGTGCAATCTCCTTCCCTGAATCCAATTTAGAAT
GAGGGGTCTCTGTCTTCTCTCGGTCTTCTGACCAGGTGGTCAGGAGAAAAACTAGTTAGAAACCTCTTTAACTGTTTG
TCTTGCCTTTTCTCCCATTTGCTCATTTATTCATTTGCACATTCATTCAACAAATAAAGTTCCTACCATGTTCCAGAC
ACTGCACTGGATACTGTTCAAAAATAATCCGCCCTGCATGAGGTTCTAAGACAGTTCACTTCTTGTATTTCCATTAT
ACTTTGACTCATGACCGCCTCTCCCTATCACACACACTCCACCTCTAGCCACACTACCTCTCTTGTCCTTTTCCAAAG
CTGCATCTTATTCAGCTATTCTTTCTACTCAGAATGACTTTCTCTATCTGGTATATTCTTGCTTACTCTTCAAGGCCC
AGACAAATGTCGTTTCCTCTATTAAGCTTTCCCTGATCCTCACCCTTGGACAAAATTAATAGCTTCTACCCTTTTTC
ATATGCAGTCATATAAGCACTAAAAGATAATGTATACATTCTATTAAATTAATTGCATATATGTTTAATTTTTTCAC
TTCATTCATAAACTTTGGAAGCAGCAGTTGATTCTTCATATCAGCACTCTTTTCTTTCATAATATCTAATTATTTTAG
GTCATAATAGTCCTCGTTAAATGTTTGGATTAAATCTAATTGAATTGAATTCAAGTGCCAGATCTCTGTAATATGTCT
ACCATGCAACTCTACTACCCTAAGGTTTTGTTTGTCTGTTTGTTTGTTTTATTTTTTTGAGACAGCTTTAACACCTA
GGCTGGAGTGCAGTGGTGCAATCTTGGCTCACTGCAACCTCCACCTCCCAGGCTCAACCATTCCTCCCACCTCCTGAG
TAGCTGGGACTACAGGTGCATACCACCATGCCCGGCTAATTTTTTGTATTGTCTGTAGAGACAGGGTTTCGCCATGT
TGTCCAGGCTGGTGTCTAACTCCTGGGCTCAGGCAATCTGCCCACCTCAGCATCCCAAAGTGCTGGGATTACAGGTGT
GAGCCACTGCTGCCAGTCAACTCTGAGTTATGAGACAGATTTGAGGACTAATTGAAAAGCTAACTTCCCTGGGACATC
CAGGGTTTTTATAATAAAAGGATCACCAAGGCTGAATATTTTATAAGGAACTCAGCCTAAAGGTTTTGGATAGTGCAC
ACCCACTCCTTGCCAGGGCATTAGCTGCTCAAGAAGCAGAGTGTTCTGGACTGGATAGGCAATATCCTTACTTACATA
TACTACAATACAATTCTGATGCTAACCCCCCAAATTAGTGTCAGACCCTACAGGTTAAGAGCATGGTTCCCAACCAGA
TTGCCCTCACTTTAAATGCCAGCTACAAGTTCAGGGTACCCCAGACCACTCACATTTCTGACAAACTGCCTGCAATCT
TAAGGATTCCCATGACCCTCCTCATTGATAATTTGCTAGAATAACTCACAGAATTTAAGAAAGTGCTGTACTTCCTAT
TTCAGTTTTATTAAAAATAAAATAAAATCAGAACCAGCTAAATGAAAAGGGCAAGGTCTAGGAGGGTCCCGAACACA
GAGCCTCCGTGCCCTCTCCCCGTGGAATTAGAACACATCGCCCCCAGCACTCTCCCACACTCTGCCAGCACATTGATG
GGTTCACCAACCAGGAAGCTCCACCAAGTTTTTATTGAGGTATCTTTACATAGGCATGATTGATTGAATCATTGGCCG
CTTGACTGATCTCAATCTCTAGGATCCCTTCCTGGGCTGATACCACTAGTTTCAAAGCTGCAATCCTCTTACCATAT
GGTTGGTCTTGACCAGCACCATCCTGAGTCATTGCCATGCATAAACTCAGGTATGGTCTAAGGATCCACCACAGATAA
CAAAGCCACTCCTGTCACTCATGAAATTCCAACGGTTAGAAACACCCTCCCAGGATACCAGGACAAAGATGAGACAAA
TTGTTTATTATCACCTTGAATTCAATTGAGTGATTTAGTCTACAATCCGGAAAACTAAGTATAGATACTACCATTTTC
ATGGATTTGGATCTTTCTTCATCTTGGCCTCAAATAACCATGGAAATACTTCAGGGCATCTGAACAACTCCATGCCCA
GCTAATACTCTATCTCTCTTCTGTCTTTACAGGTACTTTGGCCCAGTCAATCAAGGTAGGAGAAATGGCTTCTTTCT
ATACTCAGACTCAGAATATTGACGGAAATTTGGCTTCCTACAACAGTAGTCCTACAGGAGCGAACAGTTTAGAATGAA
TGAAATGACGGGGATAGAGAGGTGATGTCTCTATTGTCAACCAAATCAGTGACCTGACATAACCTGTTCCGGGCAGCT
TGCCTGTAGCTAAGCATTTAACTGGTCTCTTACAGGAGAAGCAGGACCCTAGTAGCTAGGGACACATCTCAAACTGTG
ACCCATGAACCAGTAGGTATTGGCGTCACCTGGGATCCTGACGTTAGTCTCTGTCAATCCTTCTCTTTAGTTCATCTA
TTCTACCCAAAGTGATCTCATCATCTGGTATGCTGTTAGCAGTTTCTTACCTGTATAGTATCTTCCAAATAACATGCC
CCAAAATCCCAAGTTTTACCCCTACTAATTACAGCAATGTCTCTTTTATTCTTCACCCCCTGACGCAGATATTGGCG
TCACCCGAGAGCATGTTAGTAATGCAGAATCTCCCCTCCCCAGAACTACTAAATAGCACCTGAAATTTTAACAAGATC
CCCATGTGATTCATGTGCACATCAAAGTTTGAGAAACACTACTCTAATGATCTCCTGGTATGCAGAAGCAGGGAGAAT
TTCAGAGGCAAGATCCTTAATAGAACCACGGCTTTTCTCATTTCAGGAACCACTTGGTTAAGGTGTATGACTATCAA
GAAGATGGTTCGGTACTTCTGACTTGTGATGCAGAAGCCAAAAATATCACATGGTTTAAAGATGGGAAGATGATCGGC
TTCCTAACTGAAGATAAAAAAAAATGGAATCTGGGAAGTAATGCCAAGGACCCTCGAGGGATGTATCAGTGTAAAGGA
TCACAGAACAAGTCAAAACCACTCCAAGTGTATTACAGAAGTATGTAATCCCCTTTGGTCTGTTTGTTGTGAAATTAA
TCAGTATTTGCTGTTCTGGTGAGCTTTTATCTGGGGTGAAAGTGGAAATAGATCCTCAACAGTAATATTATCGCCTG
TTCTCTTAATTTCAGCTTGCCTCTTTTAAAATACTGTAAGATACTTCCCTCACCCTATTGAAAAACTACAGCCAGTCC
```

FIG. 6C

```
TGTAAAATTTTGTTTACCTTTGGGTGGGCTCCATGGATTCAAGCAATTCAGCACTGAGTTGAATGAAGGGGTTGGGGA
GACAGAGGTGATCATAAGGTGAGCAGCAGTGAGAACTGGAGCGCAGTGGAGCATGAAGAGTATCTAGTCTTCCTTCTG
TTCCAGATACTTCCTGGTAGTTAGACTACATGGGCTTCCCCAGGAATCCTGGGGGACTTAAGAGCATCAAGATGCATT
GAGTTTTGGCGCAAGGATCTTCCCTTGCCCTGCCACCCACAGAGGAAAAGCCTGCTGCCCTCCACAGCGGCATTATTG
CAGACAGGCAGGAGAAAACGAACCAGGAAAAACAACTTTCGCAACCTGAAGGTTTGTCTCTCCTTTTCCCTACAGTGT
GTCAGAACTGCATTGAACTAAATGCAGCCACCATATCTGGCTTTCTCTTTGCTGAAATCGTCAGCATTTTCGTCCTTG
CTGTTGGGGTCTACTTCATTGCTGGACAGGATGGAGTTCGCCAGTCGAGAGGTAAAAGAATGCTCTTAGATGAGAGAT
GGGACCACCTGAGACCCTCAGCTTTCCTCCTACCATTATGTACCCAATGGAAGAGACTGAGTTGGTGCTTCTTGCTAG
TGTGCATAGTTGGGTGAGGCTGTATTTCTCTGAGACAGGAGAAAGGATACTTGGTGTTATCACAGCATGTTCACCTGT
CTCAAGATACAGCTCCCTCTGTGAAAAAAAAAAAAAACAAAAACAGGCGCAGTGGCTCACGCCTGTAATCACAACACT
TTGGGAGGCCGAGGCGGGCAGATCACGAGGTCAGGAGATCGAGACCATCCTGGCTAGCACGGTGAAACCCCGTCTTTA
CTAAAAATACAAAAAATTAGCCGGGCGTGGTGGCGGGTGCCTGTAGTCCCAGCTACTCTGGAGGCTGAGGCAGGAGAA
TGGCATGAACCCGGGAGGCGGAGCTTGCGTGAGCCGAGATCGTGCCACTGCACTCCAGCCTGGGCGACAGAGCAAGAC
TCCGTCTCAAAAAAAAAAAAAAAAAAAACTATTTAAGTAAACCCTTACATACAGAAAAGTGAATCACAAGCATACAG
CTCAAAAAAAAAATTCACAGAGCAAATACACCCATGCAGCCAGCACATAATTTAAGAAAGACAATATTACCAATGCCA
TTGAAGCCCTCTTGTGGTCACTTCCAGCCACTACCCATCCTCAAGAGTGAGCATTGTCCTGACTTCTAACAACAAGG
ATTAACTTTGCTTGTTTTTGTCCTTTATGTAAATGGACTCATATACTAAGTATTCTTGTGAGTAGCTTCTTTCACTCA
ACAACATGTTTATGTGCTTTATCCATACTCTTGTGTATATATAAAACTCTTATTGTTATTTAGTATTCCATTTTGTGA
ATATAACCCAATTTATTATGCATTCTACCTTGTGTGGATTCTGTTTCTTTTTTGTGCAGCTTCAGACAAGCAGACTCT
GTTGCCCAATGACCAGCTCTACCAGGTAAGGGGATGAAGAATAAAAGAGACATTGCTGTAATTAGTGGGGTAAATCT
TTGGGATTGAGGGGCATGTTATTTGGAAGATCCTATACAGGTAAGAAACTGCTAACAGCATACCAGATGATGAGATCA
GTTTGGGTAGAATAAATGAACTAAAGAGAAGGATTGACAGAGACTGAGGTCAGGATCTAGTGAGCACAAGTTGAAGAA
CACACTGAGAGGGACACACGAAGAAACTCTCGACAGGCTGGGCACTCACTATAGACAGGCCATGGCTCATGCCTGTAA
TCCCAGCACTTTGGGAAGCCAAAACAGGTGAATCACCTGAGGTCAGGAATTCGAGACAAGCCTGGCCAACATGATGAA
ACTCTGTCTCTACTAAAAATACAAAAAATTAACCAGGCGTGGAGGCGCGCGCCTGTAGTCCCAGCTACTCAGGAGG
CTGAGGCAGGAGGACCACTTGAACCCAGGAGGTCGAGGTTGCAGTGAGCTGCGATTGTGCCACTGCACTCCAGCCTGG
GCAACAGAGAAAGACTCCGTCTCAAAAAAAAAAAAGAGAGAGAGAGAAAAAGAAAAAAGACAGAGCCTCCATCTCCTT
GTCCTCTTTCCATCCTCAGGACCATGAAGTACCCACTCCAAATTCTCACATATAAAAAACATTCAATAAACATGCATC
AAATTAATTAATAGAGGATGGAAAAAATGACTTATGACTGTGCTGTCCTTTCCAGCCCCTCAAGGATCGAGAAGATGA
CCAGTACAGCCACCTTCAAGGAAACCAGTTGAGGAGGAATTGAACTCAGGACTCAGAGTAGGTGGGTTCTTCAATGCC
AATTCTAATAAAGGACCCTTGCATCAACTGCCCTCGCAATTGCTTCTAAGTCTAGCTCCCTTCCCTAAGCGGCTATAA
GCATCAGACTCTGGGGATCAGGGATTGGGACGTGGTTTGGGGTACTCTTTTCTAAAAATTCTGGGGCCATACTGATTG
TCTTGGCCTAGGTAAATATGAATTTTATGTATCTGTAAATCCTGTCAGAGCAGGGCCTCAAGCCATAGAGATGCTGAA
TATTAATCTTAACCTACATTTGAATTTCTCATTATCTACACTATTAACATTTTGGGCTAATTAATTATTTGTGATGAG
GGGCTAGCCTGTGCATTGTAGGAGTTATGGAAGCATCCCTGGCCTCTCTCCACCAGATGCTGGTAGATTGTCCAGTGT
GACAATCAAAATGTGTCCAGACATTACCAAATGTGTCCAAACATCACCTCCAGGGCAAAATCACCCTTAGTTAAGAA
CCACTAACCCATATTAACCTTCCAATCAATAAATCAATCAGTCAGAAGTTATGATTTAATTAATCTATCTGAAGTTTC
TATCAGGAAGACAGGGTTGAAAGCATTATTTGTTTTTTTTGAACAAATTGCAATTTTCTTTTTTCAGTCCAGGTGTT
CTCCTCCTATTCAGTTCCCAGAATCAAAGCAATGCATTTTGGAAAGCTCCTAGCAGAGAGACTTTCAGCCCTAAATCT
AGACTCAAGGTTCCCAGAGATGACAAATGGAGAAGAAAGGCCATCAGAGCAAATTTGGGGGTTTCTCAAATAAAATAA
AAATAAAAACAAATACTGTGTTTCAGAAGCGCCACCTATTGGGGAAAATTGTAAAAGAAAAATGAAAAGATCAAATAA
CCCCCTGGATTTGAATATAATTTTTTGTGTTGTAATTTTTATTTCGTTTTTGTATAGGTTATAATTCACATGGCTCAA
ATATTCAGTGAAAGCTCTCCCTCCACCGCCATCCCTGCTACCCAGTGACCCTGTTGCCCTCTTCAGAGACAAATTAG
TTTCTCTTTTTTTTTTTTTTTTTTTTTTGAGACAGTCTGGCTCTGTCACCCAGGCTGAAATGCAGTGGCACCAT
CTCGGCTCACTGCAACCTCTGCCTCCTGGGTTCAAGCGATTCTCCTGCCTCAGCCTCCCGGGCAGCTGGGATTACAGG
CACACACTACCACACCTGGCTAATTTTTGTATTTTTAGTAGAGACAGGGTTTTGCTCTGTTGGCCAAGCTGGTCTCGA
ACTCCTGACCTCAAGTGATCCGCCCGCCTCAGCCTCCCAAAGTGCTGGGATTACAGGTGTGAGCCACCATGCCTGGTC
TTAAAACCAGTTTCTTATATATCTCTCTGGAGGTATTCTAGGCATATATGAGCACATTCTCAAGTACATATTATCCTC
CCTTCCCCTATCTTTTAGACAAATGATATCAAACTATACATCTTGTGAGATTATTGCATACCATTATATGAAGATACC
ATTATATCCTTTTTAATGCAACCATATTGTACAAATAGACTATGATTTATTTAACCTGTTATCTATCAGTGGATATTT
```

FIG. 6D

AAGTTGGTAGTTGGTTCCAATCTTTTGCTCTTACAACAATTCTGCAATGACTAACATTGTATAAATATCATTTTTAAA
AATAATTGCATTGAAGCATAATGTACATGCCATAAAATCCACCCATCTTAAGTGATTTCACCTGTTCTCAGAAATTTT
TAGTAAATTTAACTAATTGTACAGCCATTACCATAATCCAGCTTTAGGACATTTTCTTTTTTTTCTTTTCTTTTCTTT
TTTTTCTTTTTTTTTTTTTTTGAAGTGGAATCTTGCTCTGTGGCCCAGGCTGGAGTGCAGTGGCGCGATCTCAGCTC
ACTGCAACCTCCACCTCCTGGGTTCAAGCGATTCTCTTGCCTTGGCCTCCCGAGTAGCTGAGACTACAGGCACATGCC
ACCACGCCCAGCTCATTTTTTGTGTATTTAGTATTTGTGTATCTAGTATTTGTGTACTTAGTAGAGACAGGGTTTCAC
CATGTTGGCCAGGCTGGTCTCCAATTCCTGACCTCAGGCGATC

FIG.6E (SEQ ID NO: 74)

CAAATAAACCTCACTCCCATCAATAATATCCCTCTCAAATCCCTTCCCCCACCCACCTAAAATAACCTTACCTT
ACAAAAAAAAATAACCAATACCAAACCAAAAAAAAACATACTATATTCCATCTCCCAACAAAACTCATCCAAT
AAATAAAACCAAATCACCAAAC

TATCAACCTAAATAAAAACTACCCTCCCCTAACTAACTCACAAATACCAAAAAAAAAAAAAATAAAAAAAAACT
AAAAAATATCTACTTCTCTACTTTCTACCATTAATAATAAAAAATTTTCAAAATAAAAATAAACTAAAAATAAA
ATAAAAAAAAAACAATATAAATTAC

TCTATCTCTAAACAAAAAACTAACAAAAAATATAAAAAAAATAACCTAAACTTTAACATCCCTATTAACAATAC
AACCACATTTACACACAACCTAAACACTACCACATCTCAAAACCCCTTAAAAAAAACCATCAACCCCATAACAC
AAACCATAACAACTAAATTTCTCATA

AAAACTAATCTTTCTCAAAACCCTTCACTAAACAACCAAAAACACCAAATCTAACAACTTCTTATCAATAAAAA
ATTAAACTTTAAAAACCCCAACCAAAAATTTAAATCCTAAATCCAATACTACCTACCTATAAAACCTAAACCAA
CCATAAAATTTTTCAAAATCTTATTCCAT

TAATACCATTATTAAAATTCAAACAAAATATTTACATAATACCTCACACATCATATATACTCATTAAAAAATAA
TTATTAATAATAATATAATTAACTAACAAACAATATTAAACCTCCCAATAAAACAAATAAACCTTTTTCCCCTA
TAACCTACAAAAATCTAAAACTCTTCACACTA

CTACAATTAAACTATCACTTACCTAAAAACAAAATCATACCTATCTTACTCACTACTATATCTTATACCTAACA
CATAACAAAACTCTACACATTTTTATTAACTCACTAACTAACTAACTAAAAAAAATAAAAACCTAAAATCCTA
AACATTCAATCCAAACTCTAACCCCTAAAAA

TATACTAACCTATCCTCAAAATTATTCCACCTATTACCTTCCAAACACCTCTTTCATAATCTCAAAAAAATAAT
AAAACCAAATACCATATCTCACACCTATAATCCCAACACTTTAAAAAACTAAAACAAATAAATCACAAAATCAA
AAATTCAAAACCAACCTAACCAACAAAATAAAA

CCCCATCTCTACTAAAAATACAAAAATTAACCAAACTTACTAACACACACCTATAATCTCAACTACTCAAAAAA
CTAAAACAAAAAATCACTTAAACCCCAAAAATAAAAATTACAATAAACTAAAATAACACCACTACACTCCAAC
CTAAACAACAAAATAAAACTCTATCTCAAAAA

AAAAAAAAAAAAAAAI TAAAAAAAATTCCTAAATAAAAACCTAAACTAAAATAACTTTCCATTTAAAAATCC
AACCCCAAACATCTAAAAATCCCTCCTAAATTCATTACCTACAACAACAACAACTAACAACAAATAACAACTAA
CTACAATCCTAACAACTAATAACAAAAACATTTAT

CTCCCTCATAAAAAAACAATCCCAAAACCATCTCCCACCCAACATCCATTACAATTCCCTATACAAAATAAATC
TCTAAATAAAAATCCAACACTCTCTCCCTCTTCTTCCCCACCACCTTCACCCTCCTTAACAAAAAAACAAAAAA
CATCTACACCTACAACCCTACTAAAACCCCTACTAC

TCACACTTACAACAAAAATAAAAACTCTAAATTCTTACCTTCTCTCAAAAACCCCAACCCCAACAATAATAAA
TAAAACCAATCTAACTACTACACAAACTAACTAACTAACTAACTACTAAAAACTACTCCACACTTTTACCAAAA
AACAAAAACTAACATAAAACAAAAAAAAAACCTAA

CTATCCTCATCCTA

FIG. 7

(SEQ ID NO: 75)

CAAATAAACCTCACTCCCATCAATAATATCCCTCTCAAATCCCTTCCCCCACCCACCTAAAATAACCTTACCTT
ACGAAAAAAAAATAACCAATACCAAACCAAAAAAAAACGTACTATATTCCATCTCCCAACGAAACTCATCCAAT
AAATAAAACCAAATCACCGAACTATCAACCTAAATAAAAA

CTACCCTCCCCTAACTAACTCACAAATACCGAAAAAAAAAAAATAAAAAAAAAACTAAAAAATATCTACTTCTC
TACTTTCTACCGTTAATAATAAAAAATTTTCAAAATAAAAATAAACTAAAAATAAAATAAAAAAAAACGATAT
AAATTACTCTATCTCTAAACAAAAACTAACAAAAAATATAA

AAAAAATAACCTAAACTTTAACGTCCCTATTAACAATACAACCACATTTACACACAAC<u>CTAAACACTACCACAT
CTCGAAACCCCTTAAAAAAAACCGTCGACCCCATAACGCAAACCGTAACAACTAAATTTCTCATAAAAACTAAT</u>
CTTTCTCAAAACCCTTCACTAAACAACCAAAAACACCAAATCT

AACAACTTCTTATCAATAAAAAATTAAACTTTAAAAACCCCAACCAAAAATTTAAATCCTAAATCCAATACTAC
CTACCTATAAAACCTAAACCAACCATAAAATTTTTCAAAATCTTATTCCATTAATACCATTATTAAAATTCAAA
CAAAATATTTACATAATACCTCACGCATCATATATACTCATTAA

AAAATAATTATTAATAATAATATAATTAACTAACAAACAATATTAAACCTCCCGATAAAACAAATAAACCTTTT
TCCCCTATAACCTACGAAATCTAAAACTCTTCACGCTACTACAATTAAACTATCACTTACCTAAAAACAAAAT
CATACCTATCTTACTCACTACTATATCTTATACCTAACACATAACGA

AAACTCTACACATTTTTATTAACTCACTAACTAACTAACTAAAAAAAATAAAAACCTAAAATCCTAAACATTCA
ATCCGAACTCTAACCCCTAAAAATATACTAACCTATCCTCGAAATTATTCCACCTATTACCTTCCAAACGCCTC
TTTCATAATCTCAAAAAAATAATAAAACCAAATACCGTATCTCACGCCT

ATAATCCCAACACTTTAAAAAACTAAAACAAATAAATCACAAAATCAAAATTCGAAACCAACCTAACCAACAA
AATAAAACCCCGTCTCTACTAAAAATACAAAAATTAACCGAACTTACTAACACGCACCTATAATCTCAACTACT
CAAAAAACTAAAACAAAAAAATCGCTTAAACCCCGAAAATAAAAATTACA

ATAAACTAAAATAACGCCACTACACTCCAACCTAAACAACAAAATAAAACTCTATCTCAAAAAAAAAAAAAAAA
AAAAAATAAAAAAAATTCCTAAATAAAAACCTAAACTAAAATAACTTTCCATTTAAAAATCCAACCCCAAACA
TCTAAAAATCCCTCCTAAATTCATTACCTACAACAACAACAACTAACA

ACAAATAACAACTAACTACGATCCTAACAACTAATAACAAAAACATTTATCTCCCTCATAAAAAAACGATCCCA
AAACCATCTCCCACCCAACATCCATTACGATTCCCTATACAAAATAAATCTCTAAATAAAAATCCAACACTCTC
TCCCTCTTCTTCCCCACCACCTTCACCCTCCTTAACGAAAAAACAAAAAAC

ATCTACACCTACAACCCTACTAAAACCCCTACTACTCACACTTACAACAAAAAATAAAAACTCTAAATTCTTAC
CTTCTCTCAAAAACCCCAACCCCAACAATAATAAATAAAACCAATCTAACTACTACACAAACTAACTAACTAAC
TAACTACTAAAAACTACTCCACGCTTTTACCGAAAAACAAAAACTAACATAA

AACAAAAAAAAAACCTAACTATCCTCATCCTA

FIG. 8

SEQUENCE LISTING

<160> NUMBER OF SEQ ID NOS: 82

<210> SEQ ID NO 1
<211> LENGTH: 16501
<212> TYPE: DNA
<213> ORGANISM: Homo sapiens

<400> SEQUENCE: 1

| | | | | | |
|---|---|---|---|---|---|
| agatgacatc | tattgaaaat | atccctgtct | cagccaggtg | cagtggctca | tgcctctaat | 60 |
| cccagcactt | ttggaggctg | agtgagtgga | tcatttgagg | tcaagagttc | gagaccagcc | 120 |
| tggccaacat | gatgaaaccc | tgtctctact | aaaaatacaa | aaattagctg | aacttggtga | 180 |
| cacatgcttg | caatcccagc | tactcaggag | gctgaggcag | gagaatcact | tgactccagg | 240 |
| agacagaggt | tgcagtaagc | caagatcatg | ccacagcact | ccagcctgag | caacagagca | 300 |
| agactccatc | tcaaaaaaaa | aaaaaatccc | tgtctcaaac | tcctgctttc | caggtagatg | 360 |
| gagcgggata | atgtgcttta | attggtgaag | ggtttctgat | ccccatttat | catgcagaag | 420 |
| gcaggagcaa | gccagagaca | ggtcctggcg | aaaggaagct | aaaatggtgc | ctttgataca | 480 |
| ggggaaaggg | atacgaaagg | ggcttaggtg | agacctcctt | acagctagtg | gcacctggtc | 540 |
| agcagggccg | tagagttgag | gccatcccct | tagcagcagt | gggactttgt | tacacacacc | 600 |
| ctctgagtct | tggtgagaaa | ctagtcccag | ggcccttgt | tgtctctgcc | actcccattc | 660 |
| atgacatcat | ggaaacttct | gtgcggctgg | gctcctgaac | acagcagcct | gccctcggct | 720 |
| ggatgaggca | gccaaaaccc | taaagggtt | gtgatagga | ctggagtcaa | caagtagctg | 780 |
| tgggaacgtg | gtggcgcaga | cccttcaccc | agggagccct | gtgggctaga | aacaccagac | 840 |
| agccaggatg | tggcgagaga | ctgcccaaca | cactgtctgt | gtgaggcaga | ggaaggaagg | 900 |
| agatgaagga | agaaacaggt | aggtaggagg | gcgagatccc | aagcaagtca | ggacaactcc | 960 |
| cacgccttgc | ccaggagcct | taagaagccc | aggcacctgc | tgagtgaaag | aggatatatt | 1020 |
| tattggctga | gcaagaaggg | aaggtacagt | tggtaatggc | tgcttctaga | agccaccagt | 1080 |
| ctcaggttca | cttgttccga | gcccagtttc | ctccaaggtg | gctgtactga | gcatcatctc | 1140 |
| gatctcggag | gggctaagag | aggagaagag | aaaacggtca | ggaggcaggg | ttagaactct | 1200 |
| tcaaggaagg | gccccagcag | gccctgacga | tgagagctcc | tgcctgacct | ctccagtcac | 1260 |
| acccagcaat | gaactcccca | gtaggaccct | tcccacgtgc | aaacagcatt | cagtgtgagc | 1320 |
| ctctctatcc | ccacttaccc | tcccttcatt | cctgcctcct | tccctcaac | gctcacctga | 1380 |
| tagacctggt | cattcctcaa | cagagcttgt | gtgtcggcag | ctagaagaac | cagagagaga | 1440 |
| catcaatggc | ctagcagatg | ggactgtgag | atccaccctc | ccacaccctc | agaagtctgc | 1500 |
| atgagtgata | tgaacacaca | agttctttca | acagtcaaag | ttctaggagt | ctttaggaga | 1560 |
| ttgcaagagt | aactcccagc | tgagactaaa | cctaccacca | gcccattcc | ttagctggtg | 1620 |
| cataagctca | ctggtacaca | cacacacaca | cacacacaca | cacacacaaa | cacactctca | 1680 |
| tgctctgctc | ttccactaac | ccccagacag | ccttccagtc | tcatgtccag | caaagcagaa | 1740 |
| gactcccaaa | gcaaggagca | gagtggcaat | gacatcagta | caatgatgc | cagccacggt | 1800 |
| ggctggatcc | agctccacac | agctctggca | cactgtgggg | gaaggagga | gagaggagag | 1860 |
| gttgagagcc | tttaagatca | gggaaccatc | ctctgcctcc | tagggcaacc | cttagatctc | 1920 |
| ttatgccaaa | acccaaactt | caataagacc | ctgggagaaa | ggcctggtga | tgggcttgcc | 1980 |
| acaccttcct | ccaccctgca | tcctaaggaa | tccctgggaa | gagccaagaa | gtaatctcag | 2040 |
| cttttgggac | cttgaacaag | gtggtgggcc | aaacctctca | cccaaccaag | gctgcagtaa | 2100 |

```
catgacccct actgctctgt cttgctgagt taagctctct cttccacttt gaaggtcccc    2160
aaatctggct tgtaccatta caatagtgac ctcactttgt ttagagaaca gatgggttca    2220
ccatatccct ctctagccag aaagttctca catccagaag ccctatccat tccaacccaa    2280
agggttcagg aagcacgtac ttcgataatg aacttgcacg gtagattctt tgtccttgta    2340
tatatctgtc ccattacacc tatatattcc tcgtgggtcc aggatgcgtt ttcccaggtc    2400
cagtcttgta atgtctgaga gcagtgttcc caccgttccc tctacccatg tgatgctggt    2460
attgcaattc acaaacactc tgtcctcaag ttcctctata ggtatcttga aggggctcac    2520
taaaggggaa aaaatatcac agttggagac agctctttga tctgcaccaa gccctttgtt    2580
ctgcggaagc tcatacttaa cagagaccat tttcctggtc caggacagtt tatggcttcc    2640
atcaagagag acagaagtca caagaaaaag ccttcagaaa gttccccacc aactgcaggg    2700
gtcaaggggg acatgaggat gccattcaag cagaggacag gtcttggggc cttggtgcaa    2760
aagaggaccc ctcagagcag gattgaccca agcaccttcc tggaaatgaa tccagaccac    2820
tgatgaggag tagggggagc acggaccact gaagcacctg gaagatgtgg aaagacagaa    2880
gaacattcct cgattggaaa tgtctgcatt ttttcttcaa ggaaacatct aattccactt    2940
cccagccatc tacaacactc ccacttcagc ttcttatcct catccttcct cattgcccct    3000
gctccattga caaccaagaa agcggggctc tcaacactga agcctttccc agggccaggg    3060
atggctgtgg gtggagacca gctggtttac cagcccctga attatcagcc aagtggtcca    3120
gaacgggacc agggcaaatc ccatgtacag ttttccaccc ttggttagaa ggaggagaac    3180
aggaaaaaaa ttttattgaa tccatcccta gagctcctca caagtcaagt cttgtgggag    3240
acttttaggg ctggaggtga gtgcagcaac attccagatg cagtgagttc ctctgacagc    3300
ctgagcacat ctccacaggc cacagaggca ctacagtcta tgcctccaaa cacagggaaa    3360
agtggaggct acattcattc atcctgggct tcacactaag tcccaaattt ggatacaaga    3420
gcatcttcta gaaaaccctg aaacagctgt tgctcacact tctgaagcag gttggaagta    3480
tatgcatgta tcctcaggga gacacatgca catcaaatgc ttcacgtcct acagtcgcgt    3540
cctcttcagg gatctgtctc cagtggaaat cctgagtgcc ctagtgcagc caactattag    3600
gtgaccattg gacccagttt gcttagtgtt gaaggggttc ctcggacatg gactttcca    3660 ttttaaaact gaaattggca aactgagatg agttaaaatc ctaccatgta acaacccctc    3720
aaatcttccc tccgtcctgc tcaacctaaa gttaacttct cttaaagcat tcacataagt    3780
gctaggacat gcctccaggg atgacataat catggccaaa caaacaagag tcctgattcc    3840
agaggccatc aggcctaaaa ggagtagtgc aggaagctgt gctcccatgg ccagtcccag    3900
attcaggtac atacgtactg agctattttc tgcagatctc tggcctaagg ccttctgaga    3960
gacattctag gcccacatgc acccatggct ggagtcagtc aaagccaaga gcctgttttcc    4020 cagactctat gctacatcct gcccctgccc tcctgacacc cctggggtgc ctggtgaact    4080
gaagctagca ccgagaagca cttttttttt tttttgagat aaggtctcac aggttgccta    4140
ggttggaggg cagtggcatg atcacagctc actgaagcct tgaaatcccg ggctcaagtg    4200
accctcctgc ctcagcctct caaatagctg gactacagt tgtgcaccac catgcctggc    4260
taattctttt gttttttgta agatagagt ctcatcatgt tgctcagact ggtctcaaac    4320
tcctggcctc aaaggatcct cccacttcgg cctcccaaag ctctgggatt actggtgtga    4380
gccaccgtgc ctggcaagaa acactttcaa gtgggcctca ctcccatcag taatgtccct    4440
```

```
ctcaggtccc ttcccccacc cacctggagt agccttacct tgcgagagaa gggtagccag    4500
taccaggcca gagagaaacg tgctatgttc catctcccag cggaactcat ccagtagata    4560
aagccaggtc accgaactat cagcctgggt gagagctgcc ctcccctagc tgactcacag    4620
gtaccggaaa gaggagagtg ggggaggaac tagaagatgt ctgcttctct gctttctgcc    4680
gttgatggtg ggaattttc agagtggggg tgggctaggg gtagggtagg aaggaagcgg     4740
tgtaaattgc tctatctctg agcagggagc tggcagagaa tatggaaaag gtggcctgaa    4800
ctttagcgtc cctattgaca atgcaaccac atttacacac aacctaaaca ctgccacatc    4860
tcgaagcccc ttgagagaag ccgtcggccc catagcgcaa gccgtagcag ctagatttct    4920
catggaggct gatcttctc aggacccttc actaggcagc cagggacacc agatctagca    4980
gcttcttgtc agtgggaggt tgggctttag agacccagc cagagatttg aatcctgggt     5040
ccaatactgc ctacctgtgg ggcctgggcc agccataaaa ttttcagag tcttattcca     5100 ttagtaccat tattaggatt caaacaagat atttgcatgg tgcctcacgc atcatatgtg    5160
ctcattaagg ggtagttatt aataataata taattgactg acaggcaata ttgagcctcc    5220
cggtgagaca aatggacctt ttccctgt ggcctacgag gatctgaaac tcttcacgct      5280
gctgcagtta gactgtcact tacctgggga cagagtcatg cctgtcttgc tcactgctgt    5340
atcttgtgcc tggcacataa cgggagctct gcacattttt gttggctcac tgactgactg    5400
gctgagggag atagggcct gagatcctgg acattcagtc cgggctctgg cccctgaaaa     5460
tgtgctggcc tgtcctcgga attgttccac ctattgcctt ccaggcgcct ctttcatgat    5520
ctcaaaagaa tagtgaaacc aggtgccgtg tctcacgcct gtaatcccaa cactttggga    5580
ggctgaggca ggtggatcac aaggtcagga gttcgagacc agcctgacca acaaggtgaa    5640
accccgtctc tactaaaaat acaaaaatta gccgggcttg ctggcacgca cctgtaatct    5700
cagctactca ggaggctgag gcaggagaat cgcttgaacc ccggaggtgg aggttgcagt    5760
gagctgagat agcgccactg cactccagcc tgggcaacaa agtgagactc tgtctcaaaa    5820
aagaaaaaga aaaaaaagt gaaaaaaatt cctgaatgaa ggcctggact gaggtggctt     5880
tccatttgga ggtccagccc caagcatctg agagtccctc ctaaattcat tacctacagc    5940
aacaacaact agcaacaagt aacaactggc tacgatccta acaactaatg acagggacat    6000 ttatctcct catgaagaaa cggtcccagg accatctccc acccagcatc cattgcggtt     6060
ccctgtgcaa gatgagtctc tgagtgggaa tccagcactc tctccctctt cttccccacc    6120
accttcaccc tccttaacgg aaaaacaaaa ggcatctgca cctgcagccc tgctgaggcc    6180
cctgctgctc acacttgcag cagagggtgg aggctctggg ttcttgcctt ctctcaaagg    6240
ccccagcccc aacagtgatg ggtggagcca gtctagctgc tgcacaggct ggctggctgg    6300
ctggctgcta agggctgctc cacgcttttg ccggaggaca gagactgaca tggaacaggg    6360
gaagggcctg gctgtcctca tcctggctat cattcttctt caaggtaagg gcctactagg    6420
ggtctggaag cctggggaag ggctcaaggg aagagcccat cactagtgag acaggaatat    6480
tggtatccct aaccttcagc ctacctctgc tgtcaccta gagttcaaag aagggcaaaa     6540
tggaggctct taactgttct ctgctagaga gaaacagtgt cccatggagg agaaggaatc    6600
cttgtctctg aaaaatgcaa acagagtact taaatggctg aagagaggac cctgttaccg    6660
ccatcttaga tttgaatgca gcccaaaagg gcataggcca agaaactaaa aggaaaaagt    6720
atatgttccc tacttcagag ctgggggcta gcagtcgacc taggaaatgt ccattcactc    6780
agttgggcag ttggccaatt ggtcaacaaa gatgggtgag accctaatat gtgatatgcc    6840
```

```
atgaggaaat aaaaatgaat aaaacactta tgctctacag aactcatagt ctcattggag    6900
agattagttt tcatggtgcc agactgagtg tacagtatag tatgggtgcc tgcatgaata    6960
ctccattgga ctatccaata ggaagtggat gaactgggtt gatgcctgga gtctggacat    7020
cctgggaaag ttaaaccat ggaatttgct gaagtcacac aagtactatg tgaggaagag     7080
ggagctgaag atggaacagt gagggcacca attttaaggg gcagttagag aaaaaaaaac    7140
attccaggaa agagataaaa ggagaatcaa agagctgaaa taatcaaatg tatgcactac    7200
cttggaaacc aagagagtag agagcttcta gaagaagaga attaccaaga gtataaaatg    7260
ttaaagagag cccactaata taagaatata tttaaaagtt taagtctgcg ggatgtggca    7320
gaatatgcat catgggtgat ttagcacagt ttcagcaggg tattgtgagt ggaagccaag    7380
tgaaaattgg tagaaggtga aggtcaggtg atgaggtcag caagtgtaga ctattctta    7440 aagacatttg gatgaggagg gagaaaagac tgggtggtag gtagaggagg aagtagagtc    7500
taagaataaa tgttttgag ggtgagagaa acttgagcac atttctaggc taaggagaa     7560 gatgatgagt agagcaaggt cctggagttg atggtggaag gacagagtca agagtggggt    7620
caagagcaca gagaggaagg caacgttacc ctctaagacc aggagaaagg aagtgcaaac    7680
ggcactggcc acaaataggt ttataaaggg aaaggaagct aaaggagaaa ggacaataac    7740
aacttccgtg ttctaaaaaa tccaggtggg aggcaatgcc acctgctgaa actgagctgg    7800
gtgatgaccg gttgggagac ttgaagagga cagtgagagt ttagaataga attatttctg    7860
agagaaatgc aaggaaaagt caggtaaaga caacacaggt tgaggagcaa ctctcaagcc    7920
tgggtgaggt ggctgcatat catggaaaga gcatttgagt tcagcagtag aaaacctgag    7980
ctctggatcc agcttggaca ccaatgagct atgtgtactt gaacaactcc tccactgtct    8040
gggagttctc atgccagcca atccagaaat gtggcaggga cgggcatggt ggctcatgcc    8100
tgtaatccca gcactttggg aggtcgaggc aggtggatca cctgaggtca ggagttcgag    8160
accatcctgg tcaacatggt gaaactctat ctctactaaa aatatttaa aaattagtgg     8220 ggtgtggtgg tgggtgcctg taatcccagc tactcaggag gctgaggcag gagaattgct    8280
tgaacccagg agatggaggt tgcagtgagc caacacggtg ccactgcact ccagcctggg    8340
cgacagagtg agactccgtc tcaaaaaaca aacaaaaaa aaagaaatg tggctatatg      8400 aactcttaag tcctaaaagg aaacctcact cagatatgca acattaaaag atgtcaatca    8460
gccaggcaca gtggctcatg ctataatccc aacactttg ggaggctagg gagggaggat     8520
catttgagcc aggagttca agaccaacct gggcaaaata gggatacct gtgtctacaa      8580 aaactacgaa aattagccag gcatgttggc atgcacttat gccagctact gggaggctg     8640 aagtgggagg attgcttgag cccaggagct tgaggctgca gtgagccatg atcacaccac    8700
tgcacttcag cctgagtgac agagcaagaa aaaaaaaaa agatgtctca aaaaaaaaaa     8760 aaaaactat gtcaatgatc agtgcaatct ccttccctga atccaattta gaatgagggg     8820
tctctgtctt ctctcggtct tctgaccagg tggtcaggag aaaaactagt tagaaacctc    8880
tttaactgtt tgtcttgcct tttctcccat ttgctcattt attcatttgc acattcattc    8940
aacaaataaa gttcctacca tgttccagac actgcactgg atactgttca aaaataatcc    9000
cgccctgcat gaggttctaa gacagttcac ttcttgtatt tccattatac tttgactcat    9060
gaccgcctct ccctatcaca cacactccac ctctagccac actacctctc ttgtcctttt    9120
ccaaagctgc atcttattca gctattcttt ctactcagaa tgactttctc tatctggtat    9180
```

```
attcttgctt actcttcaag gcccagacaa atgtcgtttc ctctattaag ctttccctga    9240
tcctcaccct tggacaaaat taatagcttc tacccttttt tcatatgcag tcatataagc    9300
actaaaagat aatgtataca ttctattaaa ttaattgcat atatgtttta attttttcac    9360
ttcattcata aactttggaa gcagcagttg attcttcata tcagcactct tttctttcat    9420
aatatctaat tattttaggt cataatagtc ctcgttaaat gtttggatta aatctaattg    9480
aattgaattc aagtgccaga tctctgtaat atgtctacca tgcaactcta ctaccctaag    9540
gttttgtttg tctgtttgtt tgttttattt ttttgagac agctttaaca cctaggctgg    9600
agtgcagtgg tgcaatcttg gctcactgca acctccacct cccaggctca accattcctc    9660
ccacctcctg agtagctggg actacaggtg cataccacca tgcccggcta atttttttgt    9720
attgtctgta gagacagggt ttcgccatgt tgtccaggct ggtgtctaac tcctgggctc    9780
aggcaatctg cccacctcag catcccaaag tgctgggatt acaggtgtga gccactgctg    9840
ccagtcaact ctgagttatg agacagattt gaggactaat tgaaaagcta acttccctgg    9900
gacatccagg gttttttataa taaaaggatc accaaggctg aatattttat aaggaactca    9960
gcctaaaggt tttggatagt gcacaccac tccttgccag ggcattagct gctcaagaag    10020
cagagtgttc tggactggat aggcaatatc cttacttaca tatactacaa tacaattctg    10080
atgctaaccc cccaaattag tgtcagaccc tacaggttaa gagcatggtt cccaaccaga    10140
ttgccctcac tttaaatgcc agctacaagt tcagggtacc ccagaccact cacatttctg    10200
acaaactgcc tgcaatctta aggattccca tgaccctcct cattgataat ttgctagaat    10260
aactcacaga atttaagaaa gtgctgtact tcctatttca gttttattaa aaaataaaat    10320
aaaatcagaa ccagctaaat gaaaagggca aggtctagga gggtcccgaa cacagagcct    10380
ccgtgccctc tccccgtgga attagaacac atcgccccca gcactctccc acactctgcc    10440
agcacattga tgggttcacc aaccaggaag ctccaccaag ttttattga ggtatcttta    10500 cataggcatg attgattgaa tcattggccg cttgactgat ctcaatctct aggatccctt    10560
cctggggctg ataccactag tttcaaagct gcaatcctct taccatatgg ttggtcttga    10620
ccagcaccat cctgagtcat tgccatgcat aaactcaggt atggtctaag gatccaccac    10680
agataacaaa gccactcctg tcactcatga aattccaacg gttagaaaca ccctcccagg    10740
ataccaggac aaagatgaga caaattgttt attatcacct tgaattcaat tgagtgattt    10800
agtctacaat ccggaaaact aagtatagat actaccattt tcatggattt ggatctttct    10860
tcatcttggc ctcaaataac catggaaata cttcagggca tctgaacaac tccatgccca    10920
gctaatactc tatctctctt ctgtctttac aggtactttg gcccagtcaa tcaaaggtag    10980
gagaaatggc ttcttctat actcagactc agaatattga cggaaatttg gcttcctaca    11040
acagtagtcc tacaggagcg aacagtttag aatgaatgaa atgacgggga tagagaggtg    11100
atgtctctat tgtcaaccaa atcagtgacc tgacataacc tgttccgggc agcttgcctg    11160
tagctaagca tttaactggt ctcttacagg agaagcagga ccctagtagc tagggacaca    11220
tctcaaactg tgacccatga accagtaggt attggcgtca cctgggatcc tgacgttagt    11280
ctctgtcaat ccttctcttt agttcatcta ttctacccaa agtgatctca tcatctggta    11340
tgctgttagc agtttcttac ctgtatagta tcttccaaat aacatgcccc aaaatcccaa    11400
agttttaccc ctactaatta cagcaatgtc tcttttattc ttcaccccct gacgcagata    11460
ttggcgtcac ccgagagcat gttagtaatg cagaatctcc cctccccaga actactaaat    11520
agcacctgaa attttaacaa gatccccatg tgattcatgt gcacatcaaa gtttgagaaa    11580
```

```
cactactcta atgatctcct ggtatgcaga agcagggaga atttcagagg caagatcctt    11640
aatagaacca cggcttttct catttcagga aaccacttgg ttaaggtgta tgactatcaa    11700
gaagatggtt cggtacttct gacttgtgat gcagaagcca aaatatcac atggtttaaa     11760 gatgggaaga tgatcggctt cctaactgaa gataaaaaaa aatggaatct gggaagtaat    11820
gccaaggacc ctcgagggat gtatcagtgt aaaggatcac agaacaagtc aaaaccactc    11880
caagtgtatt acagaagtat gtaatcccct ttggtctgtt tgttgtgaaa ttaatcagta    11940
tttgctgttc tggtgagctt tttatctggg gtgaaagtgg aaatagatcc tcaacagtaa    12000
tattatcgcc tgttctctta atttcagctt gcctctttta aaatactgta agatacttcc    12060
ctcaccctat tgaaaaacta cagccagtcc tgtaaaattt tgtttacctt tgggtgggct    12120
ccatggattc aagcaattca gcactgagtt gaatgaaggg gttggggaga cagaggtgat    12180
cataaggtga gcagcagtga aactggagc gcagtggagc atgaagagta tctagtcttc      12240
cttctgttcc agatacttcc tggtagttag actacatggg cttccccagg aatcctgggg    12300
gacttaagag catcaagatg cattgagttt tggcgcaagg atcttccctt gccctgccac    12360
ccacagagga aaagcctgct gccctccaca gcggcattat tgcagacagg caggagaaaa    12420
cgaaccagga aaaacaactt tcgcaacctg aaggtttgtc tctccttttc cctacagtgt    12480
gtcagaactg cattgaacta aatgcagcca ccatatctgg ctttctcttt gctgaaatcg    12540
tcagcatttt cgtccttgct gttggggtct acttcattgc tggacaggat ggagttcgcc    12600
agtcgagagg taaagaatg ctcttagatg agagatggga ccacctgaga ccctcagctt      12660
tcctcctacc attatgtacc caatggaaga gactgagttg gtgcttcttg ctagtgtgca    12720
tagttgggtg aggctgtatt tctctgagac aggagaaagg atacttggtg ttatcacagc    12780
atgttcacct gtctcaagat acagctccct ctgtgaaaaa aaaaaaaaac aaaaacaggc    12840
gcagtggctc acgcctgtaa tcacaacact ttgggaggcc gaggcgggca gatcacgagg    12900
tcaggagatc gagaccatcc tggctagcac ggtgaaaccc cgtctttact aaaaatacaa    12960
aaaattagcc gggcgtggtg gcgggtgcct gtagtcccag ctactctgga ggctgaggca    13020
ggagaatggc atgaacccgg gaggcggagc ttgcgtgagc cgagatcgtg ccactgcact    13080
ccagcctggg cgacagagca agactccgtc tcaaaaaaaa aaaaaaaaaa aactatttta    13140
agtaaaccct tacatacaga aaagtgaatc acaagcatac agctcaaaaa aaaaattcac    13200
agagcaaata cacccatgca gccagcacat aatttaagaa agacaatatt accaatgcca    13260
ttgaagcccc tcttgtggtc acttccagcc actacccatc ctcaagagtg agcattgtcc    13320
tgacttctaa caacaaggat taactttgct tgttttgtc ctttatgtaa atggactcat      13380
atactaagta ttcttgtgag tagcttcttt cactcaacaa catgtttatg tgctttatcc    13440
atactcttgt gtatatataa aactcttatt gttatttagt attccatttt gtgaatataa    13500
cccaatttat tatgcattct accttgtgtg gattctgttt ctttttttgtg cagcttcaga    13560 caagcagact ctgttgccca atgaccagct ctaccaggta aggggatgaa gaataaaaga    13620
gacattgctg taattagtgg gggtaaatct ttgggattga gggcatgtt atttggaaga      13680 tcctatacag gtaagaaact gctaacagca taccagatga tgagatcagt ttgggtagaa    13740
taaatgaact aaagagaagg attgacagag actgaggtca ggatctagtg agcacaagtt    13800
gaagaacaca ctgagaggga cacacgaaga aactctcgac aggctgggca ctcactatag    13860
acaggccatg gctcatgcct gtaatcccag cactttggga agccaaaaca ggtgaatcac    13920
```

```
ctgaggtcag gaattcgaga caagcctggc caacatgatg aaactctgtc tctactaaaa    13980
atacaaaaaa aattaaccag gcgtggaggc gcgcgcctgt agtcccagct actcaggagg    14040
ctgaggcagg aggaccactt gaacccagga ggtcgaggtt gcagtgagct gcgattgtgc    14100
cactgcactc cagcctgggc aacagagaaa gactccgtct caaaaaaaaa aaagagagag    14160
agagaaaaag aaaaaagaca gagcctccat ctccttgtcc tctttccatc ctcaggacca    14220
tgaagtaccc actccaaatt ctcacatata aaaacattc aataaacatg catcaaatta     14280
attaatagag gatggaaaaa atgacttatg actgtgctgt cctttccagc ccctcaagga    14340
tcgagaagat gaccagtaca gccaccttca aggaaaccag ttgaggagga attgaactca    14400
ggactcagag taggtgggtt cttcaatgcc aattctaata aaggacccctt gcatcaactg    14460 ccctcgcaat tgcttctaag tctagctccc ttccctaagc ggctataagc atcagactct    14520
ggggatcagg gattgggacg tggtttgggg tactcttttc taaaaattct ggggccatac    14580
tgattgtctt ggcctaggta aatatgaatt ttatgtatct gtaaatcctg tcagagcagg    14640
gcctcaagcc atagagatgc tgaatattaa tcttaaccta catttgaatt tctcattatc    14700
tacactatta acattttggg ctaattaatt atttgtgatg aggggctagc ctgtgcattg    14760
taggagttat ggaagcatcc ctggcctctc tccaccagat gctggtagat tgtccagtgt    14820
gacaatcaaa aatgtgtcca gacattacca aatgtgtcca acatcaccct ccagggcaaa    14880
atcaccctta gttaagaacc actaacccat attaaccttc caatcaataa atcaatcagt    14940
cagaagttat gatttaatta atctatctga gtttctatc aggaagacag ggttgaaagc     15000
attatttgtt ttttttgaac aaattgcaat ttttctttt tcagtccagg tgttctcctc     15060
ctattcagtt cccagaatca aagcaatgca ttttggaaag ctcctagcag agagactttc    15120
agccctaaat ctagactcaa ggttcccaga gatgacaaat ggagaagaaa ggccatcaga    15180
gcaaatttgg gggtttctca aataaaataa aaataaaaac aaatactgtg tttcagaagc    15240
gccacctatt ggggaaaatt gtaaagaaa atgaaaaga tcaaataacc ccctggattt      15300
gaatataatt ttttgtgttg taattttat ttcgtttttg tataggttat aattcacatg     15360
gctcaaatat tcagtgaaag ctctccctcc accgccatcc cctgctaccc agtgaccctg    15420
ttgccctctt cagagacaaa ttagtttctc ttttttttt ttttttttt tttttgaga        15480 cagtctggct ctgtcaccca ggctgaaatg cagtggcacc atctcggctc actgcaacct    15540
ctgcctcctg ggttcaagcg attctcctgc ctcagcctcc cgggcagctg ggattacagg    15600
cacacactac cacacctggc taatttttgt attttttagta gagacagggt tttgctctgt   15660
tggccaagct ggtctcgaac tcctgacctc aagtgatccg cccgcctcag cctcccaaag    15720
tgctgggatt acaggtgtga gccaccatgc ctggtcttaa aaccagtttc ttatatatct    15780
ctctggaggt attctaggca tatatgagca cattctcaag tacatattat cctccctttcc   15840 cctatctttt agacaaatga tatcaaacta tacatcttgt gagattattg cataccatta    15900
tatgaagata ccattatatc ctttttaatg caaccatatt gtacaaatag actatgattt    15960
atttaacctg ttatctatca gtggatattt aagttggtag ttggttccaa tcttttgctc    16020
ttacaacaat tctgcaatga ctaacattgt ataaatatca ttttaaaaa taattgcatt     16080 gaagcataat gtacatgcca taaatccac ccatcttaag tgatttcacc tgttctcaga     16140 aattttttagt aaatttaact aattgtacag ccattaccat aatccagctt taggacattt   16200 tcttttttttt cttttcttt cttttttttc tttttttttt tttttgaag tggaatcttg     16260 ctctgtggcc caggctggag tgcagtggcg cgatctcagc tcactgcaac ctccacctcc    16320
```

```
tgggttcaag cgattctctt gccttggcct cccgagtagc tgagactaca ggcacatgcc    16380
accacgccca gctcattttt tgtgtattta gtatttgtgt atctagtatt tgtgtactta    16440
gtagagacag ggtttcacca tgttggccag gctggtctcc aattcctgac ctcaggcgat    16500
c                                                                   16501

<210> SEQ ID NO 2
<211> LENGTH: 50
<212> TYPE: DNA
<213> ORGANISM: Homo sapiens

<400> SEQUENCE: 2
agctgctgca caggctggct ggctggctgg ctgctaaggg ctgctccacg               50

<210> SEQ ID NO 3
<211> LENGTH: 50
<212> TYPE: DNA
<213> ORGANISM: Homo sapiens

<400> SEQUENCE: 3
cggaaaaaca aaaggcatct gcacctgcag ccctgctgag gcccctgctg               50

<210> SEQ ID NO 4
<211> LENGTH: 50
<212> TYPE: DNA
<213> ORGANISM: Homo sapiens

<400> SEQUENCE: 4
acccaggctg atagttcggt gacctggctt tatctactgg atgagttccg               50

<210> SEQ ID NO 5
<211> LENGTH: 50
<212> TYPE: DNA
<213> ORGANISM: Homo sapiens

<400> SEQUENCE: 5
tggaacatag cacgtttctc tctggcctgg tactggctac ccttctctcg               50

<210> SEQ ID NO 6
<211> LENGTH: 435
<212> TYPE: DNA
<213> ORGANISM: Homo sapiens

<400> SEQUENCE: 6
ttattccacc tattaccttc caaacgcctc tttcataatc tcaaaaaaat aataaaacca    60
aataccgtat ctcacgccta taatcccaac actttaaaaa actaaacaa ataaatcaca    120 aaatcaaaaa ttcgaaacca acctaaccaa caaaataaaa ccccgtctct actaaaaata    180
caaaaattaa ccgaacttac taacacgcac ctataatctc aactactcaa aaaactaaaa    240
caaaaaaatc gcttaaaccc cgaaaataaa aattacaata aactaaaata acgccactac    300
actccaacct aaacaacaaa ataaaactct atctcaaaaa aaaaaaaaaa aaaaaaaata    360
aaaaaaattc ctaaataaaa acctaaacta aataaacttt ccatttaaaa atccaacccc    420
aaacatctaa aaatc                                                    435

<210> SEQ ID NO 7
<211> LENGTH: 438
<212> TYPE: DNA
<213> ORGANISM: Homo sapiens
```

```
<400> SEQUENCE: 7
ataaacctca ctcccatcaa taatatccct ctcaaatccc ttcccccacc cacctaaaat      60
aaccttacct tacgaaaaaa aaataaccaa taccaaacca aaaaaaaacg tactatattc     120
catctcccaa cgaaactcat ccaataaata aaccaaatc accgaactat caacctaaat      180
aaaaactacc ctcccctaac taactcacaa ataccgaaaa aaaaaaaata aaaaaaaaac     240
taaaaaatat ctacttctct actttctacc gttaataata aaaaattttc aaaataaaaa     300
taaactaaaa ataaaataaa aaaaaaacga tataaattac tctatctcta aacaaaaaac    360
taacaaaaaa tataaaaaaa ataacctaaa ctttaacgtc cctattaaca atacaaccac    420
atttacacac aacctaaa                                                   438

<210> SEQ ID NO 8
<211> LENGTH: 472
<212> TYPE: DNA
<213> ORGANISM: Homo sapiens

<400> SEQUENCE: 8
aatccctcct aaaattcatta cctacaacaa caacaactaa caacaaataa caactaacta      60
cgatcctaac aactaataac aaaaacattt atctccctca taaaaaaacg atcccaaaac     120
catctcccac ccaacatcca ttacgattcc ctatacaaaa taaatctcta ataaaaaatc     180
caacactctc tccctcttct tccccaccac cttcaccctc cttaacgaaa aaacaaaaaa     240
catctacacc tacaaccta ctaaaacccc tactactcac acttacaaca aaaaataaaa      300
actctaaatt cttaccttct ctcaaaaacc ccaaccccaa caataataaa taaaaccaat    360
ctaactacta cacaaactaa ctaactaact aactactaaa aactactcca cgctttacc    420 gaaaaacaaa aactaacata aaacaaaaaa aaaacctaac tatcctcatc ct            472

<210> SEQ ID NO 9
<211> LENGTH: 50
<212> TYPE: DNA
<213> ORGANISM: Homo sapiens

<400> SEQUENCE: 9
agtcatctgt tttgcttttt ttccagaagt agtaagtctg ctggcctccg               50

<210> SEQ ID NO 10
<211> LENGTH: 50
<212> TYPE: DNA
<213> ORGANISM: Homo sapiens

<400> SEQUENCE: 10
cgcccagcct cgctgttctt atcttggcag cagattccga atgtcggctg               50

<210> SEQ ID NO 11
<211> LENGTH: 50
<212> TYPE: DNA
<213> ORGANISM: Homo sapiens

<400> SEQUENCE: 11
cgctcatcag gacttcagca ctgcccgtcc atggggacgt ctgcactcac               50

<210> SEQ ID NO 12
<211> LENGTH: 50
<212> TYPE: DNA
<213> ORGANISM: Homo sapiens

<400> SEQUENCE: 12
```
cgccttgagc tgtacctggc acatctttgt tgctcagcaa agagtggttg            50

<210> SEQ ID NO 13
<211> LENGTH: 50
<212> TYPE: DNA
<213> ORGANISM: Homo sapiens

<400> SEQUENCE: 13
tcttcccatc tgcgtcttgg ttaaggactt ttatcgtatc ctgtttatcg            50

<210> SEQ ID NO 14
<211> LENGTH: 50
<212> TYPE: DNA
<213> ORGANISM: Homo sapiens

<400> SEQUENCE: 14
aagatctgct ggaggccagg cacagacagg tgctttaact caagttatcg            50

<210> SEQ ID NO 15
<211> LENGTH: 50
<212> TYPE: DNA
<213> ORGANISM: Homo sapiens

<400> SEQUENCE: 15
agtaactgca gcaatgagtg cccgggctgt gcttggagta ccagtgctcg            50

<210> SEQ ID NO 16
<211> LENGTH: 50
<212> TYPE: DNA
<213> ORGANISM: Homo sapiens

<400> SEQUENCE: 16
cgccccaagt actaagtggc acagcttggt gagcaaggac attttttattg           50

<210> SEQ ID NO 17
<211> LENGTH: 50
<212> TYPE: DNA
<213> ORGANISM: Homo sapiens

<400> SEQUENCE: 17
cggcaagatg aaacaagctt attaggctct gtcttttaag ggcataccag            50

<210> SEQ ID NO 18
<211> LENGTH: 50
<212> TYPE: DNA
<213> ORGANISM: Homo sapiens

<400> SEQUENCE: 18
cgcaacacag ggctgcctcc cccggtatat gggccccact ccacagaggt            50

<210> SEQ ID NO 19
<211> LENGTH: 50
<212> TYPE: DNA
<213> ORGANISM: Homo sapiens

<400> SEQUENCE: 19
cggcagagca cacagctgca gaagtaaaaa ggattgaaac atttggatcc            50

<210> SEQ ID NO 20
<211> LENGTH: 50
<212> TYPE: DNA
<213> ORGANISM: Homo sapiens

<400> SEQUENCE: 20
acccaggctg atagttcggt gacctggctt tatctactgg atgagttccg            50

<210> SEQ ID NO 21
<211> LENGTH: 50
<212> TYPE: DNA
<213> ORGANISM: Homo sapiens

<400> SEQUENCE: 21
tggaacatag cacgtttctc tctggcctgg tactggctac ccttctctcg            50

<210> SEQ ID NO 22
<211> LENGTH: 50
<212> TYPE: DNA
<213> ORGANISM: Homo sapiens

<400> SEQUENCE: 22
agctgctgca caggctggct ggctggctgg ctgctaaggg ctgctccacg            50

<210> SEQ ID NO 23
<211> LENGTH: 50
<212> TYPE: DNA
<213> ORGANISM: Homo sapiens

<400> SEQUENCE: 23
cggaaaaaca aaaggcatct gcacctgcag ccctgctgag gcccctgctg            50

<210> SEQ ID NO 24
<211> LENGTH: 50
<212> TYPE: DNA
<213> ORGANISM: Homo sapiens

<400> SEQUENCE: 24
agtcatctgt tttgcttttt ttccagaagt agtaagtctg ctggcctccg            50

<210> SEQ ID NO 25
<211> LENGTH: 50
<212> TYPE: DNA
<213> ORGANISM: Homo sapiens

<400> SEQUENCE: 25
cgctgcagtc agactccaaa gtcaggaacg tgagggctac catctctcaa            50

<210> SEQ ID NO 26
<211> LENGTH: 50
<212> TYPE: DNA
<213> ORGANISM: Homo sapiens

<400> SEQUENCE: 26
cgaaggcccc cagctgtggg agcccacgct atttattggt gatcaaagaa            50

<210> SEQ ID NO 27
<211> LENGTH: 50
<212> TYPE: DNA
<213> ORGANISM: Homo sapiens

<400> SEQUENCE: 27
cgcaggcact tacgatcctg ccgtcgccag agcccagatc caccgttttt            50

<210> SEQ ID NO 28
<211> LENGTH: 50
<212> TYPE: DNA
<213> ORGANISM: Homo sapiens

```
<400> SEQUENCE: 28
gggctcccgg gctgggcagg taaggagcgc tggtattggg ggcgcaggcg         50

<210> SEQ ID NO 29
<211> LENGTH: 50
<212> TYPE: DNA
<213> ORGANISM: Homo sapiens

<400> SEQUENCE: 29
ttccgcccac aatttctga taacagcctt caaggcctca gttgctgtcg          50

<210> SEQ ID NO 30
<211> LENGTH: 50
<212> TYPE: DNA
<213> ORGANISM: Homo sapiens

<400> SEQUENCE: 30
cgggaccctg ttgctgactg ctcaagagga ggcaagctgg atctctctta         50

<210> SEQ ID NO 31
<211> LENGTH: 50
<212> TYPE: DNA
<213> ORGANISM: Homo sapiens

<400> SEQUENCE: 31
taaatgatgt cttggggctg tggcccgagc tgcctcaggt agatcccacg         50

<210> SEQ ID NO 32
<211> LENGTH: 50
<212> TYPE: DNA
<213> ORGANISM: Homo sapiens

<400> SEQUENCE: 32
ggggactgtg ggtcctctta ggggctgtga cgctgctatt tctcatctcg         50

<210> SEQ ID NO 33
<211> LENGTH: 50
<212> TYPE: DNA
<213> ORGANISM: Homo sapiens

<400> SEQUENCE: 33
cgcactcagc aaggcctcct gccctgagag aggctccgcc cactaccccc         50

<210> SEQ ID NO 34
<211> LENGTH: 50
<212> TYPE: DNA
<213> ORGANISM: Homo sapiens

<400> SEQUENCE: 34
ctcatgaagc aaggtctgcc tctacttctg tgatgtggtt catgtttccg         50

<210> SEQ ID NO 35
<211> LENGTH: 50
<212> TYPE: DNA
<213> ORGANISM: Homo sapiens

<400> SEQUENCE: 35
gacctttagc ctcaaactcc cgtggtggaa acagttagga ttggtggacg         50

<210> SEQ ID NO 36
<211> LENGTH: 50
<212> TYPE: DNA
```

<213> ORGANISM: Homo sapiens

<400> SEQUENCE: 36
gagagacaat acccttccaa aatacacttc aacataaagt tttcttttcg    50

<210> SEQ ID NO 37
<211> LENGTH: 50
<212> TYPE: DNA
<213> ORGANISM: Homo sapiens

<400> SEQUENCE: 37
cggtatacct gccctacttc ggtatagtcc ttggcacatg gcaggcactc    50

<210> SEQ ID NO 38
<211> LENGTH: 50
<212> TYPE: DNA
<213> ORGANISM: Homo sapiens

<400> SEQUENCE: 38
atggtagccc cttctgcggg gagcacacaa cagtcttcag ttcttctgcg    50

<210> SEQ ID NO 39
<211> LENGTH: 402
<212> TYPE: DNA
<213> ORGANISM: Homo sapiens

<400> SEQUENCE: 39
agcctcttta taatctcaaa aaataataa aaccaaatac cgtatctcac gcctataatc    60
ccaacacttt aaaaaactaa aacaaataaa tcacaaaatc aaaaattcga aaccaaccta    120
accaacaaaa taaaaccccg tctctactaa aaatacaaaa attaaccgaa cttactaaca    180
cgcacctata atctcaacta ctcaaaaaac taaaacaaaa aaatcgctta aaccccgaaa    240
ataaaaatta caataaacta aaataacgcc actacactcc aacctaaaca acaaaataaa    300
actctatctc aaaaaaaaaa aaaaaaaaaa aaaaaaaaaa attttctaaaa aaaaacccaa    360
aaaaaaaaaa cttttccttt aaaaaacccc ccccaaaaat tt    402

<210> SEQ ID NO 40
<211> LENGTH: 394
<212> TYPE: DNA
<213> ORGANISM: Homo sapiens

<400> SEQUENCE: 40
agcctcttta taatctcaaa aaataataa aaccaaatac cgtatctcac gcctataatc    60
ccaacacttt aaaaaactaa aacaaataaa tcacaaaatc aaaaattcga aaccaaccta    120
accaacaaaa taaaaccccg tctctactaa aaatacaaaa attaaccgaa cttactaaca    180
cgcacctata atctcaacta ctcaaaaaac taaaacaaaa aaatcgctta aaccccgaaa    240
ataaaaatta caataaacta aaataacgcc actacactcc aacctaaaca acaaaataaa    300
actctatctc aaaaaaaaaa aaaaaaaaaa aaaaaaaaaa atttccaaaa aaaaacccaa    360
aaaaaaaaaa ctttcccttt aaaaaacccc cccc    394

<210> SEQ ID NO 41
<211> LENGTH: 435
<212> TYPE: DNA
<213> ORGANISM: Homo sapiens

<400> SEQUENCE: 41
ttattccacc tattaccttc caaacgcctc tttcataatc tcaaaaaaat aataaaacca    60

```
aataccgtat ctcacgccta taatcccaac actttaaaaa actaaaacaa ataaatcaca        120
aaatcaaaaa ttcgaaacca acctaaccaa caaaataaaa ccccgtctct actaaaaata        180
caaaaattaa ccgaacttac taacacgcac ctataatctc aactactcaa aaaactaaaa        240
caaaaaaatc gcttaaaccc cgaaaataaa aattacaata aactaaaata acgccactac        300
actccaacct aaacaacaaa ataaaactct atctcaaaaa aaaaaaaaaa aaaaaaaata        360
aaaaaaattc ctaaataaaa acctaaaacta aaataacttt ccatttaaaa atccaacccc       420
aaacatctaa aaatc                                                        435

<210> SEQ ID NO 42
<211> LENGTH: 399
<212> TYPE: DNA
<213> ORGANISM: Homo sapiens

<400> SEQUENCE: 42 cgcctctttta taatctcaaa aaataataa aaccaaatac cgtatctcac gcctataatc        60
ccaacacttt aaaaaactaa aacaaataaa tcacaaaatc aaaaattcga accaaaccta       120
accaacaaaa taaaaccccg tctctactaa aaatacaaaa attaaccgaa cttactaaca       180
cgcacctata atctcaacta ctcaaaaaac taaaacaaaa aaatcgctta aaccccgaaa       240
ataaaaatta caataaacta aaataacgcc actacactcc aacctaaaca acaaaataaa       300
actctatctc aaaaaaaaaa aaaaaaaaaa aaaaaaaaaa atttccaaaa aaaaacccaa       360
aaaaaaaaaa ctttcccttt aaaaaacccc ccccaaaaa                              399

<210> SEQ ID NO 43
<211> LENGTH: 394
<212> TYPE: DNA
<213> ORGANISM: Homo sapiens

<400> SEQUENCE: 43 tacctctttta taaatctcaa aaaataata aaaccaaata ccatatctca cacctataat        60
cccaacactt taaaaaacta aaacaaataa atcacaaaat caaaaattca aaaccaacct       120
aaccaacaaa ataaaacccc atctctacta aaaatacaaa aattaaccaa acttactaac       180
acacacctat aatctcaact actcaaaaaa ctaaaacaaa aaaatcactt aaaccccaaa       240
aataaaaatt acaataaact aaaataacac cactacactc caacctaaac aacaaaataa       300
aactctatct caaaaaaaaa aaaaaaaaaa aaaaaaaaaa aatttccaaa aaaaaaccca       360
aaaaaaaaaa actttccctt taaaaacccc cccc                                   394

<210> SEQ ID NO 44
<211> LENGTH: 396
<212> TYPE: DNA
<213> ORGANISM: Homo sapiens

<400> SEQUENCE: 44 gacctctttta taatctcaaa aaataataa aaccaaatac catatctcac acctataatc        60
ccaacacttt aaaaaactaa aacaaataaa tcacaaaatc aaaaattcaa accaaaccta       120
accaacaaaa taaaacccca tctctactaa aaatacaaaa attaaccaaa cttactaaca       180
cacacctata atctcaacta ctcaaaaaac taaaacaaaa aaatcactta aaccccaaaa       240
ataaaaatta caataaacta aaataacacc actacactcc aacctaaaca acaaaataaa       300
actctatctc aaaaaaaaaa aaaaaaaaaa aaaaaaaaaa atttccaaaa aaaaacccaa       360
```

```
aaaaaaaaaa ctttcccttt aaaaaccccc ccccaa                              396
```

<210> SEQ ID NO 45
<211> LENGTH: 387
<212> TYPE: DNA
<213> ORGANISM: Homo sapiens

<400> SEQUENCE: 45

```
cgcctcttta tatctaaaaa aatataaacc aataccgtat ctcacaccta taatcccaac    60
acttaaaaaa ctaaaacaaa taaatcacaa aatcaaaaat tcagaaacca acctaaccaa   120
caaaataaaa ccccgtctct actaaaaata caaaaattaa ccaaacttac taacacacac   180
ctataatctc aactactcaa aaaactaaaa caaaaaaatc acttaaaccc caaaaataaa   240
aattacaata aactaaaata acaccactac actccaacct aaacaacaaa ataaaactct   300
atctcaaaaa aaaaaaaaaa aaaaaaaaaa aaaaaatttc caaaaaaaaa cccaaaaaaa   360
aaaaactttc cctttaaaaa accccccc                                      387
```

<210> SEQ ID NO 46
<211> LENGTH: 391
<212> TYPE: DNA
<213> ORGANISM: Homo sapiens

<400> SEQUENCE: 46

```
atgattgtta atagggacgt taaagtttag gttatttttt ttatattttt tgttagtttt    60
ttgtttagag atagagtaat ttatatcgtt ttttttttat tttatttttta gtttattttt   120
attttgaaaa ttttttatta ttaacggtag aaagtagaga agtagatatt ttttagtttt   180
ttttttatttt ttttttttttc ggttttgggg atttatttag ggggggtgt ttttttttg    240
ggttgatagt tcgggatttt ggtttttattt atggaggatt ttccgtgggg aaaggaaaaa   300
aaaacctttt tttttgggtt gggtttgggt tatttttttt ccgaagggaa aggttttta   360
agggggggggg ggaaagggtt ttaaaaggaa a                                  391
```

<210> SEQ ID NO 47
<211> LENGTH: 328
<212> TYPE: DNA
<213> ORGANISM: Homo sapiens

<400> SEQUENCE: 47

```
ctatttgatg ggagaagtga ggtgttaata agtttaggtt atttttttta tattttttgt    60
tagttttttg tttagagata gagtaatta tattgttttt ttttatttt atttttagtt    120
tattttttatt ttgaaaattt tttattatta atggtagaaa gtagagaagt agatatttttt   180
tagtttttttt tttatttttt tttttgggtt ttttgggatt tatttggggg gggtgttttt   240
tttttgggt tgatatttgg gggattgggt tttttaatg ggaggattttt tgtgggaaa   300
ggaaataaaa tttttttttt ttgggttg                                      328
```

<210> SEQ ID NO 48
<211> LENGTH: 388
<212> TYPE: DNA
<213> ORGANISM: Homo sapiens

<400> SEQUENCE: 48

```
ctatttgatg ggagaagtga ggttgttaat aagtttaggt tatttttttt atattttttg    60
ttagtttttt gtttagagat agagtaattt atattgtttt tttttatttt tattttttagt   120
ttatttttat tttgaaaatt tttattatt aatggtagaa agtagagaag tagatatttt   180
```

```
ttagtttttt ttttatttttt tttttttggg attttggaat taattaaggg gggggaattt    240
tttttttagg ttgaaatttg ggggattggg ttttatttttt gggaggattt ttgtggggaa    300
aggaaaaaaa ttttttttt tttgggttgg gtttgggttt ttttttttg gaagggaagg      360 gttttttgg ggggggggggg aagggggtt                                       388
```

<210> SEQ ID NO 49
<211> LENGTH: 401
<212> TYPE: DNA
<213> ORGANISM: Homo sapiens

<400> SEQUENCE: 49

```
cattgatggg aagtagagga ttgataaagt ttaggttatt ttttttatat tttttgttag     60 tttttttgttt agagatagag taatttatat tgttttttttt ttattttatt tttagtttat   120 ttttatttttg aaaatttttt attattaatg gtagaaagta gagaagtaga tatttttttag  180 tttttttttt attttttttt tttgggtttt tggaattaat ttgggggggg gaatttttttt   240 tttaggtgga aatttggggg attgggtttt atttatggga gaattttttgt ggggaaagga   300 aataaatttt tttttttttg ggttgggttt gggttttttt tttttgggag ggaagggttt    360 ttttggggggg ggggggggagg ggtttaaagg aattttttgg g                      401
```

<210> SEQ ID NO 50
<211> LENGTH: 387
<212> TYPE: DNA
<213> ORGANISM: Homo sapiens

<400> SEQUENCE: 50

```
attggtatgt gttaagtatg ggatgtgtaa agtttaggtt attttttttta tatttttttgt  60 tagttttttg tttagagata gagtaattta tattgtttttt tttttatttt attttttagtt  120 tattttttatt ttgaaaattt tttattatta atggtagaaa gtagagaagt agatattttt   180 tagtttttttt tttatttttt ttttttgggt ttttggaatt aattaagggg ggggaattt    240 tttttaaggt ggaaagttgg gggattgggt tttatttatg ggaggatttt tgtggggaaa   300
ggaaaaaaat tttttttttt ttgggttggg tttgggtttt ttttttttgg aagggaaggg   360
tttttttggg ggggggggga aggggtt                                       387
```

<210> SEQ ID NO 51
<211> LENGTH: 420
<212> TYPE: DNA
<213> ORGANISM: Homo sapiens

<400> SEQUENCE: 51

```
attgttaata gggacgttaa agtttaggtt attttttttta tatttttttgt tagtttttttg  60 tttagagata gagtaattta tatcgttttt tttttatttt attttttagtt tattttttatt  120 ttgaaaattt tttattatta acggtagaaa gtagagaagt agatattttt tagtttttttt   180 tttatttttt tttttccgga atttgtgagt tagtaggggg agggtagttt ttatttaggt   240
tgatagttcg gtgatttggt ttaatttatt gaatgagttt cgttggggag atgaaatata   300
gtacggtttt ttttttggttt gggtatgggt attttttttt cggaaagggt aaagggtatt  360
ttaggtgggg tggggggaaag ggattttgga gagggattat attgatgggg agtgaaggtt  420
```

<210> SEQ ID NO 52
<211> LENGTH: 416
<212> TYPE: DNA

<213> ORGANISM: Homo sapiens

<400> SEQUENCE: 52

| tatccctctc aaatcccttc ccccacccac ctaaaataac cttaccttac gaaaaaaaaa | 60 |
| taaccaatac caaaccaaaa aaaaacgtac tatattccat ctcccaacga aactcatcca | 120 |
| ataaataaaa ccaaatcacc gaactatcaa cctaaataaa aactaccctc ccctaactaa | 180 |
| ctcacaaata ccgaaaaaaa aaaaataaaa aaaaacctaa aaaattttc cttctttcct | 240 |
| ttctcccgtt aaaaaaaaaa aatttttcaaa aaaaaaataa cctaaaaaaa aaaaaaaaaa | 300 |
| aaaccgtttt aatttccttt tttttaacc aaaaaattaa caaaaatttt aaaaaaaata | 360 |
| cccaaaattt taccgcccct ttaaacaatc cacccacttt tccccacacc taaaaa | 416 |

<210> SEQ ID NO 53
<211> LENGTH: 416
<212> TYPE: DNA
<213> ORGANISM: Homo sapiens

<400> SEQUENCE: 53

| tatccctctc aaatcccttc ccccacccac ctaaaataac cttaccttac gaaaaaaaaa | 60 |
| taaccaatac caaaccaaaa aaaaacgtac tatattccat ctcccaacga aactcatcca | 120 |
| ataaataaaa ccaaatcacc gaactatcaa cctaaataaa aactaccctc ccctaactaa | 180 |
| ctcacaaata ccgaaaaaaa aaaaataaaa aaaaactaa aaaattttc cttctttcct | 240 |
| ttctcccgtt aaaaaaaaaa aatttttcaaa aaaaaaataa cctaaaaata aaaaaaaaaa | 300 |
| aaaccgtttt aatttccttt tttttaacc aaaaaacttaa caaaaatttt aaaaaaaaaa | 360 |
| ccctaacttt taccgcccct ttaaacaatc caccccttt tccccccacc ctaaaa | 416 |

<210> SEQ ID NO 54
<211> LENGTH: 418
<212> TYPE: DNA
<213> ORGANISM: Homo sapiens

<400> SEQUENCE: 54

| gtatccctct caaatccctt ccccacccca cctaaaataa ccttaccttta cgaaaaaaaa | 60 |
| ataaccaata ccaaaccaaa aaaaacgta ctatattcca tctcccaacg aaactcatcc | 120 |
| aataaataaa accaaatcac cgaactatca acctaaataa aaactaccct ccctaacta | 180 |
| actcacaaat accgaaaaaa aaaaaataaa aaaaaacta aaaattttt tttttttttt | 240 |
| tttttcccgt taataaaaaa aattttttaaa aataaaaata acctaaaaat aaaataaaaa | 300 |
| aaaccgtttt taatttcctt ttttttaac caaaaactta ccaaaaaatt taaaaaaaat | 360 |
| accctaactt ttaccgcccc tttaaaaaaa ccaccccctt tcccccccac ccaaaaaa | 418 |

<210> SEQ ID NO 55
<211> LENGTH: 419
<212> TYPE: DNA
<213> ORGANISM: Homo sapiens

<400> SEQUENCE: 55

| gccatcttac ccacaacccct taaccccacc cacctaaaat aaccttacct tacaaaaaaa | 60 |
| aaataaccaa taccaaacca aaaaaaaaca tactatattc catctcccaa caaaactcat | 120 |
| ccaataaata aaaaccaaatc accaaactat caacctaaat aaaaactacc ctccctaac | 180 |
| taactcacaa atcccaaaaa aaaaaaaata aaaaaaaacc taaaattttt ttttttcttt | 240 |
| cttttcccc tttaaaaaaa aaaattttta aaaaaaaaaa aaacctaaaa aaaaaaaaaa | 300 |

```
aaaaaaccat tttaatttct ttttttttta accaaaaact tacaaaaaat tttaaaaaaa    360
aaccccaaac tttaaccccc cttttaaaaa aaccccccct ttttccccccc cccaaaaa     419
```

<210> SEQ ID NO 56
<211> LENGTH: 418
<212> TYPE: DNA
<213> ORGANISM: Homo sapiens

<400> SEQUENCE: 56

```
gccatcttac ccacaaccct aaccccaccc acctaaaata accttacctt acaaaaaaaa    60
aataaccaat accaaaccaa aaaaaaacat actatattcc atctcccaac aaaactcatc   120
caataaataa aaccaaatca ccaaactatc aacctaaata aaaactaccc tcccctaact   180
aactcacaaa tcccaaaaaa aaaaaaataa aaaaaaacct aaaaattttc tctttctctc   240
ttttccccct aaaaaaaaaa aaattttttaa aaaaaaaaaa aacctaaaaa aaaaaaaaaa   300
aaaaaccatt ttaatttctt ttttttttaa caaaaaactt acaaaaaatt ttaaaaaaaa   360
aacccaaact tttacccccc ttttaaaaaa accccccct tttccccccc cccaaaaa     418
```

<210> SEQ ID NO 57
<211> LENGTH: 419
<212> TYPE: DNA
<213> ORGANISM: Homo sapiens

<400> SEQUENCE: 57

```
tatatcctac tcaacatccc tatcccccac ccacctaaaa taaccttacc ttacaaaaaa    60
aaaataacca ataccaaacc aaaaaaaaac atactatatt ccatctccca acaaaactca   120
tccaataaat aaaaccaaat caccaaacta tcaacctaaa taaaaactac cctcccctaa   180
ctaactcaca atcccaaaa aaaaaaaaaa aaaaaaaaac ctaaaaattt tttcttttt    240 tcttttttccc cttaaaaaaa aaaattttt aaaaaaaaaa aaaacctaaa aaaaaaaaa    300 aaaaaaaacct ttttaatttc tcctttcttt aaccaaaaac ttaccaaaaa ttttaaaaaa   360
aatccccaaa ttttaacccc ccttttaaaa aaaccacccc tttttccccc ccccaaaa     419
```

<210> SEQ ID NO 58
<211> LENGTH: 416
<212> TYPE: DNA
<213> ORGANISM: Homo sapiens

<400> SEQUENCE: 58

```
catccctctc taatcccttc ccccacccac ctaaataaac cttaccttac aaaaaaaaa    60 taaccaatac caaaccaaaa aaaacatac tatattccat ctcccaacaa aactcatcca   120
ataaataaaa ccaaatcacc aaactatcaa cctaaataaa aactaccctc ccctaactaa   180
ctcacaaatc caaaaaaaaa aaaataaaa aaaacctaa aaaattttc ttttttcctt     240 tttccccta aaaaaaaaa attttaaaaa aaaaattaa cttaaaataa aaaaaaaaa      300 aaaccatttt aatttttttt tttttaaca aaaaacttac caaaaatttt aaaaaaaaac   360
cccaaacttt tacccccctt ttaaaaaacc cccccttttt tccccccccc caaaaa      416
```

<210> SEQ ID NO 59
<211> LENGTH: 438
<212> TYPE: DNA
<213> ORGANISM: Homo sapiens

<400> SEQUENCE: 59

| | |
|---|---|
| ctataacaac aacaactaac aacaaataac aactaactac aatcctaaca actaataaca | 60 |
| aaaacattta tctccctcat aaaaaaacaa tcccaaaacc atctcccacc caacatccat | 120 |
| tacaattccc tatacaaaat aaatctctaa ataaaaatcc aacactctct ccctcttctt | 180 |
| ccccaccacc ttcaccctcc ttaacaaaaa aacaaaaaac atctacacct acaaccctac | 240 |
| taaaacccct actactcaca cttacaacaa aaaataaaaa ctctaaattc ttaccttctc | 300 |
| tcaaaaccc caaccccaac aataataaat aaaaccaatc taactactac acaaactaac | 360 |
| taactaacta actacaaaaa actactcctt acttttacca aaaaacacaa actaacataa | 420 |
| aacaaaaaaa aaacctat | 438 |

<210> SEQ ID NO 60
<211> LENGTH: 442
<212> TYPE: DNA
<213> ORGANISM: Homo sapiens

<400> SEQUENCE: 60

| | |
|---|---|
| ctataacaac aacaactaac aacaaataac aactaactac aatcctaaca actaataaca | 60 |
| aaaacattta tctccctcat aaaaaaacaa tcccaaaacc atctcccacc caacatccat | 120 |
| tacaattccc tatacaaaat aaatctctaa ataaaaatcc aacactctct ccctcttctt | 180 |
| ccccaccacc ttcaccctcc ttaacaaaaa aacaaaaaac atctacacct acaaccctac | 240 |
| taaaacccct actactcaca cttacaacaa aaaataaaaa ctctaaattc ttaccttctc | 300 |
| tcaaaaccc caaccccaac aataataaat aaaaccaatc taactactac acaaactaac | 360 |
| taactaacta actacaaaaa actactcctt acttttacca aaaaacacaa actaacataa | 420 |
| aacaaaaaaa aaacctatct tt | 442 |

<210> SEQ ID NO 61
<211> LENGTH: 445
<212> TYPE: DNA
<213> ORGANISM: Homo sapiens

<400> SEQUENCE: 61

| | |
|---|---|
| ctataacaac aacaactaac aacaaataac aactaactac aatcctaaca actaataaca | 60 |
| aaaacattta tctccctcat aaaaaaacaa tcccaaaacc atctcccacc caacatccat | 120 |
| tacaattccc tatacaaaat aaatctctaa ataaaaatcc aacactctct ccctcttctt | 180 |
| ccccaccacc ttcaccctcc ttaacaaaaa aacaaaaaac atctacacct acaaccctac | 240 |
| taaaacccct actactcaca cttacaacaa aaaataaaaa ctctaaattc ttaccttctc | 300 |
| tcaaaaccc caaccccaac aataataaat aaaaccaatc taactactac acaaactaac | 360 |
| taactaacta actacaaaaa actactcctt acttttacca aaaaacacaa actaacataa | 420 |
| aacaaaaaaa aaacctatct ttcct | 445 |

<210> SEQ ID NO 62
<211> LENGTH: 437
<212> TYPE: DNA
<213> ORGANISM: Homo sapiens

<400> SEQUENCE: 62

| | |
|---|---|
| gtataacaac aacaactaac aacaaataac aactaactac aatcctaaca actaataaca | 60 |
| aaaacattta tctccctcat aaaaaaacaa tcccaaaacc atctcccacc caacatccat | 120 |
| tacaattccc tatacaaaat aaatctctaa ataaaaatcc aacactctct ccctcttctt | 180 |
| ccccaccacc ttcaccctcc ttaacaaaaa aacaaaaaac atctacacct acaaccctac | 240 |

```
taaaacccct actactcaca cttacaacaa aaaataaaaa ctctaaattc ttaccttctc    300
tcaaaaaccc caaccccaac aataataaat aaaaccaatc taactactac acaaactaac    360
taactaacta actacaaaaa actactcctt acttttacca aaaaacacaa actaacataa    420
aacaaaaaaa aaaccta                                                  437

<210> SEQ ID NO 63
<211> LENGTH: 450
<212> TYPE: DNA
<213> ORGANISM: Homo sapiens

<400> SEQUENCE: 63
tataacaaca caactaaca acaaataaca actaactacg atcctaacaa ctaataacaa     60
aaacatttat ctccctcata aaaaaacgat cccaaaacca tctcccaccc aacatccatt   120
acgattccct atacaaaata aatctctaaa taaaaatcca acactctctc cctcttcttc   180
cccaccacct tcaccctcct taacgaaaaa acaaaaaaca tctacaccta caaccctact   240
aaacccccta ctactcacac ttacaacaaa aaataaaaac tctaaattct taccttctct   300
caaaaacccc aaccccaaca ataataaata aaaccaatct aactactaca caaactaact   360
aactaactaa ctactaaaaa ctactgcacg cttttaccga aaaacacaaa ctaacataaa   420
acaaaaaaaa aacctatctt tccccaacct                                    450

<210> SEQ ID NO 64
<211> LENGTH: 446
<212> TYPE: DNA
<213> ORGANISM: Homo sapiens

<400> SEQUENCE: 64
tataacaaca caactaaca acaaataaca actaactacg atcctaacaa ctaataacaa     60
aaacatttat ctccctcata aaaaaacgat cccaaaacca tctcccaccc aacatccatt   120
acgattccct atacaaaata aatctctaaa taaaaatcca acactctctc cctcttcttc   180
cccaccacct tcaccctcct taacgaaaaa acaaaaaaca tctacaccta caaccctact   240
aaacccccta ctactcacac ttacaacaaa aaataaaaac tctaaattct taccttctct   300
caaaaacccc aaccccaaca ataataaata aaaccaatct aactactaca caaactaact   360
aactaactaa ctactaaaaa ctactgcacg ctttgaccga aaaacaaaaa ctaacataaa   420
acaaaaaaaa aacctatctt tcccct                                        446

<210> SEQ ID NO 65
<211> LENGTH: 448
<212> TYPE: DNA
<213> ORGANISM: Homo sapiens

<400> SEQUENCE: 65
gataacaaca caactaaca acaaataaca actaactacg atcctaacaa ctaataacaa     60
aaacatttat ctccctcata aaaaaacgat cccaaaacca tctcccaccc aacatccatt   120
acgattccct atacaaaata aatctctaaa taaaaatcca acactctctc cctcttcttc   180
cccaccacct tcaccctcct taacgaaaaa acaaaaaaca tctacaccta caaccctact   240
aaacccccta ctactcacac ttacaacaaa aaataaaaac tctaaattct taccttctct   300
caaaaacccc aaccccaaca ataataaata aaaccaatct aactactaca caaactaact   360
aactaactac taacaactac ttactgcttg ctccgaccaa caaacactaa cttaaaacaa   420
```

```
aaaaaaaaca aacctatctt tctcccaa                                       448
```

<210> SEQ ID NO 66
<211> LENGTH: 382
<212> TYPE: DNA
<213> ORGANISM: Homo sapiens

<400> SEQUENCE: 66

```
ctgattgtta tagggacgtt aaagtttagg ttatttttt tatatttttt gttagttttt    60
tgtttagaga tagagtaatt tatatcgttt tttttttatt ttattttag tttattttta   120
ttttgaaaat ttttattat taacggtaga aagtagagaa gtagatattt tttagttttt   180
tttttatttt tttttttccg gttttgggaa ttaattaagg ggggggtatt tttttttag   240
gttgaaattc cggggattgg gttttattta tgggagaatt tccttgggga aaggaaaaaa   300
aaacctttt ttttgggttg ggtttgggtt attttttttc cgaagggaaa ggttttttaa   360
gggggggggg gaaagggttt tg                                           382
```

<210> SEQ ID NO 67
<211> LENGTH: 436
<212> TYPE: DNA
<213> ORGANISM: Homo sapiens

<400> SEQUENCE: 67

```
tttaggttgt gtgtaaatgt ggttgtattg ttaataggga cgttaaagtt taggttattt    60
tttttatatt ttttgttagt tttttgttta gagatagagt aatttatatc gttttttttt   120
tatttttattt ttagtttatt tttatttga aaattttta ttattaacgg tagaaagtag   180
agaagtagat attttttagt tttttttta tttttttttt ttcggtattt gtgagttagt   240
taggggaggg tagtttttat ttaggttgat agttcggtga tttggttta tttattggat   300
gagtttcgtt gggagatgga atatagtacg tttttttttg gtttggtatt ggttattttt   360
ttttcgtaag gtaaggttat tttaggtggg tggggaagg gatttgagag ggatattatt   420
gatgggagtg aggttt                                                  436
```

<210> SEQ ID NO 68
<211> LENGTH: 50
<212> TYPE: DNA
<213> ORGANISM: Homo sapiens

<400> SEQUENCE: 68

```
cgagagaagg gtagccagta ccaggccaga gagaaacgtg ctatgttcca              50
```

<210> SEQ ID NO 69
<211> LENGTH: 50
<212> TYPE: DNA
<213> ORGANISM: Homo sapiens

<400> SEQUENCE: 69

```
cgtggagcag cccttagcag ccagccagcc agccagcctg tgcagcagct              50
```

<210> SEQ ID NO 70
<211> LENGTH: 50
<212> TYPE: DNA
<213> ORGANISM: Homo sapiens

<400> SEQUENCE: 70

```
tgagagaagg gtagttagta ttaggttaga gagaaatgtg ttatgttta               50
```

```
<210> SEQ ID NO 71
<211> LENGTH: 50
<212> TYPE: DNA
<213> ORGANISM: Homo sapiens

<400> SEQUENCE: 71
cataaaacaa cccttaacaa ccaaccaacc aaccaaccta tacaacaact         50

<210> SEQ ID NO 72
<211> LENGTH: 50
<212> TYPE: DNA
<213> ORGANISM: Homo sapiens

<400> SEQUENCE: 72
caaaaaaaaa ataaccaata ccaaaccaaa aaaaaacata ctatattcca         50

<210> SEQ ID NO 73
<211> LENGTH: 50
<212> TYPE: DNA
<213> ORGANISM: Homo sapiens

<400> SEQUENCE: 73
tgtggagtag tttttagtag ttagttagtt agttagtttg tgtagtagtt         50

<210> SEQ ID NO 74
<211> LENGTH: 1978
<212> TYPE: DNA
<213> ORGANISM: Homo sapiens

<400> SEQUENCE: 74
caaataaacc tcactcccat caataatatc cctctcaaat cccttccccc acccacctaa     60
aataaccta ccttacaaaa aaaaaataac caataccaaa ccaaaaaaaa acatactata    120
ttccatctcc caacaaaact catccaataa ataaaaccaa atcaccaaac tatcaaccta    180
aataaaaact accctcccct aactaactca caaataccaa aaaaaaaaaa ataaaaaaaa    240
aactaaaaaa tatctacttc tctactttct accattaata ataaaaaatt ttcaaaataa    300
aaataaacta aaaataaaat aaaaaaaaaa caatataaat tactctatct ctaaacaaaa    360
aactaacaaa aaatataaaa aaaataacct aaactttaac atcccatatta acaatacaac    420
cacatttaca cacaacctaa acactaccac atctcaaaac cccttaaaaa aaaccatcaa    480
ccccataaca caaccataa caactaaatt tctcataaaa actaatcttt ctcaaaaccc    540
ttcactaaac aaccaaaaac accaaatcta acaacttctt atcaataaaa aattaaactt    600
taaaacccc aaccaaaaat ttaaatccta atccaatac tacctaccta taaaacctaa     660
accaaccata aaattttttca aaatcttatt ccattaatac cattattaaa attcaaacaa    720
aatatttaca taatacctca cacatcatat atactcatta aaaataatt attaataata    780
atataattaa ctaacaaaca atattaaacc tcccaataaa acaaataaac cttttccccc    840
tataacctac aaaaatctaa aactcttcac actactacaa ttaaactatc acttacctaa    900
aaacaaaatc atacctatct tactcactac tatatcttat acctaacaca taacaaaaac    960
tctacacatt tttattaact cactaactaa ctaactaaaa aaaataaaaa cctaaaatcc   1020
taaacattca atccaaactc taacccctaa aaatatacta acctatcctc aaaattattc   1080
cacctattac cttccaaaca cctctttcat aatctcaaaa aaataataaa accaaataccc  1140
atatctcaca cctataatcc caacacttta aaaaactaaa acaaataaat cacaaaatca   1200
aaaattcaaa accaacctaa ccaacaaaat aaaaccccat ctctactaaa aatacaaaaa   1260
```

```
ttaaccaaac ttactaacac acacctataa tctcaactac tcaaaaaact aaaacaaaaa   1320
aatcacttaa accccaaaaa taaaaattac aataaactaa aataacacca ctacactcca   1380
acctaaacaa caaaataaaa ctctatctca aaaaaaaaa aaaaaaaaa aataaaaaaa     1440 attcctaaat aaaaacctaa actaaaataa ctttccattt aaaaatccaa ccccaaacat   1500
ctaaaaatcc ctcctaaatt cattacctac aacaacaaca actaacaaca aataacaact   1560
aactacaatc ctaacaacta ataacaaaaa catttatctc cctcataaaa aaacaatccc   1620 aaaccatct cccacccaac atccattaca attccctata caaaataaat ctctaaataa     1680
aaatccaaca ctctctccct cttcttcccc accaccttca ccctccttaa caaaaaaaca   1740
aaaaacatct acacctacaa ccctactaaa accctactac tcacactta caacaaaaaa     1800 taaaaactct aaattcttac cttctctcaa aaacccaac cccaacaata taaataaaaa     1860
ccaatctaac tactacacaa actaactaac taactaacta ctaaaaacta ctccacactt   1920
ttaccaaaaa acaaaaacta acataaaaca aaaaaaaaac ctaactatcc tcatccta     1978

<210> SEQ ID NO 75
<211> LENGTH: 1978
<212> TYPE: DNA
<213> ORGANISM: Homo sapiens

<400> SEQUENCE: 75
caaataaacc tcactcccat caataatatc cctctcaaat cccttccccc acccacctaa     60
ataaccttta ccttacgaaa aaaaataac caataccaaa ccaaaaaaaa acgtactata    120
ttccatctcc caacgaaact catccaataa ataaaaccaa atcaccgaac tatcaaccta    180
aataaaaact accctcccct aactaactca caaataccga aaaaaaaaa ataaaaaaaa    240 aactaaaaaa tatctacttc tctactttct accgttaata ataaaaaatt ttcaaaataa    300 aaataaaacta aaaataaaat aaaaaaaaaa cgatataaat tactctatct ctaaacaaaa    360
aactaacaaa aaatataaaa aaaataacct aaactttaac gtccctatta acaatacaac    420
cacatttaca cacaacctaa acactaccac atctcgaaac cccttaaaaa aaaccgtcga    480
ccccataacg caaccgtaaa caactaaatt tctcataaaa actaatcttt ctcaaaaccc    540
ttcactaaac aaccaaaaac accaaatcta caacttctt atcaataaaa aattaaactt     600
taaaaacccc aaccaaaaat ttaaatccta atccaatac tacctaccta taaaacctaa    660
accaaccata aaattttttca aaatcttatt ccattaatac cattattaaa attcaaacaa    720
aatatttaca taatacctca cgcatcatat atactcatta aaaaataatt attaataata    780
atataattaa ctaacaaaca atattaaacc tcccgataaa acaaataaac cttttccccc    840
tataacctac gaaaatctaa aactcttcac gctactacaa ttaaactatc acttacctaa    900
aaacaaaatc ataccctatct tactcactac tatatcttat acctaacaca taacgaaaac    960
tctacacatt tttattaact cactaactaa ctaactaaaa aaaataaaaa cctaaaatcc   1020
taaacattca atccgaactc taacccctaa aaatatacta acctatcctc gaaattattc   1080
cacctattac cttccaaacg cctctttcat aatctcaaaa aaataataaa accaaatacc   1140
gtatctcacg cctataatcc caacacttta aaaaactaaa acaaataaat cacaaaatca   1200
aaaattcgaa accaacctaa ccaacaaaat aaaaccccgt ctctactaaa aatacaaaaa   1260
ttaaccgaac ttactaacac gcacctaaa tctcaactac tcaaaaaact aaaacaaaaa   1320
aatcgcttaa accccgaaaa taaaaattac aataaactaa aataacgcca ctacactcca   1380
acctaaacaa caaaataaaa ctctatctca aaaaaaaaa aaaaaaaaa aataaaaaaa     1440
```

```
attcctaaat aaaaacctaa actaaaataa ctttccattt aaaaatccaa ccccaaacat    1500
ctaaaaatcc ctcctaaatt cattacctac aacaacaaca actaacaaca aataacaact    1560
aactacgatc ctaacaacta ataacaaaaa catttatctc cctcataaaa aaacgatccc    1620
aaaaccatct cccacccaac atccattacg attcccatta caaaataaat ctctaaataa    1680
aaatccaaca ctctctccct cttcttcccc accaccttca ccctccttaa cgaaaaaaca    1740
aaaaacatct acacctacaa ccctactaaa acccctacta ctcacactta caacaaaaaa    1800
taaaaactct aaattcttac cttctctcaa aaaccccaac cccaacaata ataaataaaa    1860
ccaatctaac tactacacaa actaactaac taactaacta ctaaaaacta ctccacgctt    1920
ttaccgaaaa acaaaaacta acataaaaca aaaaaaaaac ctaactatcc tcatccta     1978
```

<210> SEQ ID NO 76
<211> LENGTH: 22
<212> TYPE: DNA
<213> ORGANISM: Homo sapiens

<400> SEQUENCE: 76
cctaaacact accacatctc aa                                              22

<210> SEQ ID NO 77
<211> LENGTH: 24
<212> TYPE: DNA
<213> ORGANISM: Homo sapiens

<400> SEQUENCE: 77
agaaatttag ttgttatggt ttgt                                            24

<210> SEQ ID NO 78
<211> LENGTH: 27
<212> TYPE: DNA
<213> ORGANISM: Homo sapiens
<220> FEATURE:
<221> NAME/KEY: misc_feature
<222> LOCATION: (1)..(1)
<223> OTHER INFORMATION: conjugaged to FAM
<220> FEATURE:
<221> NAME/KEY: misc_feature
<222> LOCATION: (27)..(27)
<223> OTHER INFORMATION: conjugated to BHQ1

<400> SEQUENCE: 78
aaaaaaccat caaccccata acacaaa                                         27

<210> SEQ ID NO 79
<211> LENGTH: 21
<212> TYPE: DNA
<213> ORGANISM: Homo sapiens

<400> SEQUENCE: 79
ctaaacacta ccacatctcg a                                               21

<210> SEQ ID NO 80
<211> LENGTH: 22
<212> TYPE: DNA
<213> ORGANISM: Homo sapiens

<400> SEQUENCE: 80
aaatttagtt gttacggttt gc                                              22

<210> SEQ ID NO 81

```
<211> LENGTH: 18
<212> TYPE: DNA
<213> ORGANISM: Homo sapiens
<220> FEATURE:
<221> NAME/KEY: misc_feature
<222> LOCATION: (1)..(1)
<223> OTHER INFORMATION: conjugated to HEX
<220> FEATURE:
<221> NAME/KEY: misc_feature
<222> LOCATION: (18)..(18)
<223> OTHER INFORMATION: conjugated to BHQ1

<400> SEQUENCE: 81
ccgtcgaccc cataacgc                                                 18

<210> SEQ ID NO 82
<211> LENGTH: 78
<212> TYPE: DNA
<213> ORGANISM: Homo sapiens

<400> SEQUENCE: 82
cctaaacact gccacatctc gaagccccctt gagagaagcc gtcggcccca tagcgcaagc    60
cgtagcagct agatttct                                                  78
```

EPIGENETIC MARKERS FOR THE IDENTIFICATION OF BLOOD SUB-CELLS OF TYPE 1

CROSS REFERENCE TO A RELATED APPLICATION

This application is a continuation of application Ser. No. 15/477,768, filed Apr. 3, 2017, which is a continuation-in-part of application Ser. No. 13/139,808, filed Oct. 18, 2011, which is a National Stage Application of International Application Number PCT/EP2009/008764, filed Dec. 8, 2009, which claims priority to European Application No. 08021838.1, filed Dec. 16, 2008, all of which are incorporated herein by reference in their entirety.

SEQUENCE LISTING

The instant application contains a Sequence Listing, which has been submitted electronically in ASCII format and is hereby incorporated by reference in its entirety. The Sequence Listing is labeled "113828.000015_SeqListing_April2019.txt," was created on Apr. 8, 2019, and is 54 KB.

BACKGROUND OF THE INVENTION

T-lymphocytes are a major component of the mammalian immune system. Both CD4 and CD8 T-cells are responsible for proper functioning of said immune system. Whereas CD8 T-cells mediate the cytotoxic immune defence, CD4 cells—the so called helper T-cells—assist both the humoral and the cell mediated immune defence. The heterodimeric T-cell antigen receptor (TCR) is bound to a monomorphic protein complex called CD3. CD3 consists of sub-elements CD3 γ, -δ, and -ε, and is expressed on all peripheral T-cells, but only on a subset of the thymocytes. The genes for CD3γ, -δ, and -ε are encoded on neighbouring loci on chromosom 11 (11q23).

Role of CD3 in signal transduction—The function of the CD3-chains is both the formation and the transport of the full CD3 complex to the cell surface, as well as the signal transduction upon stimulation through the heterodimeric T-cell antigen receptor. The amino acid sequence of the cytoplasmatic part of CD3γ, -δ, -ε each contains a motif that becomes phosphorylated upon stimulation, and thus activated. This so called ITAM (immunoreceptor tyrosine-based activated motif) serves as docking point for different tyrosine kinases. Individuals with defective CD3γ or-ε-chains suffer from a severe clinical autoimmune deficiency.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types.

The primary target of methylation is the two-nucleotide sequence Cytosine-Guanine (a 'CpG site'); within this context cytosine (C) can undergo a simple chemical modification to become 5-methyl-cytosine. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumour suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumour specific (i.e., changes in the methylation pattern of particular genes or even individual CpGs are diagnostic of particular tumour types), and there is now an extensive collection of diagnostic markers for bladder, breast, colon, oesophagus, stomach, liver, lung, and prostate cancers (summarized, for example, by Laird, Nature Reviews/Cancer 3:253-266, 2003).

Flanagan et al. (in Flanagan B F, Wotton D, Tuck-Wah S, Owen M J. DNase hypersensitivity and methylation of the human CD3G and D genes during T-cell development. Immunogenetics. 1990; 31(1):13-20.) describe that the mouse and human CD3G and D genes are organized in opposite transcriptional orientation, their 5' ends being separated by about 1.6 kilobases (kb) of DNA. The molecular basis of the tissue-specific regulation of expression of the human CD3G and D genes were examined using DNase I hypersensitivity and CpG methylation analysis in the mouse. The authors try to define areas 3' to the D gene and within the intergenic region which contain regulatory elements that influence both CD3D and G expression and show that transcription from the CD3D and G genes may occur initially from a methylated promoter. Significantly, the 3' regulatory region was shown to adopt an open chromatin structure prior to lineage commitment and before CD3 transcription. The quite limited enzymatic analysis of Flanagan is based on a region in the mouse that has no homology to any region as found in the human. Furthermore, the paper does not identify the regions as analyzed as suitable for the identification of DC3 lymphocytes.

Clevers et al. (in Clevers H, Lonberg N, Dunlap S, Lacy E, Terhorst C. An enhancer located in a CpG-island 3' to the TCR/CD3-epsilon gene confers T lymphocyte-specificity to its promoter. EMBO J. 1989 Sep.;8(9):2527-35.) describe that the gene encoding the CD3-epsilon chain of the T cell receptor (TCR/CD3) complex is uniquely transcribed in all T lymphocyte lineage cells. The human CD3-epsilon gene, when introduced into the mouse germ line, was expressed in correct tissue-specific fashion. The gene was then screened for T lymphocyte-specific cis-acting elements in transient chloramphenicol transferase assays. The promoter (−228 to +100) functioned irrespective of cell type. A 1225 bp enhancer with strict T cell-specificity was found in a DNase I hypersensitive site downstream of the last exon, 12 kb from the promoter. This site was present in T cells only. The CD3-epsilon enhancer did not display sequence similarity with the T cell-specific enhancer of CD3-delta, a related gene co-regulated with CD3-epsilon during intrathymic differentiation. The CD3-epsilon enhancer was unusual in that it constituted a CpG island, and was hypomethylated independent of tissue type. Two HTLV I-transformed T cell lines were identified in which the CD3-epsilon gene was not expressed, and in which the enhancer was inactive. In contrast to the preferred embodiment of the present invention, Clevers et al. analyze a remotely located enhancer region of 3' to the TCR/CD3-epsilon gene.

Hamerman et al. (in: Hamerman J A, Page S T, Pullen A M. Distinct methylation states of the CD8 beta gene in peripheral T cells and intraepithelial lymphocytes. J Immunol. 1997 Aug. 1; 159(3):1240-6) distinguish between CD4 and CD8 T-lymphocytes.

EP 1 213 360 describes a method of identifying a cell, tissue or nucleus, comprising collecting information on the methylation pattern of DNA isolated from the cell, tissue or nucleus and analyzing the resultant information.

WO 2004/050706 describes a sub-group of T-cells, and relates to characteristics of regulatory T-cells which define them as such. The application also describes the uses of such T-cells, compositions comprising them, and chemokines which recruit them in the modulation of an immune response.

Finally, EP 1 826 279 describes a method, in particular an in vitro method, for identifying FoxP3-positive regulatory T cells, preferably CD25+ CD4+ regulatory T cells of a mammal, comprising analyzing the methylation status of at least one CpG position in the gene foxp3 or an orthologous or paralogous gene thereof, and the use of DNA-methylation analysis of the gene of the transcription factor FoxP3 for a detection and quality assurance and control of regulatory T cells.

While the measurement and determination of CD4 and CD8 cells is generally easy and is usually achieved through analyzing the expression of said antigens on the cellular surface, clinically, it remains challenging to determine these cell types, since for the commonly used FACS analysis the cell samples need to be freshly isolated or immediately fixated in order to keep the cell entities intact. Thus, the detection of T lymphocytes, while desirous, is problematic, particularly for routine applications.

In view of the above, it is an object of the present invention to provide an improved and in particular robust method based on DNA methylation analysis as a superior tool in order to more conveniently and reliably identify T-lymphocytes.

BRIEF SUMMARY

The present invention relates to a method, in particular an in vitro method, for identifying CD3CD4 and/or CD3CD8 positive T lymphocytes of a mammal, wherein said method comprises analysing the methylation status of at least one CpG position in the CD3δ/γ/ε genes, in particular their "upstream" regulatory regions, and in particular the promoter and other conserved regions of the gene for CD3, wherein a demethylation of at least one CpG in the analyzed sample to at least 90% is indicative for memory and naive CD4+ T lymphocytes and memory and naive CD8+ T lymphocytes. The present invention is further related at analyzing the methylation status of at least one CpG position in the genes SLA2, CHRNA3, C16orf24, LCK, FASLG, CD7, SIT1, IL32, CXCR6, UBASH3A, GRAP2, ITGB7 and TXK which also allows the unambiguously identification of all CD3 positive T lymphocytes. For further unambiguous identification of all CD8 cells, also the equivalent analysis GNGT2, CRTAM, IL2RB and ZBTB32 can be employed. Among the CD3 positive T lymphocytes, these markers are capable to segregate between CD8 and CD4 positive cells. Equivalently, FLJ00060, FLJ38379, PPP6C, CD226, ZBTB7B and TNFAIP8 are capable of positively identifying CD4 expressing cells in whole blood and segregate between CD4 and CD8 positive CD3 positive cells.

Furthermore, the present invention is directed at the use of DNA-methylation analysis of the genes CD3γ/δ/ε or SLA2, CHRNA3, C16orf24, LCK, FASLG, CD7, SIT1, IL32, CXCR6, UBASH3A, GRAP2, ITGB7 and TXK or GNGT2, CRTAM, IL2RB and ZBTB32. or FLJ00060, FLJ38379, PPP6C, CD226, ZBTB7B and TNFAIP8 for the detection and quality assurance and control of T lymphocytes. Furthermore, the present invention relates to a kit for performing the above methods as well as respective uses thereof. In a preferred embodiment, the present invention furthermore provides an improved method for analysing the methylation status of at least one CpG position in the gene CD3, allowing for a precise analysis even from sub-optimal quality samples, such as non-freshly obtained blood or serum samples. It is one aim of this invention to provide a novel, more robust means to quantitatively detect and measure particular subsets of the blood within any solid organs or any body fluid of a mammal.

Employing this method, the inventors provide for novel, not previously known means of determining, quantitating and routinely measuring T lymphocytes.

BRIEF DESCRIPTION OF THE FIGURES

FIGS. 2A-2B show the analysis of amplicon No. 1405 (SEQ ID NO: 6), bisulfite strand 2, sequencing direction: forward. Relevant positions are indicated in bold. FIGS. 2A-2B show SEQ ID NOs: 6, 39, 40, 42, 43, 44, and 45, as identified in FIG. 2B.

FIGS. 3A-3B show the analysis of amplicon No. 1406, bisulfite strand 2, sequencing direction: reverse. Relevant positions are indicated in bold. FIGS. 3A-3B show SEQ ID NOs: 46, 47, 48, 49, 50, 51, 66, and 67, as identified in FIG. 3B.

FIGS. 4A-4B show the analysis of amplicon No. 1406 (SEQ ID NO: 7), bisulfite strand: 2, sequencing direction: forward. Relevant positions are indicated in bold. FIGS. 4A-4B show SEQ ID NOs: 7, 52, 53, 54, 55, 56, 57, and 58, as identified in FIG. 4B.

FIGS. 5A-5B show the analysis of amplicon No. 1408 (SEQ ID NO: 8), bisulfite strand: 2, sequencing direction: forward. Relevant positions are indicated in bold. FIGS. 5A-5B show SEQ ID NOs: 8, 59, 60, 61, 62, 63, 64, and 65, as identified in FIG. 5B.

FIGS. 6A-6E show the regulatory regions of the γ,δ-T-cell receptor, including regions Nr. 1405 1406 und 1408 on chromosome 11 (NCBI36:11:117714000:117730500:1). Exon sequences are underlined for CD3 δ, and double underlined for CD3 γ. CGs are in bold.

FIG. 7 shows an example of bisulfite-treated nucleotide sequence having non-methylated CpG motifs.

FIG. 8 shows an example of a bisulfite-treated nucleotide sequence having methylated CpG motifs.

BRIEF DESCRIPTION OF THE SEQUENCES

Figure 1:
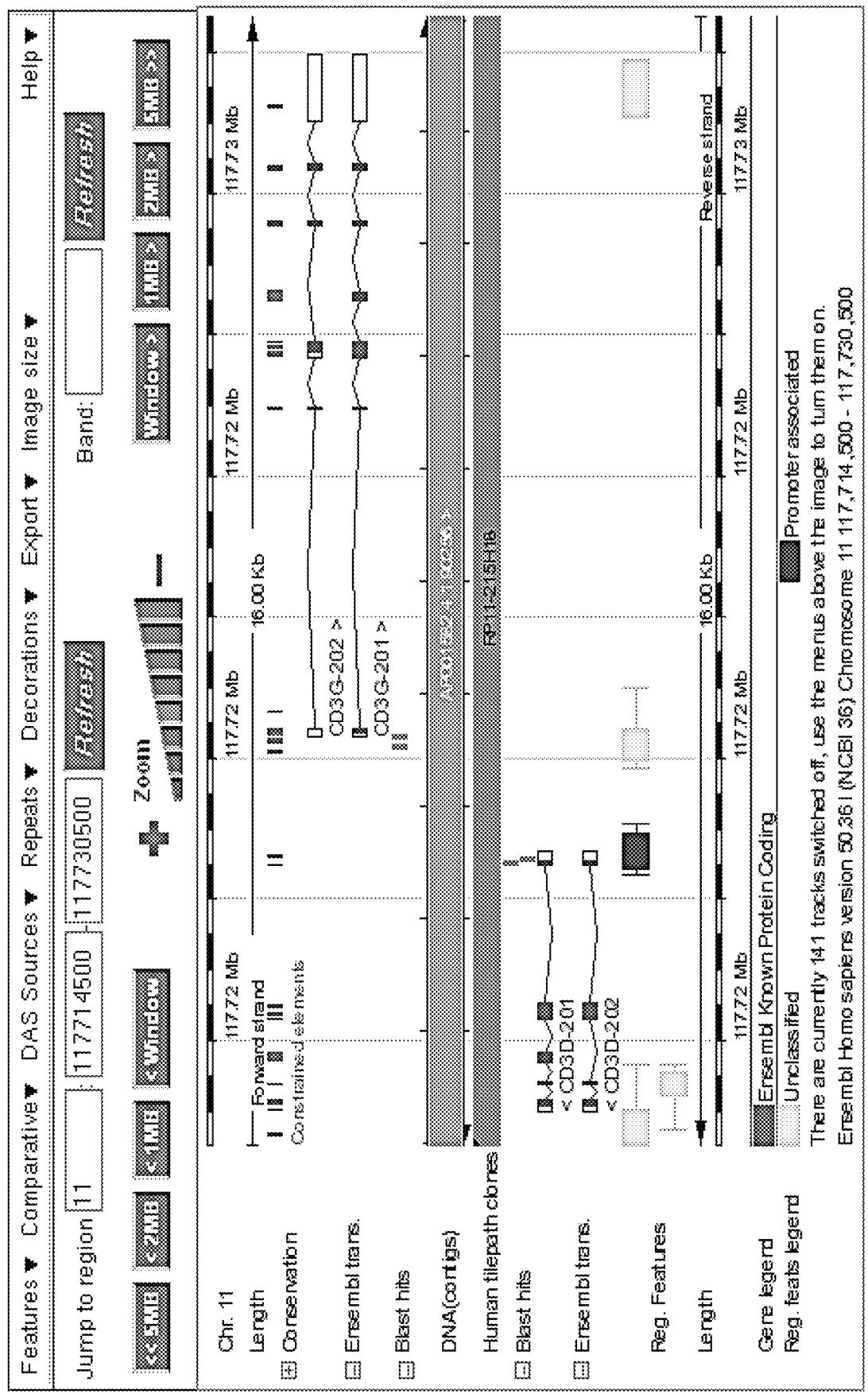
FIG. 1 shows the differentially methylated gene region as found for CD3 g and d and are indicated by thick lines as "blast hits".

SEQ ID NO: 1 shows the sequence of the region as considered to have a specific methylation pattern in CD3 cells.

SEQ ID NOs: 2 to 5 and 9 show the sequences of oligonucleotides used in the Illumina Chip-Fragment assay for CD3γ and CD3δ and CD3ε.

SEQ ID NOs: 6 to 8 show the reference sequences of amplicon No. 1405 (SEQ ID NO: 6), amplicon No. 1406 (SEQ ID NO: 7), and amplicon No. 1408 (SEQ ID NO: 8).

SEQ ID NOs: 10 to 38 show the sequences around the CpG positions as analyzed in other preferred T-lymphocyte markers of the present invention according to example 2.

SEQ ID NOs: 39 to 65 show the sequences as depicted in the alignments of FIGS. 2A to 5B. If not stated otherwise, the sequences are ordered in the succession of their appearance in FIGS. 2A to 5B.

SEQ ID NOs: 68 and 69 show the sequences of the reverse complement sequences of SEQ ID NO: 5 and SEQ ID NO: 2, which reverse complementary sequences are used to amplify an amplicon from nucleic acid molecules comprising SEQ ID NO: 1.

SEQ ID NOs: 70 and 71 show the sequences of a primer pair used to amplify one strand of a bisulfite-treated nucleic acid molecule comprising SEQ ID NO: 1

SEQ ID NOs: 72 and 73 show the sequences of a primer pair used to amplify the complementary strand of the bisulfite-treated nucleic acid molecule comprising SEQ ID NO: 1.

SEQ ID NO: 74 shows the sequence of a portion of the bisulfite-treated nucleic acid sequence of SEQ ID NO: 1 in which the CpG motifs are non-methylated, the shown sequence comprising the preferred sequences of SEQ ID NOs: 72, 73, 76, 77, and 78.

SEQ ID NO: 75 shows the sequence of a portion of the bisulfite-treated nucleic acid sequence of SEQ ID NO: 1 in which the CpG motifs are methylated, the shown sequence comprising the preferred sequences of SEQ ID NOs: 79-81.

SEQ ID NO: 76 shows the forward primer used for amplification of a portion of the bisulfite-treated SEQ ID NO: 1 having non-methylated CpGs.

SEQ ID NO: 77 shows the reverse primer used for amplification of a portion of the bisulfite-treated SEQ ID NO: 1 having non-methylated CpGs.

SEQ ID NO: 78 shows the sequence of a probe used for quantitative PCR amplification of a portion of the bisulfite-treated SEQ ID NO:1 with primers of SEQ ID NOs: 76 and 77.

SEQ ID NO: 79 shows the forward primer used for amplification of a portion of the bisulfite-treated SEQ ID NO: 1 having methylated CpGs.

SEQ ID NO: 80 shows the reverse primer used for amplification of a portion of the bisulfite-treated SEQ ID NO: 1 having methylated CpGs.

SEQ ID NO: 81 shows the sequence of a probe used for quantitative PCR amplification of a portion of the bisulfite-treated SEQ ID NO: 1 with primers of SEQ ID NOs: 79 and 80.

SEQ ID NO: 82 shows the sequence of a region within the sequence of SEQ ID NO: 1. In the $CD3^+$ T-lymphocytes, this seqeunce has a specific methylation pattern on certain cytosines. As indicated in FIG. 6B, such cytosines are located on positions 20, 40, 43, 54, and 61 of SEQ ID NO: 82.

DETAILED DESCRIPTION

The present invention solves the above object by providing a method for identifying T-lymphocytes in a mammal, in particular in a sample derived from a mammal, comprising analysing the methylation status of at least one CpG position in one or more of the genes for CD3 γ, -δ, and -ε, wherein a demethylation of at least one CpG position to at least 90% in said sample is indicative for a $CD3^+$ T-lymphocyte cell, in particular a $CD3^+$ $CD4^+$, and/or $CD3^+$ $CD8^+$ T-lymphocyte cell.

The present invention is based on the surprising finding of the inventors that the identification of CD3 gene as a specific epigenetic marker can greatly facilitate the clinical routine application of the analysis of the above markers. In contrast to FACS and mRNA measurements, the respective measurement(s) can be done independent of purification, storage and to quite some extend also to tissue quality.

In another preferred embodiment of the method according to the present invention, said at least one CpG position in said sample is demethylated to more than 91% and preferably more than 92% and most preferred more than 95%.

This concept is based on specific demethylation of the CD3 regions in CD3 positive T-lymphocytes. Using a simple and precise quantitative PCR method, the inventors show that CD3 demethylation represents a surrogate marker for T-lymphocyte counts in blood or tissues. The present inventors have thus identified particular regions within the CD3 gene, which are functionally involved in, or mandatory associated with, the existence of CD3 positive T-lymphocytes. In one preferred embodiment one very good region is either the promoter or the TLSDR with e.g. the nucleotide sequence according to SEQ ID NO: 1 and others, containing many CpG motifs, which display a differential methylation status when cells expressing CD3 in either $CD4^+$ or $CD8^+$ cells compared with all other cells, not expressing CD3 if, for example, the bisulphite sequencing method is used. An example of bisulfite-treated nucleotide sequence according to SEQ ID NO: 1 having non-methylated CpG motifs is provided in SEQ ID NO: 74 and FIG. 7. A further example of the similar bisulfite-treated nucleotide sequence according to SEQ ID NO: 1 having methylated CpG motifs is provided in SEQ ID NO: 75 and FIG. 8.

The inventors could demonstrate that in $CD3^+$ cells the CpG motifs are almost completely demethylated (i.e. to more than 70%, preferably 80%, preferably, more than 90% and most preferred more than 95%), whereas the same motifs are completely methylated in all $CD3^-$ cells. The differential methylation of the CpG motifs within the aforementioned region correlates with CD3 expression. Thus, determination of the methylation status of the CD3 locus could become a valuable tool to identify T-lymphocytes, such as will be required/or at least of some value for measuring T-lymphocytes in autoimmune diseases, transplant rejections, cancer, allergy, or just the T-lymphocytes related immune status in any envisionable context, when desired. The assays allows measurement of T-lymphocytes without purification or any staining procedures. It even reports in solid tumors or other solid tissues the number of cells demethylated in said region, thus showing the total amount of CD3 positive tumor infiltrating T-lymphocytes.

The inventors have shown that the potential for constitutive expression of CD3 in T-lymphocytes coincides with epigenetic, i.e., DNA methylation based regulation. DNA methylation is a biologically and chemically stable epigenetic modification, resulting in long-term gene expression changes. The inventors found demethylation at the human CD3 locus to be restricted to T-lymphocytes when tested against all major peripheral blood cell types and a selection of non-blood cells. These data indicated that epigenetic modifications in the CD3 locus serve as valuable marker for the identification of cells with the phenotype of T-lymphocyte, regardless of the expression of the specific delta or gamma sub-chains. In another preferred aspect of the method according to the present invention the methylation status of at least one CpG position in the genes SLA2, CHRNA3, C16orf24, LCK, FASLG, CD7, SIT1, IL32, CXCR6, UBASH3A, GRAP2, ITGB7 and TXK is analysed in analogy to what is described herein for CD3. These genes thus also allow the unambiguous identification of all CD3 positive T lymphocytes. Thus, in a preferred embodiment of the method according to the present invention, said at least one CpG position is present in the 5' region upstream from the transcription start, promoter region, intron, and/or exon/intron border within the gene(s) SLA2, CHRNA3, C16orf24, LCK, FASLG, CD7, SIT1, IL32, CXCR6, UBASH3A, GRAP2, ITGB7 and TXK.

In order to further unambiguously identify all CD8 cells, the present invention in another preferred aspect thereof provides the equivalent analysis of the genes GNGT2, CRTAM, IL2RB and ZBTB32 among the CD3 positive T lymphocytes, as these markers are capable to segregate between CD8 and CD4 positive cells. This analysis is preferably performed simultaneously or subsequently to the analysis for the CD3 phenotype of the T-lymphocytes.

Equivalently, FLJ00060, FLJ38379, PPP6C, CD226, ZBTB7B and TNFAIP8 are capable of positively identifying CD4 expressing cells in whole blood and segregate between CD4 and CD8 positive cells.

Another preferred aspect of the method according to the present invention is directed at the use of DNA-methylation analysis of the genes CD3γ/δ/ε, or SLA2, CHRNA3, C16orf24, LCK, FASLG, CD7, SIT1, IL32, CXCR6, UBASH3A, GRAP2, ITGB7 and TXK or GNGT2, CRTAM, IL2RB and ZBTB32 or FLJ00060, FLJ38379, PPP6C, CD226, ZBTB7B and TNFAIP8 for the detection and quality assurance and control of T lymphocytes.

In another preferred embodiment of the method according to the present invention, said at least one CpG position is present in the 5' region upstream from the transcription start, promoter region, intron, and/or exon/intron border within the CD3 gene. The present invention also provides the surprising finding that in particularly preferred regions of the gene for CD3, the so-called "TLSDRs" (T lymphocyte specific demethylated regions), the CpG motifs are almost completely demethylated (i.e. to more than 90%, preferably 91%, preferably, more than 92% and most preferred more than 95%), whereas the same motifs are completely methylated in all non T lymphocytes. Thus, this region and the diagnostic uses thereof also provide a valuable and reliable tool for a diagnostic analysis according to the present invention. The TLSDR according to the present invention are located in amplicon No. 1405 (SEQ ID NO: 6), amplicon No. 1406 (SEQ ID NO: 7), and/or amplicon No. 1408 (SEQ ID NO: 8). All of these amplicons are parts of the overall region of interest of the present invention as depicted in SEQ ID No. 1. Upon bisulfite treatment of SEQ ID NO:1, a preferred region of the present invention is shown in FIGS. 7 and 8 and is disclosed as sequences of SEQ ID NOs: 74 and 75.

In a preferred embodiment of the method according to the present invention, said analysis of the methylation status comprises amplification with at least one primer of suitable primer pairs that can be suitably designed based on SEQ ID NO: 1, preferably oligomers according to any of SEQ ID NOs: 2 to 5. The person with ordinary skill in the art will readily appreciate that, for example, in order to amplify a sequence of SEQ ID NO: 1 located between oligomers of SEQ ID NO: 5 and SEQ ID NO: 2, primers are designed such that the primers comprise the reverse complement sequences of SEQ ID NOs: 5 and 2. Such reverse complement primers of SEQ ID NOs: 5 and 2 are primer sequences of SEQ ID NO: 68 and 69, respectively. Therefore, in a preferred embodiment primers to amplify an amplicon from SEQ ID NO: 1 are SEQ ID NOs: 68 and 69. SEQ ID NO: 68 is the reverse complement of SEQ ID NO: 5 and SEQ ID NO: 69 is the reverse complement of SEQ ID NO: 2.

In one embodiment of the method according to the present invention, said at least one CpG position is present in the region comprising SEQ ID NOs: 2-5.

In a preferred embodiment, the method comprises bisulfite treating the genomic DNA isolated from a cell and amplifying the region comprising SEQ ID NO: 1 using a primer pair designed to amplify bisulfite-treated SEQ ID NO: 1. The primer pair can be designed based on the bisulfite-treated SEQ ID NO: 1. Methods to design primers to amplify bisulfite-treated genomic DNA are within the knowledge of the art.

For example, a primer pair to amplify one strand of the bisulfite-treated genomic DNA comprising SEQ ID NO: 1 comprises:
  i) a forward primer of SEQ ID NO: 70, and
  ii) a reverse primer of SEQ ID NO: 71.

A primer pair to amplify the complementary strand of the bisulfite-treated genomic DNA comprising SEQ ID NO: 1 comprises:
  (i) a forward primer of SEQ ID NO: 72, and
  (ii) a reverse primer of SEQ ID NO: 73.

A preferred embodiment is a bisulfite-treated sequence of SEQ ID NO: 1. A further preferred embodiment is a partial sequence of bisulfite-treated sequence of SEQ ID NO: 1, which partial sequence comprises non-methylated CpG motifs and is SEQ ID NO: 74. A further embodiment is a partial sequence of bisulfite-treated sequence of SEQ ID NO: 1, which partial sequence comprises methylated CpG motifs and is SEQ ID NO: 75.

Preferably, the amplification involves a polymerase enzyme, a PCR or chemical amplification reaction or other amplification methods as known to the person of skill as described below, e.g. in the context of MSP, HeavyMethyl, Scorpion, MS-SNUPE, MethylLight, bisulfite sequencing, methyl specific restriction assays. With the amplification, the amplicon of the TLSDR or any other region in the CD3 gene or any paralog or ortholog as described herein is produced that is a particularly preferred "tool" for performing the method(s) according to the present invention. Consequently, an oligomer according to any of SEQ ID NOs: 2 to 5 or the amplicon as amplified by a primer pair as mentioned above constitute preferred embodiments of the present invention.

The person of skill will furthermore be able to select specific subsets of CpG positions in order to minimise the amount of sites to be analyzed, for example at least one of CpG position 1, 2, 3, 4, 5, 6, 7, 8, 9, and 10 of the amplicon No. 1405 (SEQ ID NO: 6), amplicon No. 1406 (SEQ ID NO: 7), and amplicon No. 1408 (SEQ ID NO: 8), or all sites as present on the amplicons or according to SEQ ID NO: 1 or other sequences in the CD3 locus. The positions are numerically counted from the 5'-end of the amplicon as generated and analysed. Preferred are combinations of 4, 5, 6, or 7 positions, which are producing enough information in order to be informative in the context of the present invention.

In order to analyze the methylation status of CpG positions, any known method to analyse DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethylLight, Ms-SNuPE or other methods relying on a detection of amplified DNA. These methods are well known to the person of skill, and can be found in the respective literature. For example, primers and a probe to be used according to the instant invention for the detection of non-methylated CpG motifs in the preferred partial nucleotide sequence of bisulfite-treated SEQ ID NO:1, i.e. SEQ ID NO:74, are SEQ ID NOs: 76-78. Primers and a probe to be used according to the instant invention for the detection of methylated CpG motifs in the preferred partial nucleotide sequence of bisulfite-treated SEQ ID NO:1, i.e. SEQ ID NO:75, are SEQ ID NOs: 79-81.

In a preferred embodiment of the method according to the present invention, said method is suitable for routine application, for example on a DNA-chip. Based on the above information and the respective literature, the person of skill will be able to adjust the method as above to such settings.

In another preferred embodiment of the method according to the present invention, the identification comprises a distinction of said T-lymphocytes from all major peripheral blood cell types or non-blood cells, preferably, but not limited to, CD14, CD15, CD19, and CD56.

In yet another preferred embodiment of the method according to the present invention, the sample is selected from a mammalian body fluid, including human blood samples, or a tissue, organ or cell type blood sample, a sample of blood lymphocytes or a fraction thereof. Preferably, said mammal is a mouse, rat, monkey or human. The samples can be suitably pooled, if required.

Another preferred aspect of the method according to the present invention then further comprises the step of concluding on the immune status of said mammal based on said T-lymphocytes as identified. The general lymphocyte population can be quantified and either be used as a benchmark to relatively quantify further detailed subpopulations such as the CD3CD4CD25 positive regulatory T cells or it can be used to finally detect this population to determine the overall immune activity status.

In yet another preferred embodiment of the methods according to the present invention, the mammal suffers from or is likely to suffer from autoimmune diseases, transplant rejections, cancer, and/or allergy.

Another preferred aspect of the method according to the present invention is related to a method for monitoring the level of CD3$^+$ CD4$^+$, and/or CD3$^+$ CD8$^+$ T-lymphocytes in a mammal, comprising a method as above, and comparing the amount of T-lymphocytes as identified to an earlier sample taken from the same mammal, and/or to a control sample. In yet another preferred embodiment of the methods according to the present invention, the mammal suffers from or is likely to suffer from autoimmune diseases, transplant rejections, cancer, and/or allergy.

Another preferred aspect of the method according to the present invention then relates to a method as above, further comprising measuring and/or monitoring the amount of said T-lymphocytes in response to chemical and/or biological substances that are provided to said mammal.

Another preferred aspect of the method according to the present invention relates to an oligomer according to any of SEQ ID NOs: 2 to 5, SEQ ID NOs: 68 to 73, SEQ ID NOs: 76, 77, 79 and 80, or an amplicon as amplified by a primer pair based on SEQ ID NO: 1 and designed as described above, in particular the amplicon No. 1405 (SEQ ID NO: 6), amplicon No. 1406 (SEQ ID NO: 7), and amplicon No. 1408 (SEQ ID NO: 8). A particularly preferred primer pair are SEQ ID NOs: 70 and 71 to amplify one strand of a preferred partial sequence of SEQ ID NO:1. Another particularly preferred primer pair are SEQ ID NOs:72 and 73 to amplify the complementary strand of the preferred partial sequence of SEQ ID NO: 1. A further preferred primer pair are SEQ ID NOs: 79 and 80 to be used with a probe of SEQ ID NO: 81 for quantitative PCR of a preferred partial sequence of bisulfite-treated SEQ ID NO: 1. An additional primer pair are SEQ ID NOs: 76 and 77 to be used with a probe of SEQ ID NO: 78 for quantitative PCR of a preferred partial sequence of bisulfite-treated SEQ ID NO: 1.

Yet another preferred aspect of the present invention then relates to a kit for identifying and/or monitoring CD3$^+$ CD4$^+$, and/or CD3$^+$ CD8$^+$ T-lymphocytes in a mammal based on the analysis of the methylation status of CpG positions in the gene CD3, comprising materials for performing a method according the present invention as described herein. Preferably, said kit comprises a) a bisulfite reagent, and b) materials for the methylation analysis of CpG positions as comprised by the amplicon No. 1405 (SEQ ID NO. 6), amplicon No. 1406 (SEQ ID NO: 7), and amplicon No. 1408 (SEQ ID NO: 8). Further preferred, the positions consist of positions 1, 2, 3, 4, 5, 6, 7, 8, 9, and 10 of said amplicons. Most preferred are 5, 6, or 7 or all positions on said amplicon.

Finally, the present invention also encompasses the use of an oligomer or amplicon or a kit according to the present invention for identifying and/or for monitoring CD3$^+$ CD4$^+$, and/or CD3$^+$ CD8$^+$ T-lymphocytes in a mammal.

In summary, using the CD3 marker, the inventors very specifically identified (but not differentiated) both CD3/CD4 positive as well as CD3/CD8 positive T lymphocytes. Using the marker CD8beta, for example CD8 positive lymphocytes could then be distinguished from CD4 lymphocytes. This, when using a combination of the present marker(s) and the CD8beta marker, CD4 and CD8 cells can be specifically distinguished. This was not possible before the invention, since all CD4 looked identical to non-T lymphocytes.

The invention will now be further described based on the following examples and with reference to the accompanying figures and the sequence protocol, without being limited thereto. For the purposes of the present invention, all references as cited herein are incorporated by reference in their entireties. In the Figures and Sequences,

EXAMPLES

Example 1—CD3-Analysis

The inventors have purified various blood subsets, including CD3/CD4, CD3/CD8 naive and memory T lymphocytes, CD56 natural killer cells, CD19 naive and memory B cells, CD14 monocytes and CD15 granulocytes. DNA from the purified cells was bisulfite-treated and analysed at various CpG dinucleotide motifs. The inventors then compared the methylation status (finding C as for Cytosine that was methylated in the original sequence versus T for cytosine that was unmethylated in the original sequence).

The data showed various CpG motifs and areas in the CD3 γ, δ and ε that were demethylated in all CD3CD4 and CD3CD8 cell types while methylated in all other blood cell types. The differentially methylated gene regions as found for CD3 γ, δ and ε are shown below in FIG. 1 and are indicated in bold as "blast hits."

The data, as observed with Illumina Golden Gate technology, show that all CD4 and CD8 positive memory (0.06 and 0.06 respectively) and naive (0.03 and 0.06, respectively) T cells are subject to much lower methylation rates than all other tested cell types, including CD15 (0.92), CD14 (0.90), CD19 memory and naive (0.81 and 0.67, respectively), CD56 (0.86) positive blood cells as well as cells derived (0.78) from non-blood tissues. The experimental results are further depicted in the following table.

TABLE 1

Methylation analysis results

| Gene | Chr. | S1 n = 12; female | S2 n = 5; male | S3 Pool; female | S4 Pool; (5 male) | S5 Pool; (5 male) | S6 Pool; (5 male) | S7 Pool; (5 male) | S8 Pool; (5 male) | S9 Pool; (5 male) | S10 Pool; (5 male) | S11 Pool; (5 male) | 512 Pool; (5 male) |
|---|---|---|---|---|---|---|---|---|---|---|---|---|---|
| CD3D | 11 | 0.8 | 0.6 | 0.6 | 0.9 | 0.9 | 0.9 | 0.0 | 0.1 | 0.1 | 0.1 | 0.7 | 0.8 |
|  |  | 0.9 | 0.7 | 0.7 | 0.9 | 0.9 | 0.9 | 0.1 | 0.1 | 0.2 | 0.2 | 0.7 | 0.8 |
| CD3G | 11 | 0.7 | 0.6 | 0.7 | 0.9 | 0.9 | 0.8 | 0.1 | 0.1 | 0.1 | 0.1 | 0.8 | 0.9 |
|  |  | 0.4 | 0.6 | 0.5 | 0.7 | 0.8 | 0.7 | 0.1 | 0.1 | 0.1 | 0.1 | 0.3 | 0.6 |

Si = ovarian tissue, S2 = whole blood, S3 peripheral blood mononuclear cells, S4 = granulocytes, S5 = monocytes, S6 = NK cells, S7 = naïve T helper cells, S8 = memory T helper cells, S9 = naïve cytotoxic T cells, S10 = memory cytotoxic T cells, S11 = naïve B-cells, S12 = memory B-cells., Chr = chromosome The data showing the high specificity were obtained using a Illumina Golden Gate technology, with the following genomic CpGs regions analysed CD3γ
cg15880738
(SEQ ID NO: 2)
(+1) AGCTGCTGCACAGGCTGGCTGGCTGGCTGCTAAGGGCTGCTC

CACG cg07545925
(SEQ ID NO: 3)
(+1) CGGAAAAACAAAAGGCATCTGCACCTGCAGCCCTGCTGAGGCCCCT

GCTG

CD3δ
cg24841244
(SEQ ID NO: 4)
(-1) ACCCAGGCTGATAGTTCGGTGACCTGGCTTTATCTACTGGATGAG

TTCCG cg07728874
(SEQ ID NO: 5)
(-1) TGGAACATAGCACGTTTCTCTCTGGCCTGGTACTGGCTACCCTTC

TCTCG

CD3ε
cg24612198
(SEQ ID NO: 9)
AGTCATCTGTTTTGCTTTTTTTCCAGAAGTAGTAAGTCTGCTGGCCTCCG

Since the Illumina technology does only allow the analysis of a single CpG (or rather 2 CpGs per gene locus) the inventors verified the methylation properties using bisulfite sequencing. For that, the inventors bisulfite treated the samples using the Qiagen EpiTect kit, and sequenced the samples using an ABI 3100 prism sequencer. For data interpretation, the KB base calling software supplied by ABI was used.

While not providing entirely quantitative results calculating the percentile of methylated (i.e., CG signal on the plus strand sequence) versus unmethylated (i.e., TG on the plus strand sequence), the data were unambiguous for the purified cell types. All T-lymphocytes were overwhelmingly demethylated at all CG positions analysed, whereas all other analysed cell types were methylated at identical positions.

Example 2—Analysis of Additional Markers in Analogy to CD3

In order to identify further suitable markers distinguishing and monitoring T-lymphocytes, other markers in addition to CD3 have been identified and tested through methylation analysis. It was found that methylation in the CpG positions in the genes for SLA2, CHRNA3, C16orf24, LCK, FASLG, CD7, SIT1, IL32, CXCR6, UBASH3A, GRAP2, ITGB7 and TXK can also be used in the context of the present invention, as these markers are also able to identify CD3 positive T lymphocytes.

Furthermore, other markers have been identified that identify the subset of the CD8 and CD4 positive cells in the group of CD3 positive T lymphocytes. The genes for GNGT2, CRTAM, IL2RB and ZBTB32 have been found to segregate between CD8 and CD4 positive cells. Equivalently, FLJ00060, FLJ38379, PPP6C, CD226, ZBTB7B and TNFAIP8 are capable of positively identifying CD4 expressing cells in whole blood and segregate between CD4 and CD8 positive CD3 positive cells.

The following Table 2 summarizes the Illumina-data as obtained for the above markers at selected CpG positions. It can be seen that several other markers can be used in order to selectively identify CD4+ (for CD3+ lymphocyte subset-identification), namely FLJ00060; FLJ38379; PPP6C; CD226; ZBTB7B and/or TNFAIP8, in order to selectively identify CD8+ (for CD3+ lymphocyte subset-identification), namely GNGT2; CRTAM; IL2RB and/or ZBTB32, and in order to selectively identify CD3+ lymphocytes, namely CD3D; CD3G, and/or CD3E, and/or SLA2,CHRNA3, C16orf24; LCK; FASLG; FASLG; CD7; SIT1; IL32; CXCR6; UBASH3A; GRAP2; ITGB7 and/or TXK, as shown with selected CpG sites as preferred examples. Based on the table, the person of skill will be able to extend the teaching regarding CD3 as herein to these markers and their CpG sites.

TABLE 2

Illumina-data as obtained selected markers at CpG positions Chr. = chromosome

| CpG-ID | Gene Name | Chr. No | SEQ ID No./ Accession No | Ovar Tissue (mean, n = 12) | Whole Blood (Pool) | PBMC (Promega) | BCST18 Granulocyte (CD15+) | BCST19 Monocyte (CD14+) | BCST20 NK (CD56+) | BCST21 T naive (CD4+ CD27+ CD45RA+) | BCST22 T mem (CD4+ CD27+ CD45RA−) | BCST23 CTL naive (CD8+ CD27+ CD45RA−) | BCST24 CTL mem (CD8+ CD27+ CD45RA−) | BCST25 B naive (CD19+) | BCST26 B mem (CD19+) | Mean Value Target Cell Type | Mean Value Rest | Delta Meth (Target-Rest) |
|---|---|---|---|---|---|---|---|---|---|---|---|---|---|---|---|---|---|---|
| CD4+ marker | | | | | | | | | | | | | | | | | | |
| cg03602500 | FLJ00060 | 19 | 10/ NM_033206.1 | 0.802 | 0.728 | 0.779 | 0.858 | 0.851 | 0.873 | 0.235 | 0.279 | 0.521 | 0.687 | 0.656 | 0.747 | 0.257 | 0.75 | −0.493 |
| cg16173109 | FLJ38379 | 2 | 11/ XR_001026.1 | 0.614 | 0.675 | 0.719 | 0.833 | 0.844 | 0.784 | 0.1141 | 0.113 | 0.341 | 0.383 | 0.418 | 0.385 | 0.113 | 0.599 | −0.486 |
| cg00620024 | PPP6C | 9 | 12/ NM_002721.3 | 0.641 | 0.619 | 0.692 | 0.801 | 0.851 | 0.836 | 0.107 | 0.169 | 0.269 | 0.420 | 0.404 | 0.502 | 0.138 | 0.603 | −0.465 |
| cg13164537 | CD226 | 18 | 13/ NM_006566.1 | 0.458 | 0.470 | 0.508 | 0.582 | 0.557 | 0.601 | 0.029 | 0.071 | 0.351 | 0.543 | 0.366 | 0.501 | 0.05 | 0.494 | −0.443 |
| cg01782486 | ZBTB7B | 1 | 14/ NM_015872.1 | 0.789 | 0.725 | 0.720 | 0.823 | 0.809 | 0.886 | 0.190 | 0.428 | 0.875 | 0.864 | 0.586 | 0.414 | 0.309 | 0.749 | −0.44 |
| cg07086380 | TNFAIP8 | 5 | 15/ NM_014350.1 | 0.728 | 0.579 | 0.635 | 0.857 | 0.733 | 0.793 | 0.110 | 0.106 | 0.288 | 0.148 | 0.309 | 0.208 | 0.108 | 0.528 | −0.419 |
| CD8+ marker | | | | | | | | | | | | | | | | | | |
| cg17839611 | GNGT2 | 17 | 16/ NM_031498.1 | 0.779 | 0.629 | 0.688 | 0.828 | 0.867 | 0.207 | 0.340 | 0.562 | 0.09 | 0.119 | 0.854 | 0.722 | 0.104 | 0.648 | −0.543 |
| cg22512531 | CRTAM | 11 | 17/ NM_019604.2 | 0.651 | 0.634 | 0.709 | 0.835 | 0.735 | 0.5 | 0.363 | 0.630 | 0.079 | 0.082 | 0.194 | 0.336 | 0.08 | 0.559 | −0.478 |
| cg26757673 | IL2RB | 22 | 18/ NM_000878.2 | 0.799 | 0.662 | 0.752 | 0.878 | 0.9 | 0.092 | 0.573 | 0.086 | 0.157 | 0.061 | 0.411 | 0.403 | 0.109 | 0.555 | −0.446 |
| cg08539991 | ZBTB32 | 19 | 19/ NM_014383.1 | 0.823 | 0.736 | 0.791 | 0.912 | 0.926 | 0.674 | 0.563 | 0.153 | 0.303 | 0.085 | 0.648 | 0.140 | 0.194 | 0.637 | −0.442 |

TABLE 2-continued

Illumina-data as obtained selected markers at CpG positions Chr. = chromosome

| CD4+/CD8+ marker | Gene Name | Chr. | SEQ ID No./ Accession No | Ovar Tissue (mean, n = 12) | Whole Blood (Pool) | PBMC (Promega) | BCST18 Granulocyte (CD15+) | BCST19 Monocyte (CD14+) | BCST20 NK (CD56+) | BCST21 T naive (CD4+ CD27+ CD45RA+) | BCST22 T mem (CD4+ CD27+ CD45RA-) | BCST23 CTL naive (CD8+ CD27+ CD45RA-) | BCST24 CTL mem (CD8+ CD27+ CD45RA-) | BCST25 B naive (CD19+) | BCST26 B mem (CD19+) | Mean Value Target Cell Type | Mean Value Rest | Delta Meth (Target-Rest) |
|---|---|---|---|---|---|---|---|---|---|---|---|---|---|---|---|---|---|---|
| cg24841244 | CD3D | 11 | 20/ NM_000732.3 | 0.783 | 0.582 | 0.644 | 0.917 | 0.904 | 0.857 | 0.025 | 0.057 | 0.057 | 0.058 | 0.673 | 0.810 | 0.049 | 0.771 | -0.721 |
| cg07728874 | CD3D | 11 | 21/ NM_000732.3 | 0.854 | 0.683 | 0.727 | 0.911 | 0.901 | 0.881 | 0.128 | 0.149 | 0.175 | 0.155 | 0.744 | 0.807 | 0.152 | 0.814 | -0.661 |
| cg15880738 | CD3G | 11 | 22/ NM_000073.1 | 0.714 | 0.616 | 0.682 | 0.874 | 0.876 | 0.836 | 0.061 | 0.091 | 0.093 | 0.103 | 0.811 | 0.898 | 0.087 | 0.788 | -0.701 |
| cg07545925 | CD3G | 11 | 23/ NM_000073.1 | 0.370 | 0.552 | 0.545 | 0.737 | 0.771 | 0.739 | 0.133 | 0.149 | 0.132 | 0.131 | 0.303 | 0.601 | 0.132 | 0.49 | -0.358 |
| cg24612198 | CD3E | 11 | 24/ NM_000733.2 | 0.679 | 0.485 | 0.563 | 0.794 | 0.793 | 0.698 | 0.064 | 0.036 | 0.093 | 0.051 | 0.206 | 0.279 | 0.061 | 0.562 | -0.501 |
| cg04759756 | SLA2 | 20 | 25/ NM_032214.2 | 0.857 | 0.673 | 0.754 | 0.892 | 0.925 | 0.711 | 0.363 | 0.228 | 0.092 | 0.211 | 0.756 | 0.849 | 0.233 | 0.802 | -0.569 |
| cg22670733 | CHRNA3 | 15 | 26/ NM_000743.2 | 0.792 | 0.733 | 0.721 | 0.911 | 0.888 | 0.8 | 0.122 | 0.180 | 0.092 | 0.315 | 0.456 | 0.668 | 0.177 | 0.746 | -0.568 |
| cg09830866 | C16orf24 | 16 | 27/ NM_023931.1 | 0.493 | 0.629 | 0.647 | 0.842 | 0.79 | 0.076 | 0.041 | 0.056 | 0.033 | 0.058 | 0.72 | 0.510 | 0.047 | 0.588 | -0.541 |
| cg17078393 | LCK | 1 | 28/ NM_005356.2 | 0.807 | 0.575 | 0.666 | 0.920 | 0.884 | 0.26 | 0.05 | 0.037 | 0.036 | 0.041 | 0.144 | 0.27 | 0.041 | 0.566 | -0.524 |
| cg10161121 | FASLG | 1 | 29/ NM_000639.1 | 0.704 | 0.587 | 0.697 | 0.905 | 0.892 | 0.068 | 0.051 | 0.06 | 0.088 | 0.06 | 0.353 | 0.441 | 0.065 | 0.581 | -0.516 |
| cg00071250 | FASLG | 1 | 30/ NM_000639.1 | 0.659 | 0.498 | 0.602 | 0.871 | 0.838 | 0.075 | 0.061 | 0.069 | 0.139 | 0.051 | 0.391 | 0.41446208 | 0.08 | 0.543 | -0.463 |
| cg02473123 | CD7 | 17 | 31/ NM_006137.6 | 0.811 | 0.681 | 0.767 | 0.942 | 0.898 | 0.339 | 0.102 | 0.328 | 0.168 | 0.372 | 0.767 | 0.81 | 0.243 | 0.752 | -0.509 |
| cg15518883 | SIT1 | 9 | 32/ NM_014450.2 | 0.817 | 0.601 | 0.696 | 0.911 | 0.885 | 0.9033 | 0.11 | 0.142 | 0.154 | 0.358 | 0.392 | 0.373 | 0.191 | 0.697 | -0.506 |

TABLE 2-continued

Illumina-data as obtained selected markers at CpG positions Chr. = chromosome

| CpG-ID | Gene Name | Chr. | SEQ ID No./ Accession No | Ovar Tissue (mean, n = 12) | Whole Blood (Pool) | PBMC (Pro-mega) | BCST18 Granulo-cyte (CD15+) | BCST19 Mono-cyte (CD14+) | BCST20 NK (CD56+) | BCST21 T naive (CD4+ CD27+ CD45RA+) | BCST22 T mem (CD4+ CD27+ CD45RA−) | BCST23 CTL naive (CD8+ CD27+ CD45RA−) | BCST24 CTL mem (CD8+ CD27+ CD45RA−) | BCST25 B naive (CD19+) | BCST26 B mem (CD19+) | Mean Value Target Cell Type | Mean Value Rest | Delta Meth (Target-Rest) |
|---|---|---|---|---|---|---|---|---|---|---|---|---|---|---|---|---|---|---|
| cg18350391 | IL32 | 16 | 33/ NM_001012631.1 | 0.332 | 0.724 | 0.794 | 0.937 | 0.901 | 0.658 | 0.296 | 0.169 | 0.15 | 0.192 | 0.881 | 0.406 | 0.202 | 0.704 | −0.502 |
| cg25226014 | CXCR6 | 3 | 34/ NM_006564.1 | 0.702 | 0.481 | 0.548 | 0.789 | 0.89 | 0.35 | 0.028 | 0.046 | 0.046 | 0.193 | 0.258 | 0.514 | 0.078 | 0.567 | −0.488 |
| cg13578652 | UBASH3A | 21 | 35/ NM_018961.2 | 0.564 | 0.444 | 0.475 | 0.537 | 0.703 | 0.169 | 0.027 | 0.04 | 0.035 | 0.05 | 0.602 | 0.673 | 0.038 | 0.521 | −0.483 |
| cg25712380 | GRAP2 | 22 | 36/ NM_004810.2 | 0.633 | 0.602 | 0.639 | 0.824 | 0.83 | 0.506 | 0.097 | 0.093 | 0.089 | 0.1 | 0.179 | 0.310 | 0.095 | 0.565 | −0.470 |
| cg19812619 | ITGB7 | 12 | 37/ NM_000889.1 | 0.819 | 0.651 | 0.785 | 0.874 | 0.897 | 0.645 | 0.3374 | 0.275 | 0.199 | 0.177 | 0.608 | 0.4337 | 0.247 | 0.714 | −0.467 |
| cg02600394 | TXK | 4 | 38/ NM_003328.1 | 0.775 | 0.576 | 0.682 | 0.867 | 0.909 | 0.082 | 0.036 | 0.075 | 0.051 | 0.354 | 0.376 | 0.484 | 0.129 | 0.594 | −0.465 |

We claim:

1. A method for producing an amplicon from a bisulfite treated human CD3 genetic region, the method comprising:
   a) bisulfite treating genomic DNA obtained from a human sample to produce bisulfite treated DNA, and
   b) amplifying a CD3 genetic region from the bisulfite treated DNA with at least one primer pair to produce the amplicon,
   wherein the amplicon comprises the sequence of SEQ ID NO: 43, SEQ ID NO: 55, or SEQ ID NO: 60.

2. The method according to claim 1, wherein the amplifying is performed from the 5' region upstream from the transcription start, and/or promoter region of CD3D gene or CD3G gene.

3. The method according to claim 1, further comprising detecting methylation status of at least one CpG position by a method selected from methylation specific enzymatic digests, bisulphite sequencing, analysis selected from promoter methylation, CpG island methylation, methylation-specific polymerase chain reaction (MSP), quantitative polymerase chain reaction (qPCR), methylation-sensitive single-nucleotide primer extension (Ms-SNuPE) or other methods relying on a detection of amplified DNA.

4. The method according to claim 1, wherein said sample is selected from a human body fluid, a human blood sample, a tissue, an organ, a cell type blood sample, or a sample of blood lymphocytes.

5. The method according to claim 1, wherein said human suffers from autoimmune diseases, transplant rejections, cancer, and/or allergy.

6. The method of claim 1, wherein the amplicon comprises SEQ ID NO: 55 and SEQ ID NO: 43 or SEQ ID NO: 55 and SEQ ID NO: 60.

* * * * *